(12) United States Patent
Yang et al.

(10) Patent No.: US 11,999,790 B2
(45) Date of Patent: Jun. 4, 2024

(54) ANTI-OX40 ANTIBODIES AND USES THEREOF

(71) Applicant: Eucure (Beijing) Biopharma Co., Ltd, Beijing (CN)

(72) Inventors: Yi Yang, Beijing (CN); Yanan Guo, Beijing (CN); Yunyun Chen, Beijing (CN); Jingshu Xie, Beijing (CN); Chunyan Dong, Beijing (CN); Fang Yang, Beijing (CN); Chengyuan Lu, Beijing (CN); Xiaodong Cheng, Beijing (CN); Yuelei Shen, Beijing (CN); Jian Ni, Beijing (CN)

(73) Assignee: Eucure (Beijing) Biopharma Co., Ltd, Beijing (CN)

( * ) Notice: Subject to any disclaimer, the term of this patent is extended or adjusted under 35 U.S.C. 154(b) by 485 days.

(21) Appl. No.: 17/141,406

(22) Filed: Jan. 5, 2021

(65) Prior Publication Data

US 2021/0206866 A1 Jul. 8, 2021

Related U.S. Application Data

(60) Division of application No. 16/882,096, filed on May 22, 2020, now Pat. No. 10,934,365, which is a continuation of application No. PCT/CN2017/112832, filed on Nov. 24, 2017.

(51) Int. Cl.
*C07K 16/28* (2006.01)
*A61P 35/04* (2006.01)
*A61K 39/00* (2006.01)
*A61K 47/68* (2017.01)

(52) U.S. Cl.
CPC .......... *C07K 16/2878* (2013.01); *A61P 35/04* (2018.01); *A61K 2039/505* (2013.01); *A61K 47/6849* (2017.08); *C07K 2317/24* (2013.01); *C07K 2317/33* (2013.01); *C07K 2317/565* (2013.01); *C07K 2317/622* (2013.01)

(58) Field of Classification Search
CPC ....................... C07K 16/2878; C07K 2317/565
USPC ........................................... 424/133.1, 178.1
See application file for complete search history.

(56) References Cited

U.S. PATENT DOCUMENTS

| | | | |
|---|---|---|---|
| 4,522,811 A | 6/1985 | Eppstein | |
| 4,603,112 A | 7/1986 | Paoletti | |
| 4,676,980 A | 6/1987 | Segal | |
| 4,769,330 A | 9/1988 | Paoletti | |
| 4,777,127 A | 10/1988 | Suni | |
| 5,017,487 A | 5/1991 | Stunnenberg | |
| 10,934,365 B2 * | 3/2021 | Yang | C07K 16/2803 |
| 2007/0071675 A1 | 3/2007 | Wu et al. | |
| 2015/0038682 A1 | 2/2015 | Tsurushita et al. | |
| 2015/0307617 A1 | 10/2015 | Du | |
| 2020/0291117 A1 | 9/2020 | Yang | |
| 2020/0332007 A1 | 10/2020 | Yang et al. | |
| 2020/0332018 A1 | 10/2020 | Yang et al. | |
| 2021/0198239 A1 * | 7/2021 | Vander Wal | A61P 35/00 |

FOREIGN PATENT DOCUMENTS

| | | |
|---|---|---|
| EP | 0345242 | 12/1989 |
| GB | 2200651 | 8/1988 |
| JP | 2016-515544 | 5/2016 |
| JP | 2017-532037 | 11/2017 |
| RU | 2008/129111 | 1/2010 |
| WO | WO 1989/01973 | 3/1989 |
| WO | WO 1991/02805 | 3/1991 |
| WO | WO 1996/27011 | 9/1996 |
| WO | WO 2001/77342 | 10/2001 |
| WO | WO 2003/059245 | 7/2003 |
| WO | WO 2007/062245 | 5/2007 |
| WO | WO 2008/077546 | 7/2008 |
| WO | WO 2009/079335 | 6/2009 |
| WO | WO 2014/148895 | 9/2014 |
| WO | WO 2016/057667 | 4/2016 |
| WO | WO 2016/196228 | 12/2016 |
| WO | WO 2017/063162 | 4/2017 |
| WO | WO 2017/096182 | 6/2017 |
| WO | WO 2018/041119 | 3/2018 |
| WO | WO_2021098851 * | 5/2021 |
| WO | WO 2021098851 * | 5/2021 |

OTHER PUBLICATIONS

Pan et al., "Blocking neuropilin-1 function has an additive effect with anti-VEGF to inhibit tumor growth," Cancer cell, Jan. 1, 2007, 11(1):53-67.
Supplementary Partial European Search Report in European Appln. No. 17932798.6, dated Jun. 4, 2021, 16 pages.
Abhinandan et al., "Analysis and improvements to Kabat and structurally correct numbering of antibody variable domains", Molecular immunology 45, 14, 3832-3839, 2008.
Aspeslagh et al. "Rationale for anti-OX40 cancer immunotherapy" European Journal of Cancer 52, 50-66, 2016.
Chothia et al., "Canonical structures for the hypervariable regions of immunoglobulins", J. Mol. Biol., 196: 901, 1987.
Chothia et al., "Conformations of immunoglobulin hypervariable regions", Nature 342(6252): 877-83, 1989.
Curti et al., "OX40 Is a Potent Immune-Stimulating Target in Late-Stage Cancer Patients", Cancer research 73.24, 7189-7198, 2013.
Fisher-Hoch et al., "Protection of Rhesus Monkeys From Fatal Lassa Fever by Vaccination With a Recombinant Vaccinia Virus Containing the Lassa Virus Glycoprotein Gene", Proc. Natl. Acad. Sci. USA 86: 317-321, 1989.
George et al., Differential Effects of Anti-$\beta_2$-Glycoprotein I Antibodies on Endothelial Cells and on the Manifestations of Experimental Antiphospholipid Syndrome, American Heart Association, Inc, 1998, 97:900-906.

(Continued)

*Primary Examiner* — Lynn A Bristol
(74) *Attorney, Agent, or Firm* — Fish & Richardson P.C.

(57) ABSTRACT

This disclosure relates to anti-human OX40 (TNF Receptor Superfamily Member 4, or TNFRSF4) antibodies, antigen-binding fragments, and the uses thereof.

17 Claims, 37 Drawing Sheets
Specification includes a Sequence Listing.

(56) References Cited

OTHER PUBLICATIONS

Ghetie et al., "Homodimerization of tumor-reactive monoclonal antibodies markedly increases their ability to induce growth arrest or apoptosis of tumor cells", Proc. Natl. Acad Sci. US.A. 94: 7509-7514, 1997.
Guzman et al., "Efficient and Selective Adenovirus-Mediated Gene Transfer Into Vascular Neointima", Circulation, 88: 2838-2848, 1993.
Guzman et al., "Efficient Gene Transfer Into Myocardium by Direct Injection of Adenovirus Vectors", Cir. Res., 73: 1202-1207, 1993.
Irani et al., "Molecular properties of human IgG subclasses and their implications for designing therapeutic monoclonal antibodies against infectious diseases." Molecular immunology vol. 67, issue 2, 171-182, 2015.
Jones et al., "Replacing the Complementarity-Determining Regions in a Human Antibody With Those From a Mouse", Nature, 321: 522-525, 1986.
Jones et al., "The INNs and outs of antibody nonproprietary names" MAbs. vol. 8. No. 1. Taylor & Francis, 9 pages, 2016.
Kass-Eisler et al., "Quantitative determination of adenovirus-mediated gene delivery to rat cardiac myocytes in vitro and in vivo", Proc. Natl. Acad. Sci. USA, 90: 11498-11502, 1993.
Kolker, "Antibdies and the written description requirement of 35 U.S.C. 112(a)," Sep. 17, 2020, p. 1-36.
Kolls et al., "Prolonged and effective blockade of tumor necrosis factor activity through adenovirus-mediated gene transfer", Proc. Natl. Acad. Sci. USA, 91: 215-219, 1994.
Morea et al., "Conformations of the third hypervariable region in the VH domain of immunoglobulins," Journal of molecular biology, Jan. 16, 1998, 275(2):269-294.
PCT International Preliminary Report on Patentability in International Appln. No. PCT/CN2017/112832, dated May 26, 2020, 8 pages.
PCT International Search Report and Written Opinion in International Appln. No. PCT/CN2017/112832, dated Aug. 29, 2018, 14 pages.
Ponomarenko and Bourne, "Antibody-protein interactions: benchmark datasets and prediction tools evaluation", BMC Structural Biology 7: 64, 19 pages, 2007.
Riechmann et al., "Reshaping human antibodies for therapy", Nature, 332: 323-327, 1988.
Vidarsson et al, "IgG Subclasses and Allotypes: From Structure to Effector Functions" Frontiers in immunology 5, 17 pages, 2014.
Wolff et al., "Monoclonal Antibody Homodimers: Enhanced Antitumor Activity in Nude Mice", Cancer Res. 53: 2560-2565, 1993.
Wu et al., "An analysis of the sequences of the variable regions of Bence Jones proteins and myeloma light chains and their implications for antibody complementarity", J. Exp. Med. 132: 211-250, 1970.
Zhao et al., "Enhancing Tumor Targeting and Apoptosis Using Noncovalent Antibody Homodimers", J Immunol. 25: 396-404, 2002.
Lin et al., "Construction of the Prokaryotic Expression Vector of Mouse OX40 Gene and Its Expression," Acta Acad Med Weifang, Jun. 2008, 30(3):202-204.
Xu, "Research progress on the role of OX40 / OX40L in immune response and its relationship with diseases," China Practical Medicine, May 2008, 3(14):139-141 (with machine translation).
Extended European Search Report in European Appln. No. 17932798. 6, dated Oct. 4, 2021, 15 pages.
Foote et al., "Antibody framework residues affecting the conformation of the hypervariable loops," J. Mol. Biol., 1992, 224:487-499.
Winter et al., "Humanized antibodies," Immunology Today, 1993, 14(6):243-246.

\* cited by examiner

Intestine Tissue Pathology (H&E staining; 400X)

hIgG (#25867)
 hIgG (#25861)
 hIgG (#25829)
 OX40 (#25878)
 OX40 (#25874)
 OX40 (#25832)

Kabat CDR

| Ab | VH CDR1 | SEQ ID: | VH CDR2 | SEQ ID: | VH CDR3 | SEQ ID: | VL CDR1 | SEQ ID: | VL CDR2 | SEQ ID: | VL CDR3 | SEQ ID: |
|---|---|---|---|---|---|---|---|---|---|---|---|---|
| 07-9H3 or humanized 07-9H3 | SYGVL | 1 | VIWSGGSTDYNAAFIS | 2 | EEFGY | 3 | RASQDINNYLN | 4 | YTSRLHS | 5 | QQTNTLPWT | 6 |
| 07-9A4 or humanized 07-9A4 | DYNMD | 7 | DINPNYDSTSYNQKFKG | 8 | GGYGNYVDYFDY | 9 | KASENVVTYVS | 10 | GASNRYT | 11 | GQSYSYPYT | 12 |
| 11-5C1 or humanized 11-5C1 | SYWMH | 13 | TIYPGNSDTSNNQKFKG | 14 | FYYRYEDYYAMDY | 15 | KASQDVNTAVA | 16 | SASYRYT | 17 | QQHYSTPFT | 18 |
| 17-5D10 or humanized 17-5D10 | SYGVH | 19 | VIWAGGNTNYNSALMS | 20 | YDGYYGWFAY | 21 | RASQDISYYLN | 22 | YTSRLHS | 23 | QQGHTLPWT | 24 |

FIG. 31

Chothia CDR

| Ab | VH CDR1 | SEQ ID: | VH CDR2 | SEQ ID: | VH CDR3 | SEQ ID: | VL CDR1 | SEQ ID: | VL CDR2 | SEQ ID: | VL CDR3 | SEQ ID: |
|---|---|---|---|---|---|---|---|---|---|---|---|---|
| 07-9H3 or humanized 07-9H3 | GFSLT SYGVL | 25 | WSGGS | 26 | EEFGY | 27 | RASQDINNYLN | 28 | YTSRLHS | 29 | QQTNTLP WT | 30 |
| 07-9A4 or humanized 07-9A4 | GYTF TDY NMD | 31 | NPNYDS | 32 | GGYGNY VDYFDY | 33 | KASENVVT YVS | 34 | GASNR YT | 35 | GQSYS YPYT | 36 |
| 11-5C1 or humanized 11-5C1 | GYSFT SYWM H | 37 | YPGNSD | 38 | FYYRYEDYY AMDY | 39 | KASQDVNTAV A | 40 | SASYRYT | 41 | QQHYSTP FT | 42 |
| 17-5D10 or humanized 17-5D10 | GFSLT SYGVH | 43 | WAGGN | 44 | YDGYYGWF AY | 45 | RASQDISYYLN | 46 | YTSRLHS | 47 | QQGHTL PWT | 48 |

FIG. 32

| Protein | Amino acid sequence | SEQ ID NO: |
|---|---|---|
| Human OX40 (hOX40) NP_003318.1 | MCVGARRLGR GPCAALLLLG LGLSTVTGLH CVGDTYPSND RCCHECRPGN GMVSRCSRSQ NTVCRPCGPG FYNDVVSSKP CKPCTWCNLR SGSERKQLCT ATQDTVCRCR AGTQPLDSYK PGVDCAPCPP GHFSPGDNQA CKPWTNCTLA GKHTLQPASN SSDAICEDRD PPATQPQETQ GPPARPITVQ PTEAWPRTSQ GPSTRPVEVP GGRAVAAILG LGLVLGLLGP LAILLALYLL RRDQRLPPDA HKPPGGGSFR TPIQEEQADA HSTLAKI | 49 |
| Mouse OX40 (mOX40) NP_035789.1 | MYWVQQPTA LLLLGLTLGV TARRLNCVKH TYPSGHKCCR ECQPGHGMVS RCDHTRDTLC HPCETGFYNE AVNYDTCKQC TQCNHRSGSE LKQNCTPTQD TVCRCRPGTQ PRQDSGYKLG VDCVPCPPGH FSPGNNQACK PWTNCTLSGK QTRHPASDSL DAVCEDRSLL ATLLWETQRP TFRPTTVQST TVWPRTSELP SPPTLVTPEG PAFAVLLGLG LGLLAPLTVL LALYLLRKAW RLPNTPKPCW GNSFRTPIQE EHTDAHFTLA KI | 50 |
| Monkey OX40 (rmOX40) XP_0010908 70.1 | MCVGARRLGR GPCAALLLLG LGLSTTAKLH CVGDTYPSND RCCQECRPGN GMVSRCNRSQ NTVCRPCGPG FYNDVVSAKP CKACTWCNLR SGSERKQPCT ATQDTVCRCR AGTQPLDSYK PGVDCAPCPP GHFSPGDNQA CKPWTNCTLA GKHTLQPASN SSDAICEDRD PPPTQPQETQ GPPARPTTVQ PTEAWPRTSQ RPSTRPVEVP RGPAVAAILG LGLALGLLGP LAMLLALLLL RRDQRLPPDA PKAPGGGSFR TPIQEEQADA HSALAKI | 51 |
| Chimeric OX40 (chiOX40) (Humanized OX40) | MYWVQQPTALLLLGLTLGVTARRLNCVKHTYPSNDRCCHECRPGNGMVSRCSRSQNTVCRPCGPGFYND VVSSKPCKPCTWCNLRSGSERKQLCTATQDTVCRCRAGTQPLDSYKPGVDCAPCPPGHFSPGDNQACKPW TNCTLAGKHTLQPASNSSDAICEDRDPPATQPQETQGPPARPITVQPTEAWPRTSELPSPPTLVTPEGPA FAVLLGLGLGLLAPLTVLLLALYLLRKAWRLPNTPKPCWGNSFRTPIQEEHTDAHFTLAKI | 52 |

| Humanized antibody variable domains | Description | AMINO ACID SEQUENCE | SEQ ID NO: |
|---|---|---|---|
| 9H3 Humanized heavy chain variable domain (H1) | HuVHv1: humanization percentage 81.6%; top hit to human and *Macaca fascicularis* | QVQLVESGGGVVQPGRSLRLSCAASGFSLTSYGVLWVRQAP GKGLEWLAVIWSGGSTDYNAAFISRLTISRDNSKSTLYFQM NSLRAEDTAVYYCAREEFGYWGQGTLVTVSS | 53 |
| 9H3 Humanized heavy chain variable domain (H2) | HuVHv2: humanization percentage 78.6%; top hit to human and *Macaca fascicularis* | QVQLVESGGGVVQPGRSLRISCAVSGFSLTSYGVLWVRQAP GKGLEWLAVIWSGGSTDYNAAFISRLTISRDNSKSTVYFQM NSLRAEDTAVYYCAREEFGYWGQGTLVTVSS | 54 |
| 9H3 Humanized heavy chain variable domain (H3) | HuVHv3: humanization percentage 76.5%; not top hit to human and *Macaca fascicularis* | QVQLVESGGGVVQPGRSLRISCAVSGFSLTSYGVLWVRQAP GKGLEWLGVIWSGGSTDYNAAFISRLTISRDNSKSTVYFQM NSLRAEDTAVYYCAREEFGYWGQGTLVTVSS | 55 |
| 9H3 Humanized light chain variable domain (K1) | HuVLv1: humanization percentage 87.4%; top hit to human and *Macaca fascicularis* | DIQMTQSPSSLSASVGDRVTITCRASQDINNYLNWYQQKPG GAVKLLIYYTSRLHTGVPSRFSGSGSGTDFTLTISSLQPED IATYYCQQTNTLPWTFGGGTKLEVKR | 56 |
| 9H3 Humanized light chain variable domain (K2) | HuVLv2: humanization percentage 86.3%; not top hit to human and *Macaca fascicularis* | DIQMTQSPSSLSASVGDRVTITCRASQDINNYLNWYQQKPG GAVKLLIYYTSRLHSGVPSRFSGSGSGTDFTLTISSLQPED IATYYCQQTNTLPWTFGGGTKLEIKR | 57 |
| 9H3 Humanized light chain variable domain (K3) | HuVLv3: humanization percentage 84.2%; not top hit to human and *Macaca fascicularis* | DIQMTQSPSSLSASVGDRVTITCRASQDINNYLNWYQQKPG GAVKLLIYYTSRLHSGVPSRFSGSGSGTDYTLTISSLQPED IATYFCQQTNTLPWTFGGGTKLEIKR | 58 |
| 9A4 Humanized heavy chain variable domain (H1) | HuVHv1: humanization percentage 81.6%; not top hit to human and *Macaca fascicularis* | EVQLQQSGAEVKKPGASVKVSCKASGYTFTDYNMDWVRQAP GKGLEWIGDINPNYDSTSYNQKFKGRATLTVDKSTSTAYME LSSLRSEDTAVYYCARGGYGNYVDYFDYWGQGTLVTVSS | 59 |
| 9A4 Humanized heavy chain variable domain (H2) | HuVHv2: humanization percentage 80.6%; not top hit to human and *Macaca fascicularis* | EVQLQQSGAEVKKPGASVKVSCKASGYTFTDYNMDWVKQAP GKGLEWIGDINPNYDSTSYNQKFKGRATLTVDKSTSTAYME LSSLRSEDTAVYYCARGGYGNYVDYFDYWGQGTLVTVSS | 60 |

FIG. 34 (Continued)

| | | | |
|---|---|---|---|
| 9A4 Humanized heavy chain variable domain (H3) | HuVHv3: humanization percentage 78.6%; not top hit to human and Macaca fascicularis | EVQLQQSGAEVVKPGASVKISCKASGYTFTDYNMDWVKQAP GKGLEWIGDINPNYDSTSYNQKFKGRATLTVDKSTSTAYME LSSLRSEDTAVYYCARGGYGNYVDYFDYWGQGTLLTVSS | 61 |
| 9A4 Humanized light chain variable domain (K1) | HuVLv1: humanization percentage 84.4%; top hit to human and Macaca fascicularis | EIVMTQSPATLSLSPGERATLSCKASENVVTYVSWYQQKPG QAPRLLIYGASNRYTGIPARFSGSGSGTDFTLTISSLQPED FADYHCGQSYSYPYTFGQGTKLEIK | 62 |
| 9A4 Humanized light chain variable domain (K2) | HuVLv2: humanization percentage 84.2%; top hit to human and Macaca fascicularis | NIVMTQSPATLSLSPGERATLSCKASENVVTYVSWYQQKPG QAPRLLIYGASNRYTGIPARFSGSGSGTDFLTISSLQPED FADYHCGQSYSYPYTFGQGTKLEIK | 63 |
| 9A4 Humanized light chain variable domain (K3) | HuVLv3: humanization percentage 80%; not top hit to human and Macaca fascicularis | NIVMTQSPATLSLSPGERATLSCKASENVVTYVSWYQQKPG QAPRLLIYGASNRYTGVPDRFSGSGSATDFTLTISSVQPED FADYHCGQSYSYPYTFGQGTKLEIK | 64 |
| 9A4 Humanized light chain variable domain (K4) | HuVLv4: humanization percentage 77.9%; not top hit to human and Macaca fascicularis | NIVMTQSPATLSLSPGERATLSCKASENVVTYVSWYQQKPG QSPRLLIYGASNRYTGVPDRFTGSGSATDFTLTISSVQPED FADYHCGQSYSYPYTFGQGTKLEIK | 65 |
| 5C1 Humanized heavy chain variable domain (H1) | HuVHv1: humanization percentage 81.2%; not top hit to human and Macaca fascicularis | QVQLVQSGAEVKKPGASVKMSCKASGYSFTSYWMHWVRQRP GQGLEWIGTIYPGNSDTSNNQKFKGRVKLITADTSASTAYME LSSLRSEDTAVYYCTTFYYRYEDYYAMDYWGQGTLVTVSS | 66 |
| 5C1 Humanized heavy chain variable domain (H2) | HuVHv2: humanization percentage 80.2%; not top hit to human and Macaca fascicularis | EVQLVQSGAEVKKPGASVKMSCKASGYSFTSYWMHWVRQRP GQGLEWIGTIYPGNSDTSNNQKFKGRVKLITADTSASTAYME LSSLRSEDTAVYYCTTFYYRYEDYYAMDYWGQGTLVTVSS | 67 |
| 5C1 Humanized heavy chain variable domain (H3) | HuVHv3: humanization percentage 79.2%; not top hit to human and Macaca fascicularis | EVQLVQSGAEVKKPGASVKMSCKASGYSFTSYWMHWVRQRP GQGLEWIGTIYPGNSDTSNNQKFKGRAKLTADTSASTAYME LSSLRSEDTAVYYCTTFYYRYEDYYAMDYWGQGTLVTVSS | 68 |
| 5C1 Humanized light chain variable domain (K1) | HuVLv1: humanization percentage 84.2%; top hit to human and Macaca fascicularis | DIQMTQSPSSLSASVGDRVTITCKASQDVNSAVAWYQQKPG KAPKLLIYSASYRYTGVPSRFSGSGSGTDFTFTISSLQPED FAVYYCQQHYSTPFTFGQGTKLEIK | 69 |
| 5C1 Humanized light chain variable domain (K2) | HuVLv2: humanization percentage 83.2%; not top hit to human and Macaca fascicularis | DIQMTQSPSSLSASVGDRVTITCKASQDVNTAVAWYQQKPG KAPKLLIYSASYRYTGVPSRFSGSGSGTDFTFTISSLQPED FAVYYCQQHYSTPFTFGQGTKLEIK | 70 |

FIG. 34 (Continued)

| | | | |
|---|---|---|---|
| 5C1 Humanized light chain variable domain (K3) | HuVLv3: humanization percentage 82.1%; not not top hit to human and *Macaca fascicularis* | DIQMTQSPSSLSASVGDRVTITCKASQDVNTAVAWYQQKPG KSPKLLIYSASYRYTGVPSRFSGSGSGTDFTFTISSLQPED FAVYYCQQHYSTPFTFGQGTKLEIK | 71 |
| 5C1 Humanized light chain variable domain (K4) | HuVLv4: humanization percentage 77.9%; not not top hit to human and Macaca fascicularis | DIVMTQSPSSMSASVGDRVTITCKASQDVNTAVAWYQQKPG KSPKLLIYSASYRYTGVPDRFSGSGSGTDFTFTISSVQPED FAVYYCQQHYSTPFTFGQGTKLEIK | 72 |
| 5D10 Humanized heavy chain variable domain (H1) | HuVHv1: humanization percentage 81.2%; top hit to human and *Macaca fascicularis* | QVQLQESGPGLVKPSETLSLTCTVSGFSLTSYGVHWIRQPP GKGLEWIGVIWAGGNTNYNSALMSRLTISKDTSKNQVSLKM SSVTAADTAVYYCASYDGYYGWFAYWGQGTLVTVSV | 73 |
| 5D10 Humanized heavy chain variable domain (H2) | HuVHv2: humanization percentage 77.1%; not top hit to human and *Macaca fascicularis* | QVQLQESGPGLVKPSETLSITCTVSGFSLTSYGVHWIRQPP GKGLEWLGVIWAGGNTNYNSALMSRLTISKDNSKSQVSLKM SSVTAADTAVYYCASYDGYYGWFAYWGQGTLVTVSV | 74 |
| 5D10 Humanized heavy chain variable domain (H3) | HuVHv3: humanization percentage 75%; not top hit to human and *Macaca fascicularis* | QVQLQESGPGLVKPSETLSITCTVSGFSLTSYGVHWIRQPP GKGLEWLGVIWAGGNTNYNSALMSRLTISKDNSKSQVSLKM SSVTAADTAMYNCASYDGYYGWFAYWGQGTLVTVSV | 75 |
| 5D10 Humanized light chain variable domain (K1) | HuVLv1: humanization percentage 86.3%; not top hit to human and *Macaca fascicularis* | DIQMTQSPSSLSASVGDRVTITCRASQDISYYLNWYQQKPG KAVKLLIYYTSRLHSGVPSRFSGSGSGTDYTLTISSLQPED FATYFCQQGHTLPWTFGGGTKLEIK | 76 |
| 5D10 Humanized light chain variable domain (K2) | HuVLv2: humanization percentage 85.3%; not top hit to human and *Macaca fascicularis* | DIQMTQSPSSLSASVGDRVTITCRASQDISYYLNWYQQKPG GAVKLLIYYTSRLHSGVPSRFSGSGSGTDYTLTISSLQPED FATYFCQQGHTLPWTFGGGTKLEIK | 77 |
| 5D10 Humanized light chain variable domain (K3) | HuVLv3: humanization percentage 82.1%; not top hit to human and *Macaca fascicularis* | DIQMTQSTSSLSASVGDRVTITCRASQDISYYLNWYQQKPG GAVKLLIYYTSRLHSGVPSRFSGSGSGTDYTLTISSLQQED IATYFCQQGHTLPWTFGGGTKLEIK | 78 |

07-9H3 ("9H3") Heavy chain variable region (SEQ ID NO: 79)
QVQLKQSGPGLVQPSQSLSITCTVSGFSLTSYGVLWVRQPPGKGLEWLGVIWSGGST
DYNAAFISRLSISKDNSKSQVFFKMNSLQADDTAIYYCAREEFGYWGQGTLVTVSA 07-9H3 ("9H3") Light chain variable region (SEQ ID NO: 80)
DIQMTQTTSSLSASLGDRVTISCRASQDINNYLNWYQQKPDGTVKLLIYYTSRLHSGV
PSRFSGSGSGTDYSLTISNLEQEDIATYFCQQTNTLPWTFGGGTKLEIK 07-9A4 ("9A4") Heavy chain variable region (SEQ ID NO: 81)
EVQLQQFGAELVKPGASVKISCKASGYTFTDYNMDWVKQSHGKSLEWIGDINPNYDS
TSYNQKFKGKATLTVDKSSSTAYMELRSLTSEDTAVYYCARGGYGNYVDYFDYWGQ
GTTLTVSS 07-9A4 ("9A4") Light chain variable region (SEQ ID NO: 82)
NIVMTQSPKSMSMSVGERVTLSCKASENVVTYVSWYQQKPEQSPKLLIYGASNRYTG
VPDRFTGSGSATDFTLTISSVQAEDLADYHCGQSYSYPYTFGGGTKLEIK 11-5C1 ("5C1") Heavy chain variable region (SEQ ID NO: 83)
EVQLQQSGTVLARPGASVKMSCKASGYSFTSYWMHWVKQRPGQGLEWIGTIYPGNS
DTSNNQKFKGKAKLTAVTSASTAYMELSSLTNEDSAVYYCTTFYYRYEDYYAMDYW
GQGTSVTVSS 11-5C1 ("5C1") Light chain variable region (SEQ ID NO: 84)
DIVMTQSHKFMSTSVGDRVSITCKASQDVNTAVAWYQQKPGQSPKLLIYSASYRYTG
VPDRFTGSGSGTDFTFTISSVQAEDLAVYYCQQHYSTPFTFGSGTKLEIK 17-5D10 ("5D10") Heavy chain variable region (SEQ ID NO: 85)
QVQLKESGPGLVAPSQSLSITCTVSGFSLTSYGVHWIRQPPGKGLEWLGVIWAGGNT
NYNSALMSRLSISKDNSKSQVFLKMNSLQTDDTAMYNCASYDGYYGWFAYWGQGTL
VTVSV 17-5D10 ("5D10") Light chain variable region (SEQ ID NO: 86)
DIQMTQTTSSLSASLGDRVTISCRASQDISYYLNWYQQKPDGTVKLLIYYTSRLHSGV
PSRFSGSGSGTDYSLTISNLEQEDIATYFCQQGHTLPWTFGGGTKLEIK

FIG. 35

SEQUENCE LISTING

```
<160> NUMBER OF SEQ ID NOS: 86

<210> SEQ ID NO 1
<211> LENGTH: 5
<212> TYPE: PRT
<213> ORGANISM: Artificial
<220> FEATURE:
<223> OTHER INFORMATION: CDR sequence

<400> SEQUENCE: 1

Ser Tyr Gly Val Leu
1               5

<210> SEQ ID NO 2
<211> LENGTH: 16
<212> TYPE: PRT
<213> ORGANISM: Artificial
<220> FEATURE:
<223> OTHER INFORMATION: CDR sequence

<400> SEQUENCE: 2

Val Ile Trp Ser Gly Gly Ser Thr Asp Tyr Asn Ala Ala Phe Ile Ser
1               5                   10                  15

<210> SEQ ID NO 3
<211> LENGTH: 5
<212> TYPE: PRT
<213> ORGANISM: Artificial
<220> FEATURE:
<223> OTHER INFORMATION: CDR sequence

<400> SEQUENCE: 3

Glu Glu Phe Gly Tyr
1               5

<210> SEQ ID NO 4
<211> LENGTH: 11
<212> TYPE: PRT
<213> ORGANISM: Artificial
```

```
<220> FEATURE:
<223> OTHER INFORMATION: CDR sequence

<400> SEQUENCE: 4

Arg Ala Ser Gln Asp Ile Asn Asn Tyr Leu Asn
1               5                   10

<210> SEQ ID NO 5
<211> LENGTH: 7
<212> TYPE: PRT
<213> ORGANISM: Artificial
<220> FEATURE:
<223> OTHER INFORMATION: CDR sequence

<400> SEQUENCE: 5

Tyr Thr Ser Arg Leu His Ser
1               5

<210> SEQ ID NO 6
<211> LENGTH: 9
<212> TYPE: PRT
<213> ORGANISM: Artificial
<220> FEATURE:
<223> OTHER INFORMATION: CDR sequence

<400> SEQUENCE: 6

Gln Gln Thr Asn Thr Leu Pro Trp Thr
1               5

<210> SEQ ID NO 7
<211> LENGTH: 5
<212> TYPE: PRT
<213> ORGANISM: Artificial
<220> FEATURE:
<223> OTHER INFORMATION: CDR sequence

<400> SEQUENCE: 7

Asp Tyr Asn Met Asp
1               5

<210> SEQ ID NO 8
<211> LENGTH: 17
<212> TYPE: PRT
<213> ORGANISM: Artificial
<220> FEATURE:
<223> OTHER INFORMATION: CDR sequence

<400> SEQUENCE: 8

Asp Ile Asn Pro Asn Tyr Asp Ser Thr Ser Tyr Asn Gln Lys Phe Lys
1               5                   10                  15

Gly

<210> SEQ ID NO 9
<211> LENGTH: 12
<212> TYPE: PRT
<213> ORGANISM: Artificial
<220> FEATURE:
<223> OTHER INFORMATION: CDR sequence

<400> SEQUENCE: 9

Gly Gly Tyr Gly Asn Tyr Val Asp Tyr Phe Asp Tyr
1               5                   10

<210> SEQ ID NO 10
<211> LENGTH: 11
<212> TYPE: PRT
```

<213> ORGANISM: Artificial
<220> FEATURE:
<223> OTHER INFORMATION: CDR sequence

<400> SEQUENCE: 10

Lys Ala Ser Glu Asn Val Val Thr Tyr Val Ser
1               5                   10

<210> SEQ ID NO 11
<211> LENGTH: 7
<212> TYPE: PRT
<213> ORGANISM: Artificial
<220> FEATURE:
<223> OTHER INFORMATION: CDR sequence

<400> SEQUENCE: 11

Gly Ala Ser Asn Arg Tyr Thr
1               5

<210> SEQ ID NO 12
<211> LENGTH: 9
<212> TYPE: PRT
<213> ORGANISM: Artificial
<220> FEATURE:
<223> OTHER INFORMATION: CDR sequence

<400> SEQUENCE: 12

Gly Gln Ser Tyr Ser Tyr Pro Tyr Thr
1               5

<210> SEQ ID NO 13
<211> LENGTH: 5
<212> TYPE: PRT
<213> ORGANISM: Artificial
<220> FEATURE:
<223> OTHER INFORMATION: CDR sequence

<400> SEQUENCE: 13

Ser Tyr Trp Met His
1               5

<210> SEQ ID NO 14
<211> LENGTH: 17
<212> TYPE: PRT
<213> ORGANISM: Artificial
<220> FEATURE:
<223> OTHER INFORMATION: CDR sequence

<400> SEQUENCE: 14

Thr Ile Tyr Pro Gly Asn Ser Asp Thr Ser Asn Asn Gln Lys Phe Lys
1               5                   10                  15

Gly

<210> SEQ ID NO 15
<211> LENGTH: 13
<212> TYPE: PRT
<213> ORGANISM: Artificial
<220> FEATURE:
<223> OTHER INFORMATION: CDR sequence

<400> SEQUENCE: 15

Phe Tyr Tyr Arg Tyr Glu Asp Tyr Tyr Ala Met Asp Tyr
1               5                   10

<210> SEQ ID NO 16
<211> LENGTH: 11

```
<212> TYPE: PRT
<213> ORGANISM: Artificial
<220> FEATURE:
<223> OTHER INFORMATION: CDR sequence

<400> SEQUENCE: 16

Lys Ala Ser Gln Asp Val Asn Thr Ala Val Ala
1               5                   10

<210> SEQ ID NO 17
<211> LENGTH: 7
<212> TYPE: PRT
<213> ORGANISM: Artificial
<220> FEATURE:
<223> OTHER INFORMATION: CDR sequence

<400> SEQUENCE: 17

Ser Ala Ser Tyr Arg Tyr Thr
1               5

<210> SEQ ID NO 18
<211> LENGTH: 9
<212> TYPE: PRT
<213> ORGANISM: Artificial
<220> FEATURE:
<223> OTHER INFORMATION: CDR sequence

<400> SEQUENCE: 18

Gln Gln His Tyr Ser Thr Pro Phe Thr
1               5

<210> SEQ ID NO 19
<211> LENGTH: 5
<212> TYPE: PRT
<213> ORGANISM: Artificial
<220> FEATURE:
<223> OTHER INFORMATION: CDR sequence

<400> SEQUENCE: 19

Ser Tyr Gly Val His
1               5

<210> SEQ ID NO 20
<211> LENGTH: 16
<212> TYPE: PRT
<213> ORGANISM: Artificial
<220> FEATURE:
<223> OTHER INFORMATION: CDR sequence

<400> SEQUENCE: 20

Val Ile Trp Ala Gly Gly Asn Thr Asn Tyr Asn Ser Ala Leu Met Ser
1               5                   10                  15

<210> SEQ ID NO 21
<211> LENGTH: 10
<212> TYPE: PRT
<213> ORGANISM: Artificial
<220> FEATURE:
<223> OTHER INFORMATION: CDR sequence

<400> SEQUENCE: 21

Tyr Asp Gly Tyr Tyr Gly Trp Phe Ala Tyr
1               5                   10

<210> SEQ ID NO 22
<211> LENGTH: 11
<212> TYPE: PRT
```

<213> ORGANISM: Artificial
<220> FEATURE:
<223> OTHER INFORMATION: CDR sequence

<400> SEQUENCE: 22

Arg Ala Ser Gln Asp Ile Ser Tyr Tyr Leu Asn
1               5                   10

<210> SEQ ID NO 23
<211> LENGTH: 7
<212> TYPE: PRT
<213> ORGANISM: Artificial
<220> FEATURE:
<223> OTHER INFORMATION: CDR sequence

<400> SEQUENCE: 23

Tyr Thr Ser Arg Leu His Ser
1               5

<210> SEQ ID NO 24
<211> LENGTH: 9
<212> TYPE: PRT
<213> ORGANISM: Artificial
<220> FEATURE:
<223> OTHER INFORMATION: CDR sequence

<400> SEQUENCE: 24

Gln Gln Gly His Thr Leu Pro Trp Thr
1               5

<210> SEQ ID NO 25
<211> LENGTH: 10
<212> TYPE: PRT
<213> ORGANISM: Artificial
<220> FEATURE:
<223> OTHER INFORMATION: CDR sequence

<400> SEQUENCE: 25

Gly Phe Ser Leu Thr Ser Tyr Gly Val Leu
1               5                   10

<210> SEQ ID NO 26
<211> LENGTH: 5
<212> TYPE: PRT
<213> ORGANISM: Artificial
<220> FEATURE:
<223> OTHER INFORMATION: CDR sequence

<400> SEQUENCE: 26

Trp Ser Gly Gly Ser
1               5

<210> SEQ ID NO 27
<211> LENGTH: 5
<212> TYPE: PRT
<213> ORGANISM: Artificial
<220> FEATURE:
<223> OTHER INFORMATION: CDR sequence

<400> SEQUENCE: 27

Glu Glu Phe Gly Tyr
1               5

<210> SEQ ID NO 28
<211> LENGTH: 11
<212> TYPE: PRT
<213> ORGANISM: Artificial

```
<220> FEATURE:
<223> OTHER INFORMATION: CDR sequence

<400> SEQUENCE: 28

Arg Ala Ser Gln Asp Ile Asn Asn Tyr Leu Asn
1               5                   10

<210> SEQ ID NO 29
<211> LENGTH: 7
<212> TYPE: PRT
<213> ORGANISM: Artificial
<220> FEATURE:
<223> OTHER INFORMATION: CDR sequence

<400> SEQUENCE: 29

Tyr Thr Ser Arg Leu His Ser
1               5

<210> SEQ ID NO 30
<211> LENGTH: 9
<212> TYPE: PRT
<213> ORGANISM: Artificial
<220> FEATURE:
<223> OTHER INFORMATION: CDR sequence

<400> SEQUENCE: 30

Gln Gln Thr Asn Thr Leu Pro Trp Thr
1               5

<210> SEQ ID NO 31
<211> LENGTH: 10
<212> TYPE: PRT
<213> ORGANISM: Artificial
<220> FEATURE:
<223> OTHER INFORMATION: CDR sequence

<400> SEQUENCE: 31

Gly Tyr Thr Phe Thr Asp Tyr Asn Met Asp
1               5                   10

<210> SEQ ID NO 32
<211> LENGTH: 6
<212> TYPE: PRT
<213> ORGANISM: Artificial
<220> FEATURE:
<223> OTHER INFORMATION: CDR sequence

<400> SEQUENCE: 32

Asn Pro Asn Tyr Asp Ser
1               5

<210> SEQ ID NO 33
<211> LENGTH: 12
<212> TYPE: PRT
<213> ORGANISM: Artificial
<220> FEATURE:
<223> OTHER INFORMATION: CDR sequence

<400> SEQUENCE: 33

Gly Gly Tyr Gly Asn Tyr Val Asp Tyr Phe Asp Tyr
1               5                   10

<210> SEQ ID NO 34
<211> LENGTH: 11
<212> TYPE: PRT
<213> ORGANISM: Artificial
<220> FEATURE:
```

```
<223> OTHER INFORMATION: CDR sequence

<400> SEQUENCE: 34

Lys Ala Ser Glu Asn Val Val Thr Tyr Val Ser
1               5                   10

<210> SEQ ID NO 35
<211> LENGTH: 7
<212> TYPE: PRT
<213> ORGANISM: Artificial
<220> FEATURE:
<223> OTHER INFORMATION: CDR sequence

<400> SEQUENCE: 35

Gly Ala Ser Asn Arg Tyr Thr
1               5

<210> SEQ ID NO 36
<211> LENGTH: 9
<212> TYPE: PRT
<213> ORGANISM: Artificial
<220> FEATURE:
<223> OTHER INFORMATION: CDR sequence

<400> SEQUENCE: 36

Gly Gln Ser Tyr Ser Tyr Pro Tyr Thr
1               5

<210> SEQ ID NO 37
<211> LENGTH: 10
<212> TYPE: PRT
<213> ORGANISM: Artificial
<220> FEATURE:
<223> OTHER INFORMATION: CDR sequence

<400> SEQUENCE: 37

Gly Tyr Ser Phe Thr Ser Tyr Trp Met His
1               5                   10

<210> SEQ ID NO 38
<211> LENGTH: 6
<212> TYPE: PRT
<213> ORGANISM: Artificial
<220> FEATURE:
<223> OTHER INFORMATION: CDR sequence

<400> SEQUENCE: 38

Tyr Pro Gly Asn Ser Asp
1               5

<210> SEQ ID NO 39
<211> LENGTH: 13
<212> TYPE: PRT
<213> ORGANISM: Artificial
<220> FEATURE:
<223> OTHER INFORMATION: CDR sequence

<400> SEQUENCE: 39

Phe Tyr Tyr Arg Tyr Glu Asp Tyr Tyr Ala Met Asp Tyr
1               5                   10

<210> SEQ ID NO 40
<211> LENGTH: 11
<212> TYPE: PRT
<213> ORGANISM: Artificial
<220> FEATURE:
<223> OTHER INFORMATION: CDR sequence
```

<400> SEQUENCE: 40

Lys Ala Ser Gln Asp Val Asn Thr Ala Val Ala
1               5                   10

<210> SEQ ID NO 41
<211> LENGTH: 7
<212> TYPE: PRT
<213> ORGANISM: Artificial
<220> FEATURE:
<223> OTHER INFORMATION: CDR sequence

<400> SEQUENCE: 41

Ser Ala Ser Tyr Arg Tyr Thr
1               5

<210> SEQ ID NO 42
<211> LENGTH: 9
<212> TYPE: PRT
<213> ORGANISM: Artificial
<220> FEATURE:
<223> OTHER INFORMATION: CDR sequence

<400> SEQUENCE: 42

Gln Gln His Tyr Ser Thr Pro Phe Thr
1               5

<210> SEQ ID NO 43
<211> LENGTH: 10
<212> TYPE: PRT
<213> ORGANISM: Artificial
<220> FEATURE:
<223> OTHER INFORMATION: CDR sequence

<400> SEQUENCE: 43

Gly Phe Ser Leu Thr Ser Tyr Gly Val His
1               5                   10

<210> SEQ ID NO 44
<211> LENGTH: 5
<212> TYPE: PRT
<213> ORGANISM: Artificial
<220> FEATURE:
<223> OTHER INFORMATION: CDR sequence

<400> SEQUENCE: 44

Trp Ala Gly Gly Asn
1               5

<210> SEQ ID NO 45
<211> LENGTH: 10
<212> TYPE: PRT
<213> ORGANISM: Artificial
<220> FEATURE:
<223> OTHER INFORMATION: CDR sequence

<400> SEQUENCE: 45

Tyr Asp Gly Tyr Tyr Gly Trp Phe Ala Tyr
1               5                   10

<210> SEQ ID NO 46
<211> LENGTH: 11
<212> TYPE: PRT
<213> ORGANISM: Artificial
<220> FEATURE:
<223> OTHER INFORMATION: CDR sequence

```
<400> SEQUENCE: 46

Arg Ala Ser Gln Asp Ile Ser Tyr Tyr Leu Asn
1               5                   10

<210> SEQ ID NO 47
<211> LENGTH: 7
<212> TYPE: PRT
<213> ORGANISM: Artificial
<220> FEATURE:
<223> OTHER INFORMATION: CDR sequence

<400> SEQUENCE: 47

Tyr Thr Ser Arg Leu His Ser
1               5

<210> SEQ ID NO 48
<211> LENGTH: 9
<212> TYPE: PRT
<213> ORGANISM: Artificial
<220> FEATURE:
<223> OTHER INFORMATION: CDR sequence

<400> SEQUENCE: 48

Gln Gln Gly His Thr Leu Pro Trp Thr
1               5

<210> SEQ ID NO 49
<211> LENGTH: 277
<212> TYPE: PRT
<213> ORGANISM: Homo sapiens
<220> FEATURE:
<223> OTHER INFORMATION: OX40

<400> SEQUENCE: 49

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
                20                  25                  30

Gly Asp Thr Tyr Pro Ser Asn Asp Arg Cys Cys His Glu Cys Arg Pro
            35                  40                  45

Gly Asn Gly Met Val Ser Arg Cys Ser Arg Ser Gln Asn Thr Val Cys
        50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205
```

-continued

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 50
<211> LENGTH: 272
<212> TYPE: PRT
<213> ORGANISM: Mus musculus
<220> FEATURE:
<223> OTHER INFORMATION: OX40

<400> SEQUENCE: 50

Met Tyr Val Trp Val Gln Gln Pro Thr Ala Leu Leu Leu Leu Gly Leu
1               5                   10                  15

Thr Leu Gly Val Thr Ala Arg Arg Leu Asn Cys Val Lys His Thr Tyr
            20                  25                  30

Pro Ser Gly His Lys Cys Cys Arg Glu Cys Gln Pro Gly His Gly Met
        35                  40                  45

Val Ser Arg Cys Asp His Thr Arg Asp Thr Leu Cys His Pro Cys Glu
    50                  55                  60

Thr Gly Phe Tyr Asn Glu Ala Val Asn Tyr Asp Thr Cys Lys Gln Cys
65                  70                  75                  80

Thr Gln Cys Asn His Arg Ser Gly Ser Glu Leu Lys Gln Asn Cys Thr
                85                  90                  95

Pro Thr Gln Asp Thr Val Cys Arg Cys Arg Pro Gly Thr Gln Pro Arg
            100                 105                 110

Gln Asp Ser Gly Tyr Lys Leu Gly Val Asp Cys Val Pro Cys Pro Pro
        115                 120                 125

Gly His Phe Ser Pro Gly Asn Asn Gln Ala Cys Lys Pro Trp Thr Asn
    130                 135                 140

Cys Thr Leu Ser Gly Lys Gln Thr Arg His Pro Ala Ser Asp Ser Leu
145                 150                 155                 160

Asp Ala Val Cys Glu Asp Arg Ser Leu Leu Ala Thr Leu Leu Trp Glu
                165                 170                 175

Thr Gln Arg Pro Thr Phe Arg Pro Thr Thr Val Gln Ser Thr Thr Val
            180                 185                 190

Trp Pro Arg Thr Ser Glu Leu Pro Ser Pro Pro Thr Leu Val Thr Pro
        195                 200                 205

Glu Gly Pro Ala Phe Ala Val Leu Leu Gly Leu Gly Leu Gly Leu Leu
    210                 215                 220

Ala Pro Leu Thr Val Leu Leu Ala Leu Tyr Leu Leu Arg Lys Ala Trp
225                 230                 235                 240

Arg Leu Pro Asn Thr Pro Lys Pro Cys Trp Gly Asn Ser Phe Arg Thr
                245                 250                 255

Pro Ile Gln Glu Glu His Thr Asp Ala His Phe Thr Leu Ala Lys Ile
            260                 265                 270

<210> SEQ ID NO 51

<211> LENGTH: 277
<212> TYPE: PRT
<213> ORGANISM: Macaca fascicularis
<220> FEATURE:
<223> OTHER INFORMATION: OX40

<400> SEQUENCE: 51

Met Cys Val Gly Ala Arg Arg Leu Gly Arg Gly Pro Cys Ala Ala Leu
1               5                   10                  15

Leu Leu Leu Gly Leu Gly Leu Ser Thr Thr Ala Lys Leu His Cys Val
            20                  25                  30

Gly Asp Thr Tyr Pro Ser Asn Asp Arg Cys Cys Gln Glu Cys Arg Pro
        35                  40                  45

Gly Asn Gly Met Val Ser Arg Cys Asn Arg Ser Gln Asn Thr Val Cys
    50                  55                  60

Arg Pro Cys Gly Pro Gly Phe Tyr Asn Asp Val Val Ser Ala Lys Pro
65                  70                  75                  80

Cys Lys Ala Cys Thr Trp Cys Asn Leu Arg Ser Gly Ser Glu Arg Lys
                85                  90                  95

Gln Pro Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
    130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Thr Gln Pro
                165                 170                 175

Gln Glu Thr Gln Gly Pro Pro Ala Arg Pro Thr Thr Val Gln Pro Thr
            180                 185                 190

Glu Ala Trp Pro Arg Thr Ser Gln Arg Pro Ser Thr Arg Pro Val Glu
        195                 200                 205

Val Pro Arg Gly Pro Ala Val Ala Ala Ile Leu Gly Leu Gly Leu Ala
    210                 215                 220

Leu Gly Leu Leu Gly Pro Leu Ala Met Leu Leu Ala Leu Leu Leu Leu
225                 230                 235                 240

Arg Arg Asp Gln Arg Leu Pro Pro Asp Ala Pro Lys Ala Pro Gly Gly
                245                 250                 255

Gly Ser Phe Arg Thr Pro Ile Gln Glu Glu Gln Ala Asp Ala His Ser
            260                 265                 270

Ala Leu Ala Lys Ile
        275

<210> SEQ ID NO 52
<211> LENGTH: 270
<212> TYPE: PRT
<213> ORGANISM: Artificial
<220> FEATURE:
<223> OTHER INFORMATION: Chimeric OX40

<400> SEQUENCE: 52

Met Tyr Val Trp Val Gln Gln Pro Thr Ala Leu Leu Leu Leu Gly Leu
1               5                   10                  15

Thr Leu Gly Val Thr Ala Arg Arg Leu Asn Cys Val Lys His Thr Tyr
            20                  25                  30

Pro Ser Asn Asp Arg Cys Cys His Glu Cys Arg Pro Gly Asn Gly Met

```
                35                  40                  45
Val Ser Arg Cys Ser Arg Ser Gln Asn Thr Val Cys Arg Pro Cys Gly
 50                  55                  60

Pro Gly Phe Tyr Asn Asp Val Val Ser Ser Lys Pro Cys Lys Pro Cys
 65                  70                  75                  80

Thr Trp Cys Asn Leu Arg Ser Gly Ser Glu Arg Lys Gln Leu Cys Thr
                 85                  90                  95

Ala Thr Gln Asp Thr Val Cys Arg Cys Arg Ala Gly Thr Gln Pro Leu
                100                 105                 110

Asp Ser Tyr Lys Pro Gly Val Asp Cys Ala Pro Cys Pro Pro Gly His
                115                 120                 125

Phe Ser Pro Gly Asp Asn Gln Ala Cys Lys Pro Trp Thr Asn Cys Thr
                130                 135                 140

Leu Ala Gly Lys His Thr Leu Gln Pro Ala Ser Asn Ser Ser Asp Ala
145                 150                 155                 160

Ile Cys Glu Asp Arg Asp Pro Pro Ala Thr Gln Pro Gln Glu Thr Gln
                165                 170                 175

Gly Pro Pro Ala Arg Pro Ile Thr Val Gln Pro Thr Glu Ala Trp Pro
                180                 185                 190

Arg Thr Ser Glu Leu Pro Ser Pro Pro Thr Leu Val Thr Pro Glu Gly
                195                 200                 205

Pro Ala Phe Ala Val Leu Leu Gly Leu Gly Leu Gly Leu Leu Ala Pro
                210                 215                 220

Leu Thr Val Leu Leu Ala Leu Tyr Leu Leu Arg Lys Ala Trp Arg Leu
225                 230                 235                 240

Pro Asn Thr Pro Lys Pro Cys Trp Gly Asn Ser Phe Arg Thr Pro Ile
                245                 250                 255

Gln Glu Glu His Thr Asp Ala His Phe Thr Leu Ala Lys Ile
                260                 265                 270

<210> SEQ ID NO 53
<211> LENGTH: 113
<212> TYPE: PRT
<213> ORGANISM: Artificial
<220> FEATURE:
<223> OTHER INFORMATION: Humanized heavy chain variable domain (VH)

<400> SEQUENCE: 53

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Ser Leu Thr Ser Tyr
                20                  25                  30

Gly Val Leu Trp Val Arg Gln Ala Pro Gly Lys Gly Leu Glu Trp Val
                35                  40                  45

Ala Val Ile Trp Ser Gly Gly Ser Thr Asp Tyr Asn Ala Ala Phe Ile
 50                  55                  60

Ser Arg Leu Thr Ile Ser Arg Asp Asn Ser Lys Ser Thr Leu Tyr Phe
 65                  70                  75                  80

Gln Met Asn Ser Leu Arg Ala Glu Asp Thr Ala Val Tyr Tyr Cys Ala
                 85                  90                  95

Arg Glu Glu Phe Gly Tyr Trp Gly Gln Gly Thr Leu Val Thr Val Ser
                100                 105                 110

Ser

<210> SEQ ID NO 54
```

```
<211> LENGTH: 113
<212> TYPE: PRT
<213> ORGANISM: Artificial
<220> FEATURE:
<223> OTHER INFORMATION: Humanized VH

<400> SEQUENCE: 54

Gln Val Gln Leu Val Glu Ser Gly Gly Gly Val Val Gln Pro Gly Arg
1               5                   10                  15

Ser Leu Arg Ile Ser Cys Ala Val Ser Gly Phe Ser Leu Thr Ser Tyr
            20                  25                  30

Gly Val Leu Trp Val Arg Gln Ala Pro Gly Lys Gly Leu Glu Trp Val
        35                  40                  45

Ala Val Ile Trp Ser Gly Gly Ser Thr Asp Tyr Asn Ala Ala Phe Ile
    50                  55                  60

Ser Arg Leu Thr Ile Ser Arg Asp Asn Ser Lys Ser Thr Val Tyr Phe
65                  70                  75                  80

Gln Met Asn Ser Leu Arg Ala Glu Asp Thr Ala Val Tyr Tyr Cys Ala
                85                  90                  95

Arg Glu Glu Phe Gly Tyr Trp Gly Gln Gly Thr Leu Val Thr Val Ser
            100                 105                 110

Ser

<210> SEQ ID NO 55
<211> LENGTH: 113
<212> TYPE: PRT
<213> ORGANISM: Artificial
<220> FEATURE:
<223> OTHER INFORMATION: Humanized VH

<400> SEQUENCE: 55

Gln Val Gln Leu Val Glu Ser Gly Gly Gly Val Val Gln Pro Gly Arg
1               5                   10                  15

Ser Leu Arg Ile Ser Cys Ala Val Ser Gly Phe Ser Leu Thr Ser Tyr
            20                  25                  30

Gly Val Leu Trp Val Arg Gln Ala Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Thr Ile Ser Arg Asp Asn Ser Lys Ser Thr Val Tyr Phe
65                  70                  75                  80

Gln Met Asn Ser Leu Arg Ala Glu Asp Thr Ala Val Tyr Tyr Cys Ala
                85                  90                  95

Arg Glu Glu Phe Gly Tyr Trp Gly Gln Gly Thr Leu Val Thr Val Ser
            100                 105                 110

Ser

<210> SEQ ID NO 56
<211> LENGTH: 108
<212> TYPE: PRT
<213> ORGANISM: Artificial
<220> FEATURE:
<223> OTHER INFORMATION: Humanized light chain variable domain (VL)

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
            20                  25                  30
```

```
Leu Asn Trp Tyr Gln Gln Lys Pro Gly Gly Ala Val Lys Leu Leu Ile
        35                  40                  45

Tyr Tyr Thr Ser Arg Leu His Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Thr Asn Thr Leu Pro Trp
                85                  90                  95

Thr Phe Gly Gly Gly Thr Lys Leu Glu Val Lys Arg
            100                 105

<210> SEQ ID NO 57
<211> LENGTH: 108
<212> TYPE: PRT
<213> ORGANISM: Artificial
<220> FEATURE:
<223> OTHER INFORMATION: Humanized VL

<400> SEQUENCE: 57

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
                20                  25                  30

Leu Asn Trp Tyr Gln Gln Lys Pro Gly Gly Ala Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ile Ala Thr Tyr Tyr Cys Gln Gln Thr Asn Thr Leu Pro Trp
                85                  90                  95

Thr Phe Gly Gly Gly Thr Lys Leu Glu Ile Lys Arg
            100                 105

<210> SEQ ID NO 58
<211> LENGTH: 108
<212> TYPE: PRT
<213> ORGANISM: Artificial
<220> FEATURE:
<223> OTHER INFORMATION: Humanized VL

<400> SEQUENCE: 58

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Asn Asn Tyr
                20                  25                  30

Leu Asn Trp Tyr Gln Gln Lys Pro Gly Gly Ala Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Phe Cys Gln Gln Thr Asn Thr Leu Pro Trp
                85                  90                  95

Thr Phe Gly Gly Gly Thr Lys Leu Glu Ile Lys Arg
            100                 105
```

-continued

```
<210> SEQ ID NO 59
<211> LENGTH: 121
<212> TYPE: PRT
<213> ORGANISM: Artificial
<220> FEATURE:
<223> OTHER INFORMATION: Humanized VH

<400> SEQUENCE: 59

Glu Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Asn Met Asp Trp Val Arg Gln Ala Pro Gly Lys Gly Leu Glu Trp Ile
            35                  40                  45

Gly Asp Ile Asn Pro Asn Tyr Asp Ser Thr Ser Tyr Asn Gln Lys Phe
    50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Gly Asn Tyr Val Asp Tyr Phe Asp Tyr Trp Gly
            100                 105                 110

Gln Gly Thr Leu Val Thr Val Ser Ser
        115                 120

<210> SEQ ID NO 60
<211> LENGTH: 121
<212> TYPE: PRT
<213> ORGANISM: Artificial
<220> FEATURE:
<223> OTHER INFORMATION: Humanized VH

<400> SEQUENCE: 60

Glu Val Gln Leu Gln Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Asn Met Asp Trp Val Lys Gln Ala Pro Gly Lys Gly Leu Glu Trp Ile
            35                  40                  45

Gly Asp Ile Asn Pro Asn Tyr Asp Ser Thr Ser Tyr Asn Gln Lys Phe
    50                  55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Gly Asn Tyr Val Asp Tyr Phe Asp Tyr Trp Gly
            100                 105                 110

Gln Gly Thr Leu Val Thr Val Ser Ser
        115                 120

<210> SEQ ID NO 61
<211> LENGTH: 121
<212> TYPE: PRT
<213> ORGANISM: Artificial
<220> FEATURE:
<223> OTHER INFORMATION: Humanized VH

<400> SEQUENCE: 61

Glu Val Gln Leu Gln Gln Ser Gly Ala Glu Val Val Lys Pro Gly Ala
1               5                   10                  15
```

```
Ser Val Lys Ile Ser Cys Lys Ala Ser Gly Tyr Thr Phe Thr Asp Tyr
            20                  25                  30

Asn Met Asp Trp Val Lys Gln Ala Pro Gly Lys Gly Leu Glu Trp Ile
        35                  40                  45

Gly Asp Ile Asn Pro Asn Tyr Asp Ser Thr Ser Tyr Asn Gln Lys Phe
50                      55                  60

Lys Gly Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Tyr Gly Asn Tyr Val Asp Tyr Phe Asp Tyr Trp Gly
            100                 105                 110

Gln Gly Thr Leu Leu Thr Val Ser Ser
            115                 120

<210> SEQ ID NO 62
<211> LENGTH: 107
<212> TYPE: PRT
<213> ORGANISM: Artificial
<220> FEATURE:
<223> OTHER INFORMATION: Humanized VL

<400> SEQUENCE: 62

Glu Ile Val Met Thr Gln Ser Pro Ala Thr Leu Ser Leu Ser Pro Gly
1               5                   10                  15

Glu Arg Ala Thr Leu Ser Cys Lys Ala Ser Glu Asn Val Val Thr Tyr
            20                  25                  30

Val Ser Trp Tyr Gln Gln Lys Pro Gly Gln Ala Pro Arg Leu Leu Ile
        35                  40                  45

Tyr Gly Ala Ser Asn Arg Tyr Thr Gly Ile Pro Ala Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Asp Tyr His Cys Gly Gln Ser Tyr Ser Tyr Pro Tyr
                85                  90                  95

Thr Phe Gly Gln Gly Thr Lys Leu Glu Ile Lys
            100                 105

<210> SEQ ID NO 63
<211> LENGTH: 107
<212> TYPE: PRT
<213> ORGANISM: Artificial
<220> FEATURE:
<223> OTHER INFORMATION: Humanized VL

<400> SEQUENCE: 63

Asn Ile Val Met Thr Gln Ser Pro Ala Thr Leu Ser Leu Ser Pro Gly
1               5                   10                  15

Glu Arg Ala Thr Leu Ser Cys Lys Ala Ser Glu Asn Val Val Thr Tyr
            20                  25                  30

Val Ser Trp Tyr Gln Gln Lys Pro Gly Gln Ala Pro Arg Leu Leu Ile
        35                  40                  45

Tyr Gly Ala Ser Asn Arg Tyr Thr Gly Ile Pro Ala Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Asp Tyr His Cys Gly Gln Ser Tyr Ser Tyr Pro Tyr
```

-continued

```
                85                  90                  95
Thr Phe Gly Gln Gly Thr Lys Leu Glu Ile Lys
                100                 105

<210> SEQ ID NO 64
<211> LENGTH: 107
<212> TYPE: PRT
<213> ORGANISM: Artificial
<220> FEATURE:
<223> OTHER INFORMATION: Humanized VL

<400> SEQUENCE: 64

Asn Ile Val Met Thr Gln Ser Pro Ala Thr Leu Ser Leu Ser Pro Gly
1               5                   10                  15

Glu Arg Ala Thr Leu Ser Cys Lys Ala Ser Glu Asn Val Val Thr Tyr
            20                  25                  30

Val Ser Trp Tyr Gln Gln Lys Pro Gly Gln Ala Pro Arg Leu Leu Ile
        35                  40                  45

Tyr Gly Ala Ser Asn Arg Tyr Thr Gly Val Pro Asp Arg Phe Ser Gly
    50                  55                  60

Ser Gly Ser Ala Thr Asp Phe Thr Leu Thr Ile Ser Ser Val Gln Pro
65                  70                  75                  80

Glu Asp Phe Ala Asp Tyr His Cys Gly Gln Ser Tyr Ser Tyr Pro Tyr
                85                  90                  95

Thr Phe Gly Gln Gly Thr Lys Leu Glu Ile Lys
                100                 105

<210> SEQ ID NO 65
<211> LENGTH: 107
<212> TYPE: PRT
<213> ORGANISM: Artificial
<220> FEATURE:
<223> OTHER INFORMATION: Humanized VL

<400> SEQUENCE: 65

Asn Ile Val Met Thr Gln Ser Pro Ala Thr Leu Ser Leu Ser Pro Gly
1               5                   10                  15

Glu Arg Ala Thr Leu Ser Cys Lys Ala Ser Glu Asn Val Val Thr Tyr
            20                  25                  30

Val Ser Trp Tyr Gln Gln Lys Pro Gly Gln Ser Pro Arg Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Pro
65                  70                  75                  80

Glu Asp Phe Ala Asp Tyr His Cys Gly Gln Ser Tyr Ser Tyr Pro Tyr
                85                  90                  95

Thr Phe Gly Gln Gly Thr Lys Leu Glu Ile Lys
                100                 105

<210> SEQ ID NO 66
<211> LENGTH: 122
<212> TYPE: PRT
<213> ORGANISM: Artificial
<220> FEATURE:
<223> OTHER INFORMATION: Humanized VH

<400> SEQUENCE: 66

Gln Val Gln Leu Val Gln Ser Gly Ala Glu Val Lys Lys Pro Gly Ala
1               5                   10                  15
```

Ser Val Lys Met Ser Cys Lys Ala Ser Gly Tyr Ser Phe Thr Ser Tyr
            20                  25                  30

Trp Met His Trp Val Arg Gln Arg Pro Gly Gln Gly Leu Glu Trp Ile
            35                  40                  45

Gly Thr Ile Tyr Pro Gly Asn Ser Asp Thr Ser Asn Asn Gln Lys Phe
        50                  55                  60

Lys Gly Arg Val Lys Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Thr Phe Tyr Tyr Arg Tyr Glu Asp Tyr Tyr Ala Met Asp Tyr Trp
            100                 105                 110

Gly Gln Gly Thr Leu Val Thr Val Ser Ser
            115                 120

<210> SEQ ID NO 67
<211> LENGTH: 122
<212> TYPE: PRT
<213> ORGANISM: Artificial
<220> FEATURE:
<223> OTHER INFORMATION: Humanized VH

<400> SEQUENCE: 67

Glu Val Gln Leu Val Gln Ser Gly Ala Glu Val Lys Lys Pro Gly Ala
1               5                   10                  15

Ser Val Lys Met Ser Cys Lys Ala Ser Gly Tyr Ser Phe Thr Ser Tyr
            20                  25                  30

Trp Met His Trp Val Arg Gln Arg Pro Gly Gln Gly Leu Glu Trp Ile
            35                  40                  45

Gly Thr Ile Tyr Pro Gly Asn Ser Asp Thr Ser Asn Asn Gln Lys Phe
        50                  55                  60

Lys Gly Arg Val Lys Leu Thr Ala Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Thr Phe Tyr Tyr Arg Tyr Glu Asp Tyr Tyr Ala Met Asp Tyr Trp
            100                 105                 110

Gly Gln Gly Thr Leu Val Thr Val Ser Ser
            115                 120

<210> SEQ ID NO 68
<211> LENGTH: 122
<212> TYPE: PRT
<213> ORGANISM: Artificial
<220> FEATURE:
<223> OTHER INFORMATION: Humanized VH

<400> SEQUENCE: 68

Glu Val Gln Leu Val Gln Ser Gly Ala Glu Val Lys Lys Pro Gly Ala
1               5                   10                  15

Ser Val Lys Met Ser Cys Lys Ala Ser Gly Tyr Ser Phe Thr Ser Tyr
            20                  25                  30

Trp Met His Trp Val Arg Gln Arg Pro Gly Gln Gly Leu Glu Trp Ile
            35                  40                  45

Gly Thr Ile Tyr Pro Gly Asn Ser Asp Thr Ser Asn Asn Gln Lys Phe
        50                  55                  60

Lys Gly Arg Ala Lys Leu Thr Ala Asp Thr Ser Ala Ser Thr Ala Tyr

```
                65                  70                  75                  80
Met Glu Leu Ser Ser Leu Arg Ser Glu Asp Thr Ala Val Tyr Tyr Cys
                    85                  90                  95

Thr Thr Phe Tyr Tyr Arg Tyr Glu Asp Tyr Tyr Ala Met Asp Tyr Trp
                100                 105                 110

Gly Gln Gly Thr Leu Val Thr Val Ser Ser
            115                 120

<210> SEQ ID NO 69
<211> LENGTH: 107
<212> TYPE: PRT
<213> ORGANISM: Artificial
<220> FEATURE:
<223> OTHER INFORMATION: Humanized VL

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asn Ser Ala
                20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Phe Ala Val Tyr Tyr Cys Gln Gln His Tyr Ser Thr Pro Phe
                85                  90                  95

Thr Phe Gly Gln Gly Thr Lys Leu Glu Ile Lys
            100                 105

<210> SEQ ID NO 70
<211> LENGTH: 107
<212> TYPE: PRT
<213> ORGANISM: Artificial
<220> FEATURE:
<223> OTHER INFORMATION: Humanized VL

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Phe Ala Val Tyr Tyr Cys Gln Gln His Tyr Ser Thr Pro Phe
                85                  90                  95

Thr Phe Gly Gln Gly Thr Lys Leu Glu Ile Lys
            100                 105

<210> SEQ ID NO 71
<211> LENGTH: 107
<212> TYPE: PRT
<213> ORGANISM: Artificial
<220> FEATURE:
```

<223> OTHER INFORMATION: Humanized VL

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asn Thr Ala
            20                  25                  30

Val Ala Trp Tyr Gln Gln Lys Pro Gly Lys Ser Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Val Tyr Tyr Cys Gln Gln His Tyr Ser Thr Pro Phe
                85                  90                  95

Thr Phe Gly Gln Gly Thr Lys Leu Glu Ile Lys
            100                 105

<210> SEQ ID NO 72
<211> LENGTH: 107
<212> TYPE: PRT
<213> ORGANISM: Artificial
<220> FEATURE:
<223> OTHER INFORMATION: Humanized VL

<400> SEQUENCE: 72

Asp Ile Val Met Thr Gln Ser Pro Ser Ser Met Ser Ala Ser Val Gly
1               5                   10                  15

Asp Arg Val Thr Ile Thr Cys Lys Ala Ser Gln Asp Val Asn Thr Ala
            20                  25                  30

Val Ala Trp Tyr Gln Gln Lys Pro Gly Lys Ser Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Phe Thr Ile Ser Ser Val Gln Pro
65                  70                  75                  80

Glu Asp Phe Ala Val Tyr Tyr Cys Gln Gln His Tyr Ser Thr Pro Phe
                85                  90                  95

Thr Phe Gly Gln Gly Thr Lys Leu Glu Ile Lys
            100                 105

<210> SEQ ID NO 73
<211> LENGTH: 118
<212> TYPE: PRT
<213> ORGANISM: Artificial
<220> FEATURE:
<223> OTHER INFORMATION: Humanized VH

<400> SEQUENCE: 73

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ser Tyr
            20                  25                  30

Gly Val His Trp Ile Arg Gln Pro Pro Gly Lys Gly Leu Glu Trp Ile
        35                  40                  45

Gly Val Ile Trp Ala Gly Gly Asn Thr Asn Tyr Asn Ser Ala Leu Met
    50                  55                  60

Ser Arg Leu Thr Ile Ser Lys Asp Thr Ser Lys Asn Gln Val Ser Leu

```
                65                  70                  75                  80
Lys Met Ser Ser Val Thr Ala Ala Asp Thr Ala Val Tyr Tyr Cys Ala
                    85                  90                  95

Ser Tyr Asp Gly Tyr Tyr Gly Trp Phe Ala Tyr Trp Gly Gln Gly Thr
                100                 105                 110

Leu Val Thr Val Ser Val
            115

<210> SEQ ID NO 74
<211> LENGTH: 118
<212> TYPE: PRT
<213> ORGANISM: Artificial
<220> FEATURE:
<223> OTHER INFORMATION: Humanized VH

<400> SEQUENCE: 74

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Ser Tyr
                20                  25                  30

Gly Val His Trp Ile Arg Gln Pro Pro Gly Lys Gly Leu Glu Trp Leu
            35                  40                  45

Gly Val Ile Trp Ala Gly Gly Asn Thr Asn Tyr Asn Ser Ala Leu Met
        50                  55                  60

Ser Arg Leu Thr Ile Ser Lys Asp Asn Ser Lys Ser Gln Val Ser Leu
65                  70                  75                  80

Lys Met Ser Ser Val Thr Ala Ala Asp Thr Ala Val Tyr Tyr Cys Ala
                    85                  90                  95

Ser Tyr Asp Gly Tyr Tyr Gly Trp Phe Ala Tyr Trp Gly Gln Gly Thr
                100                 105                 110

Leu Val Thr Val Ser Val
            115

<210> SEQ ID NO 75
<211> LENGTH: 118
<212> TYPE: PRT
<213> ORGANISM: Artificial
<220> FEATURE:
<223> OTHER INFORMATION: Humanized VH

<400> SEQUENCE: 75

Gln Val Gln Leu Gln Glu Ser Gly Pro Gly Leu Val Lys Pro Ser Glu
1               5                   10                  15

Thr Leu Ser Ile Thr Cys Thr Val Ser Gly Phe Ser Leu Thr Ser Tyr
                20                  25                  30

Gly Val His Trp Ile Arg Gln Pro Pro Gly Lys Gly Leu Glu Trp Leu
            35                  40                  45

Gly Val Ile Trp Ala Gly Gly Asn Thr Asn Tyr Asn Ser Ala Leu Met
        50                  55                  60

Ser Arg Leu Thr Ile Ser Lys Asp Asn Ser Lys Ser Gln Val Ser Leu
65                  70                  75                  80

Lys Met Ser Ser Val Thr Ala Ala Asp Thr Ala Met Tyr Asn Cys Ala
                    85                  90                  95

Ser Tyr Asp Gly Tyr Tyr Gly Trp Phe Ala Tyr Trp Gly Gln Gly Thr
                100                 105                 110

Leu Val Thr Val Ser Val
            115
```

```
<210> SEQ ID NO 76
<211> LENGTH: 107
<212> TYPE: PRT
<213> ORGANISM: Artificial
<220> FEATURE:
<223> OTHER INFORMATION: Humanized VL

<400> SEQUENCE: 76

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Tyr Tyr
            20                  25                  30

Leu Asn Trp Tyr Gln Gln Lys Pro Gly Lys Ala Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly His Thr Leu Pro Trp
                85                  90                  95

Thr Phe Gly Gly Gly Thr Lys Leu Glu Ile Lys
            100                 105

<210> SEQ ID NO 77
<211> LENGTH: 107
<212> TYPE: PRT
<213> ORGANISM: Artificial
<220> FEATURE:
<223> OTHER INFORMATION: Humanized VL

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Tyr Tyr
            20                  25                  30

Leu Asn Trp Tyr Gln Gln Lys Pro Gly Gly Ala Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly His Thr Leu Pro Trp
                85                  90                  95

Thr Phe Gly Gly Gly Thr Lys Leu Glu Ile Lys
            100                 105

<210> SEQ ID NO 78
<211> LENGTH: 107
<212> TYPE: PRT
<213> ORGANISM: Artificial
<220> FEATURE:
<223> OTHER INFORMATION: Humanized VL

<400> SEQUENCE: 78

Asp Ile Gln Met Thr Gln Ser Thr Ser Ser Leu Ser Ala Ser Val Gly
1               5                   10                  15

Asp Arg Val Thr Ile Thr Cys Arg Ala Ser Gln Asp Ile Ser Tyr Tyr
            20                  25                  30

Leu Asn Trp Tyr Gln Gln Lys Pro Gly Gly Ala Val Lys Leu Leu Ile
        35                  40                  45
```

```
                35                  40                  45
Tyr Tyr Thr Ser Arg Leu His Ser Gly Val Pro Ser Arg Phe Ser Gly
 50                  55                  60

Ser Gly Ser Gly Thr Asp Tyr Thr Leu Thr Ile Ser Ser Leu Gln Gln
 65                  70                  75                  80

Glu Asp Ile Ala Thr Tyr Phe Cys Gln Gln Gly His Thr Leu Pro Trp
                 85                  90                  95

Thr Phe Gly Gly Gly Thr Lys Leu Glu Ile Lys
            100                 105

<210> SEQ ID NO 79
<211> LENGTH: 113
<212> TYPE: PRT
<213> ORGANISM: Mus musculus
<220> FEATURE:
<223> OTHER INFORMATION: VH

<400> SEQUENCE: 79

Gln Val Gln Leu Lys Gln Ser Gly Pro Gly Leu Val Gln Pro Ser Gln
 1               5                  10                  15

Ser Leu Ser Ile Thr Cys Thr Val Ser Gly Phe Ser Leu Thr Ser Tyr
                20                  25                  30

Gly Val Leu Trp Val Arg Gln Pro Pro Gly Lys Gly Leu Glu Trp Leu
            35                  40                  45

Gly Val Ile Trp Ser Gly Gly Ser Thr Asp Tyr Asn Ala Ala Phe Ile
 50                  55                  60

Ser Arg Leu Ser Ile Ser Lys Asp Asn Ser Lys Ser Gln Val Phe Phe
 65                  70                  75                  80

Lys Met Asn Ser Leu Gln Ala Asp Asp Thr Ala Ile Tyr Tyr Cys Ala
                 85                  90                  95

Arg Glu Glu Phe Gly Tyr Trp Gly Gln Gly Thr Leu Val Thr Val Ser
            100                 105                 110

Ala

<210> SEQ ID NO 80
<211> LENGTH: 107
<212> TYPE: PRT
<213> ORGANISM: Mus musculus
<220> FEATURE:
<223> OTHER INFORMATION: VL

<400> SEQUENCE: 80

Asp Ile Gln Met Thr Gln Thr Thr Ser Ser Leu Ser Ala Ser Leu Gly
 1               5                  10                  15

Asp Arg Val Thr Ile Ser Cys Arg Ala Ser Gln Asp Ile Asn Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
 50                  55                  60

Ser Gly Ser Gly Thr Asp Tyr Ser Leu Thr Ile Ser Asn Leu Glu Gln
 65                  70                  75                  80

Glu Asp Ile Ala Thr Tyr Phe Cys Gln Gln Thr Asn Thr Leu Pro Trp
                 85                  90                  95

Thr Phe Gly Gly Gly Thr Lys Leu Glu Ile Lys
            100                 105
```

-continued

```
<210> SEQ ID NO 81
<211> LENGTH: 121
<212> TYPE: PRT
<213> ORGANISM: Mus musculus
<220> FEATURE:
<223> OTHER INFORMATION: VH

<400> SEQUENCE: 81
```

Glu Val Gln Leu Gln Gln Phe Gly Ala Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Asp Ile Asn Pro Asn Tyr Asp Ser Thr Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Thr Ala Val Tyr Tyr Cys
            85                  90                  95

Ala Arg Gly Gly Tyr Gly Asn Tyr Val Asp Tyr Phe Asp Tyr Trp Gly
            100                 105                 110

Gln Gly Thr Thr Leu Thr Val Ser Ser
        115                 120

```
<210> SEQ ID NO 82
<211> LENGTH: 107
<212> TYPE: PRT
<213> ORGANISM: Mus musculus
<220> FEATURE:
<223> OTHER INFORMATION: VL

<400> SEQUENCE: 82
```

Asn Ile Val Met Thr Gln Ser Pro Lys Ser Met Ser Met Ser Val Gly
1               5                   10                  15

Glu Arg Val Thr Leu Ser Cys Lys Ala Ser Glu Asn Val Val Thr Tyr
            20                  25                  30

Val Ser Trp Tyr Gln Gln Lys Pro Glu Gln Ser Pro Lys Leu Leu Ile
        35                  40                  45

Tyr Gly Ala Ser Asn Arg Tyr Thr Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr His Cys Gly Gln Ser Tyr Ser Tyr Pro Tyr
            85                  90                  95

Thr Phe Gly Gly Gly Thr Lys Leu Glu Ile Lys
            100                 105

```
<210> SEQ ID NO 83
<211> LENGTH: 122
<212> TYPE: PRT
<213> ORGANISM: Mus musculus
<220> FEATURE:
<223> OTHER INFORMATION: VH

<400> SEQUENCE: 83
```

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Ser Phe Thr Ser Tyr
            20                  25                  30

```
Trp Met His Trp Val Lys Gln Arg Pro Gly Gln Gly Leu Glu Trp Ile
            35                  40                  45

Gly Thr Ile Tyr Pro Gly Asn Ser Asp Thr Ser Asn Asn Gln Lys Phe
        50                  55                  60

Lys Gly Lys Ala Lys Leu Thr Ala Val Thr Ser Ala Ser Thr Ala Tyr
 65                  70                  75                  80

Met Glu Leu Ser Ser Leu Thr Asn Glu Asp Ser Ala Val Tyr Tyr Cys
                85                  90                  95

Thr Thr Phe Tyr Tyr Arg Tyr Glu Asp Tyr Tyr Ala Met Asp Tyr Trp
                100                 105                 110

Gly Gln Gly Thr Ser Val Thr Val Ser Ser
            115                 120
```

<210> SEQ ID NO 84
<211> LENGTH: 107
<212> TYPE: PRT
<213> ORGANISM: Mus musculus
<220> FEATURE:
<223> OTHER INFORMATION: VL

<400> SEQUENCE: 84

```
Asp Ile Val Met Thr Gln Ser His Lys Phe Met Ser Thr Ser Val Gly
 1               5                  10                  15

Asp Arg Val Ser Ile Thr Cys Lys Ala Ser Gln Asp Val Asn Thr Ala
                20                  25                  30

Val Ala Trp Tyr Gln Gln Lys Pro Gly Gln Ser Pro Lys Leu Leu Ile
            35                  40                  45

Tyr Ser Ala Ser Tyr Arg Tyr Thr Gly Val Pro Asp Arg Phe Thr Gly
     50                 55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Phe
                85                  90                  95

Thr Phe Gly Ser Gly Thr Lys Leu Glu Ile Lys
                100                 105
```

<210> SEQ ID NO 85
<211> LENGTH: 118
<212> TYPE: PRT
<213> ORGANISM: Mus musculus
<220> FEATURE:
<223> OTHER INFORMATION: VH

<400> SEQUENCE: 85

```
Gln Val Gln Leu Lys Glu Ser Gly Pro Gly Leu Val Ala Pro Ser Gln
 1               5                  10                  15

Ser Leu Ser Ile Thr Cys Thr Val Ser Gly Phe Ser Leu Thr Ser Tyr
                20                  25                  30

Gly Val His Trp Ile Arg Gln Pro Pro Gly Lys Gly Leu Glu Trp Leu
            35                  40                  45

Gly Val Ile Trp Ala Gly Gly Asn Thr Asn Tyr Asn Ser Ala Leu Met
     50                 55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Met Tyr Asn Cys Ala
                85                  90                  95

Ser Tyr Asp Gly Tyr Tyr Gly Trp Phe Ala Tyr Trp Gly Gln Gly Thr
```

```
                     100             105              110
Leu Val Thr Val Ser Val
            115

<210> SEQ ID NO 86
<211> LENGTH: 107
<212> TYPE: PRT
<213> ORGANISM: Mus musculus
<220> FEATURE:
<223> OTHER INFORMATION: VL

<400> SEQUENCE: 86

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Tyr Tyr
            20                  25                  30

Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly His Thr Leu Pro Trp
                85                  90                  95

Thr Phe Gly Gly Gly Thr Lys Leu Glu Ile Lys
                100                 105
```

ANTI-OX40 ANTIBODIES AND USES THEREOF

CLAIM OF PRIORITY

This application is a divisional application of and claims priority to U.S. application Ser. No. 16/882,089, filed on May 22, 2020 (now U.S. Pat. No. 10,934,365), which is a continuation of and claims priority to International Application No. PCT/CN2017/112832, filed on Nov. 24, 2017. The entire contents of the foregoing are incorporated herein by reference.

TECHNICAL FIELD

This disclosure relates to anti-OX40 (TNF Receptor Superfamily Member 4, or TNFRSF4) antibodies and uses thereof.

BACKGROUND

Cancer is currently one of the diseases that have the highest human mortality. According to the World Health Organization statistical data, in 2012, the number of global cancer incidence and death cases reached 14 million and 8.2 million, respectively. In China, the newly diagnosed cancer cases are 3.07 million, and the death toll is 2.2 million.

Recent clinical and commercial success of anticancer antibodies has created great interest in antibody-based therapeutics. There is a need to develop anti-cancer antibodies for use in various antibody-based therapeutics to treat cancers.

SUMMARY

This disclosure relates to anti-OX40 antibodies, antigen-binding fragment thereof, and the uses thereof.

In one aspect, the disclosure provides antibody or antigen-binding fragments thereof that can bind to OX40 (TNF Receptor Superfamily Member 4) comprising a heavy chain variable region (VH) comprising complementarity determining regions (CDRs) 1, 2, and 3, wherein the VH CDR1 region comprises an amino acid sequence that is at least 80% identical to a selected VH CDR1 amino acid sequence, the VH CDR2 region comprises an amino acid sequence that is at least 80% identical to a selected VH CDR2 amino acid sequence, and the VH CDR3 region comprises an amino acid sequence that is at least 80% identical to a selected VH CDR3 amino acid sequence; and a light chain variable region (VL) comprising CDRs 1, 2, and 3, wherein the VL CDR1 region comprises an amino acid sequence that is at least 80% identical to a selected VL CDR1 amino acid sequence, the VL CDR2 region comprises an amino acid sequence that is at least 80% identical to a selected VL CDR2 amino acid sequence, and the VL CDR3 region comprises an amino acid sequence that is at least 80% identical to a selected VL CDR3 amino acid sequence, wherein the selected VH CDRs 1, 2, and 3 amino acid sequences and the selected VL CDRs, 1, 2, and 3 amino acid sequences are one of the following:

(1) the selected VH CDRs 1, 2, 3 amino acid sequences are set forth in SEQ ID NOs: 1, 2, 3, respectively, and the selected VL CDRs 1, 2, 3 amino acid sequences are set forth in SEQ ID NOs: 4, 5, 6, respectively;

(2) the selected VH CDRs 1, 2, 3 amino acid sequences are set forth in SEQ ID NOs: 7, 8, 9, respectively, and the selected VL CDRs 1, 2, 3 amino acid sequences are set forth in SEQ ID NOs: 10, 11, 12, respectively;

(3) the selected VH CDRs 1, 2, 3 amino acid sequences are set forth in SEQ ID NOs: 13, 14, 15, respectively, and the selected VL CDRs 1, 2, 3 amino acid sequences are set forth in SEQ ID NOs: 16, 17, 18, respectively;

(4) the selected VH CDRs 1, 2, 3 amino acid sequences are set forth in SEQ ID NOs: 19, 20, 21, respectively, and the selected VL CDRs 1, 2, 3 amino acid sequences are set forth in SEQ ID NOs: 22, 23, 24, respectively.

In some embodiments, the VH comprises CDRs 1, 2, 3 with the amino acid sequences set forth in SEQ ID NOs: 1, 2, and 3 respectively, and the VL comprises CDRs 1, 2, 3 with the amino acid sequences set forth in SEQ ID NOs: 4, 5, and 6, respectively. In some embodiments, the VH comprises CDRs 1, 2, 3 with the amino acid sequences set forth in SEQ ID NOs: 13, 14, and 15 respectively, and the VL comprises CDRs 1, 2, 3 with the amino acid sequences set forth in SEQ ID NOs: 16, 17, and 18, respectively.

In some embodiments, the antibody or antigen-binding fragment specifically binds to human OX40.

In some embodiments, the antibody or antigen-binding fragment is a humanized antibody or antigen-binding fragment thereof. In some embodiments, the antibody or antigen-binding fragment is a single-chain variable fragment (scFV).

In one aspect, the disclosure also provides nucleic acids comprising a polynucleotide encoding a polypeptide comprising:

(1) an immunoglobulin heavy chain or a fragment thereof comprising a heavy chain variable region (VH) comprising complementarity determining regions (CDRs) 1, 2, and 3 comprising the amino acid sequences set forth in SEQ ID NOs: 1, 2, and 3, respectively, and wherein the VH, when paired with a light chain variable region (VL) comprising the amino acid sequence set forth in SEQ ID NO: 56, 57, 58, or 80, binds to OX40;

(2) an immunoglobulin light chain or a fragment thereof comprising a VL comprising CDRs 1, 2, and 3 comprising the amino acid sequences set forth in SEQ ID NOs: 4, 5, and 6, respectively, and wherein the VL, when paired with a VH comprising the amino acid sequence set forth in SEQ ID NO: 53, 54, 55, or 79, binds to OX40;

(3) an immunoglobulin heavy chain or a fragment thereof comprising a heavy chain variable region (VH) comprising CDRs 1, 2, and 3 comprising the amino acid sequences set forth in SEQ ID NOs: 7, 8, and 9, respectively, and wherein the VH, when paired with a light chain variable region (VL) comprising the amino acid sequence set forth in SEQ ID NO: 62, 63, 64, 65, or 82, binds to OX40; or (4) an immunoglobulin light chain or a fragment thereof comprising a VL comprising CDRs 1, 2, and 3 comprising the amino acid sequences set forth in SEQ ID NOs: 10, 11, and 12, respectively, and wherein the VL, when paired with a VH comprising the amino acid sequence set forth in SEQ ID NO: 59, 60, 61, or 81, binds to OX40;

(5) an immunoglobulin heavy chain or a fragment thereof comprising a heavy chain variable region (VH) comprising CDRs 1, 2, and 3 comprising the amino acid sequences set forth in SEQ ID NOs: 13, 14, and 15, respectively, and wherein the VH, when paired with a light chain variable region (VL) comprising the amino acid sequence set forth in SEQ ID NOs: 69, 70, 71, 72, or 84 binds to OX40;

(6) an immunoglobulin light chain or a fragment thereof comprising a VL comprising CDRs 1, 2, and 3 comprising the amino acid sequences set forth in SEQ ID NOs: 16, 17, and 18, respectively, and wherein the VL, when paired with a VH comprising the amino acid sequence set forth in SEQ ID NOs: 66, 67, 68, or 83, binds to OX40;

(7) an immunoglobulin heavy chain or a fragment thereof comprising a heavy chain variable region (VH) comprising CDRs 1, 2, and 3 comprising the amino acid sequences set forth in SEQ ID NOs: 19, 20, and 21, respectively, and wherein the VH, when paired with a light chain variable region (VL) comprising the amino acid sequence set forth in SEQ ID NOs: 76, 77, 78, or 86, binds to OX40;

(8) an immunoglobulin light chain or a fragment thereof comprising a VL comprising CDRs 1, 2, and 3 comprising the amino acid sequences set forth in SEQ ID NOs: 22, 23, and 24, respectively, and wherein the VL, when paired with a VH comprising the amino acid sequence set forth in SEQ ID NO: 73, 74, 75, or 85, binds to OX40.

In some embodiments, the nucleic acid comprises a polynucleotide encoding a polypeptide comprising an immunoglobulin heavy chain or a fragment thereof comprising a VH comprising CDRs 1, 2, and 3 comprising the amino acid sequences set forth in SEQ ID NOs: 1, 2, and 3, respectively.

In some embodiments, the nucleic acid comprises a polynucleotide encoding a polypeptide comprising an immunoglobulin light chain or a fragment thereof comprising a VL comprising CDRs 1, 2, and 3 comprising the amino acid sequences set forth in SEQ ID NOs: 4, 5, and 6, respectively.

In some embodiments, the nucleic acid comprises a polynucleotide encoding a polypeptide comprising an immunoglobulin heavy chain or a fragment thereof comprising a VH comprising CDRs 1, 2, and 3 comprising the amino acid sequences set forth in SEQ ID NOs: 13, 14, and 15, respectively.

In some embodiments, the nucleic acid comprises a polynucleotide encoding a polypeptide comprising an immunoglobulin light chain or a fragment thereof comprising a VL comprising CDRs 1, 2, and 3 comprising the amino acid sequences set forth in SEQ ID NOs: 16, 17, and 18, respectively.

In some embodiments, the VH when paired with a VL specifically binds to human OX40, or the VL when paired with a VH specifically binds to human OX40.

In some embodiments, the immunoglobulin heavy chain or the fragment thereof is a humanized immunoglobulin heavy chain or a fragment thereof, and the immunoglobulin light chain or the fragment thereof is a humanized immunoglobulin light chain or a fragment thereof.

In some embodiments, the nucleic acid encodes a single-chain variable fragment (scFv). In some embodiments, the nucleic acid is cDNA.

In one aspect, the disclosure also provides vectors comprising one or more of the nucleic acids as described herein. In some embodiments, the vector encodes the VL region and the VH region that together bind to OX40.

In one aspect, the disclosure relates to a pair of vectors, wherein each vector comprises one of the nucleic acids as described herein, wherein together the pair of vectors encodes the VL region and the VH region that together bind to OX40.

In another aspect, the disclosure also provides a cell comprising the vector or the pair of vectors as described herein. In some embodiments, the cell is a CHO cell.

In one aspect, the disclosure also relates to cells comprising one or more of the nucleic acids as described herein, or cells comprising two of the nucleic acids as described herein. In some embodiments, the two nucleic acids together encode the VL region and the VH region that together bind to OX40.

In another aspect, the disclosure relates to methods of producing an antibody or an antigen-binding fragment thereof. The methods involve culturing the cell as described herein under conditions sufficient for the cell to produce the antibody or the antigen-binding fragment; and collecting the antibody or the antigen-binding fragment produced by the cell.

In one aspect, the disclosure relates to antibodies or antigen-binding fragments thereof that bind to OX40 comprising a heavy chain variable region (VH) comprising an amino acid sequence that is at least 90% identical to a selected VH sequence, and a light chain variable region (VL) comprising an amino acid sequence that is at least 90% identical to a selected VL sequence, wherein the selected VH sequence and the selected VL sequence are one of the following:

(1) the selected VH sequence is SEQ ID NO: 53, 54, 55, or 79, and the selected VL sequence is SEQ ID NO: 56, 57, 58, or 80;

(2) the selected VH sequence is SEQ ID NO: 59, 60, 61, or 81, and the selected VL sequence is SEQ ID NO: 62, 63, 64, 65, or 82;

(3) the selected VH sequence is SEQ ID NO: 66, 67, 68, or 83, and the selected VL sequence is SEQ ID NO: 69, 70, 71, 72, or 84;

(4) the selected VH sequence is SEQ ID NO: 73, 74, 75, or 85, and the selected VL sequence is SEQ ID NO: 76, 77, 78, or 86.

In some embodiments, the VH comprises the sequence of SEQ ID NO: 53 and the VL comprises the sequence of SEQ ID NO: 56.

In some embodiments, the VH comprises the sequence of SEQ ID NO: 55 and the VL comprises the sequence of SEQ ID NO: 58.

In some embodiments, the VH comprises the sequence of SEQ ID NO: 55 and the VL comprises the sequence of SEQ ID NO: 56.

In some embodiments, the VH comprises the sequence of SEQ ID NO: 73 and the VL comprises the sequence of SEQ ID NO: 77.

In some embodiments, the antibody or antigen-binding fragment specifically binds to human OX40.

In some embodiments, the antibody or antigen-binding fragment is a humanized antibody or antigen-binding fragment thereof. In some embodiments, the antibody or antigen-binding fragment is a single-chain variable fragment (scFV).

In one aspect, the disclosure also provides an antibody-drug conjugate comprising the antibody or antigen-binding fragment thereof covalently or non-covalently bound to a therapeutic agent. In some embodiments, the therapeutic agent is a cytotoxic or cytostatic agent (e.g., cytochalasin B, gramicidin D, ethidium bromide, emetine, mitomycin, etoposide, tenoposide, vincristine, vinblastine, colchicin, doxorubicin, daunorubicin, dihydroxy anthracin, maytansinoids such as DM-1 and DM-4, dione, mitoxantrone, mithramycin, actinomycin D, 1-dehydrotestosterone, glucocorticoids, procaine, tetracaine, lidocaine, propranolol, puromycin, epirubicin, and cyclophosphamide and analogs).

In one aspect, the disclosure also provides method of treating a subject having cancer. The methods involve administering a therapeutically effective amount of a composition comprising the antibody or antigen-binding fragment thereof or the antibody-drug conjugates as described herein to the subject.

In some embodiments, the subject has a solid tumor. In some embodiments, the cancer is unresectable melanoma or metastatic melanoma.

In some embodiments, the cancer is non-small cell lung cancer (NSCLC), squamous cell carcinoma of the head and neck (SCCHN), renal cell carcinoma (RCC), melanoma, bladder, triple-negative breast cancer (TNBC), or colorectal carcinoma.

In one aspect, the disclosure relates to methods of decreasing the rate of tumor growth. The methods involve contacting a tumor cell with an effective amount of a composition comprising an antibody or antigen-binding fragment thereof or the antibody-drug conjugates as described herein.

In another aspect, the disclosure relates to methods of killing a tumor cell. The methods involve contacting a tumor cell with an effective amount of a composition comprising the antibody or antigen-binding fragment thereof or the antibody-drug conjugates as described herein.

In one aspect, the disclosure relates to pharmaceutical compositions comprising the antibody or antigen-binding fragment thereof as described herein, and a pharmaceutically acceptable carrier.

In another aspect, the disclosure relates to pharmaceutical compositions comprising antibody drug conjugates as described herein, and a pharmaceutically acceptable carrier.

As used herein, the term "cancer" refers to cells having the capacity for autonomous growth. Examples of such cells include cells having an abnormal state or condition characterized by rapidly proliferating cell growth. The term is meant to include cancerous growths, e.g., tumors; oncogenic processes, metastatic tissues, and malignantly transformed cells, tissues, or organs, irrespective of histopathologic type or stage of invasiveness. Also included are malignancies of the various organ systems, such as respiratory, cardiovascular, renal, reproductive, hematological, neurological, hepatic, gastrointestinal, and endocrine systems; as well as adenocarcinomas which include malignancies such as most colon cancers, renal-cell carcinoma, prostate cancer and/or testicular tumors, non-small cell carcinoma of the lung, and cancer of the small intestine. Cancer that is "naturally arising" includes any cancer that is not experimentally induced by implantation of cancer cells into a subject, and includes, for example, spontaneously arising cancer, cancer caused by exposure of a patient to a carcinogen(s), cancer resulting from insertion of a transgenic oncogene or knockout of a tumor suppressor gene, and cancer caused by infections, e.g., viral infections. The term "carcinoma" is art recognized and refers to malignancies of epithelial or endocrine tissues. The term also includes carcinosarcomas, which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation. The term "hematopoietic neoplastic disorders" includes diseases involving hyperplastic/neoplastic cells of hematopoietic origin. A hematopoietic neoplastic disorder can arise from myeloid, lymphoid or erythroid lineages, or precursor cells thereof.

As used herein, the term "antibody" refers to any antigen-binding molecule that contains at least one (e.g., one, two, three, four, five, or six) complementary determining region (CDR) (e.g., any of the three CDRs from an immunoglobulin light chain or any of the three CDRs from an immunoglobulin heavy chain) and is capable of specifically binding to an epitope. Non-limiting examples of antibodies include: monoclonal antibodies, polyclonal antibodies, multi-specific antibodies (e.g., bi-specific antibodies), single-chain antibodies, chimeric antibodies, human antibodies, and humanized antibodies. In some embodiments, an antibody can contain an Fc region of a human antibody. The term antibody also includes derivatives, e.g., bi-specific antibodies, single-chain antibodies, diabodies, linear antibodies, and multi-specific antibodies formed from antibody fragments.

As used herein, the term "antigen-binding fragment" refers to a portion of a full-length antibody, wherein the portion of the antibody is capable of specifically binding to an antigen. In some embodiments, the antigen-binding fragment contains at least one variable domain (e.g., a variable domain of a heavy chain or a variable domain of light chain). Non-limiting examples of antibody fragments include, e.g., Fab, Fab', F(ab')$_2$, and Fv fragments.

As used herein, the term "human antibody" refers to an antibody that is encoded by an endogenous nucleic acid (e.g., rearranged human immunoglobulin heavy or light chain locus) present in a human. In some embodiments, a human antibody is collected from a human or produced in a human cell culture (e.g., human hybridoma cells). In some embodiments, a human antibody is produced in a non-human cell (e.g., a mouse or hamster cell line). In some embodiments, a human antibody is produced in a bacterial or yeast cell. In some embodiments, a human antibody is produced in a transgenic non-human animal (e.g., a bovine) containing an unrearranged or rearranged human immunoglobulin locus (e.g., heavy or light chain human immunoglobulin locus).

As used herein, the term "chimeric antibody" refers to an antibody that contains a sequence present in at least two different antibodies (e.g., antibodies from two different mammalian species such as a human and a mouse antibody). A non-limiting example of a chimeric antibody is an antibody containing the variable domain sequences (e.g., all or part of a light chain and/or heavy chain variable domain sequence) of a non-human (e.g., mouse) antibody and the constant domains of a human antibody. Additional examples of chimeric antibodies are described herein and are known in the art.

As used herein, the term "humanized antibody" refers to a non-human antibody which contains minimal sequence derived from a non-human (e.g., mouse) immunoglobulin and contains sequences derived from a human immunoglobulin. In non-limiting examples, humanized antibodies are human antibodies (recipient antibody) in which hypervariable (e.g., CDR) region residues of the recipient antibody are replaced by hypervariable (e.g., CDR) region residues from a non-human antibody (e.g., a donor antibody), e.g., a mouse, rat, or rabbit antibody, having the desired specificity, affinity, and capacity. In some embodiments, the Fv framework residues of the human immunoglobulin are replaced by corresponding non-human (e.g., mouse) immunoglobulin residues. In some embodiments, humanized antibodies may contain residues which are not found in the recipient antibody or in the donor antibody. These modifications can be made to further refine antibody performance. In some embodiments, the humanized antibody contains substantially all of at least one, and typically two, variable domains, in which all or substantially all of the hypervariable loops (CDRs) correspond to those of a non-human (e.g., mouse) immunoglobulin and all or substantially all of the framework regions are those of a human immunoglobulin. The humanized antibody can also contain at least a portion of an immunoglobulin constant region (Fc), typically, that of a human immunoglobulin. Humanized antibodies can be produced using molecular biology methods known in the art. Non-limiting examples of methods for generating humanized antibodies are described herein.

As used herein, the term "single-chain antibody" refers to a single polypeptide that contains at least two immunoglobulin variable domains (e.g., a variable domain of a mammalian immunoglobulin heavy chain or light chain) that is capable of specifically binding to an antigen. Non-limiting examples of single-chain antibodies are described herein.

As used herein, the term "multimeric antibody" refers to an antibody that contains four or more (e.g., six, eight, or ten) immunoglobulin variable domains. In some embodiments, the multimeric antibody is able to crosslink one target molecule (e.g., OX40) to at least one second target molecule (e.g., PD1) on the surface of a mammalian cell (e.g., a human T-cell).

As used herein, the terms "subject" and "patient" are used interchangeably throughout the specification and describe an animal, human or non-human, to whom treatment according to the methods of the present invention is provided. Veterinary and non-veterinary applications are contemplated by the present invention. Human patients can be adult humans or juvenile humans (e.g., humans below the age of 18 years old). In addition to humans, patients include but are not limited to mice, rats, hamsters, guinea-pigs, rabbits, ferrets, cats, dogs, and primates. Included are, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

As used herein, when referring to an antibody, the phrases "specifically binding" and "specifically binds" mean that the antibody interacts with its target molecule (e.g., OX40) preferably to other molecules, because the interaction is dependent upon the presence of a particular structure (i.e., the antigenic determinant or epitope) on the target molecule; in other words, the reagent is recognizing and binding to molecules that include a specific structure rather than to all molecules in general. An antibody that specifically binds to the target molecule may be referred to as a target-specific antibody. For example, an antibody that specifically binds to a OX40 molecule may be referred to as a OX40-specific antibody or an anti-OX40 antibody.

As used herein, the terms "polypeptide," "peptide," and "protein" are used interchangeably to refer to polymers of amino acids of any length of at least two amino acids.

As used herein, the terms "polynucleotide," "nucleic acid molecule," and "nucleic acid sequence" are used interchangeably herein to refer to polymers of nucleotides of any length of at least two nucleotides, and include, without limitation, DNA, RNA, DNA/RNA hybrids, and modifications thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 31 lists CDR sequences of anti-OX40 antibodies 9H3, 9A4, 5C1, 5D10 and humanized antibodies thereof as defined by Kabat numbering.

FIG. 32 lists CDR sequences of anti-OX40 antibodies 9H3, 9A4, 5C1, 5D10 and humanized antibodies thereof as defined by Chothia numbering.

FIG. 33 lists amino acid sequences of human OX40, mouse OX40, monkey OX40, and chimeric OX40.

FIG. 34 lists amino acid sequences of heavy chain variable regions and light chain variable regions of humanized anti-OX40 antibodies.

FIG. 35 lists the amino acid sequence of the heavy chain and light chain variable regions of mouse anti-hOX40 antibodies 9H3, 9A4, 5C1, and 5D10.

STATEMENT REGARDING SEQUENCE LISTING

Figure 1:
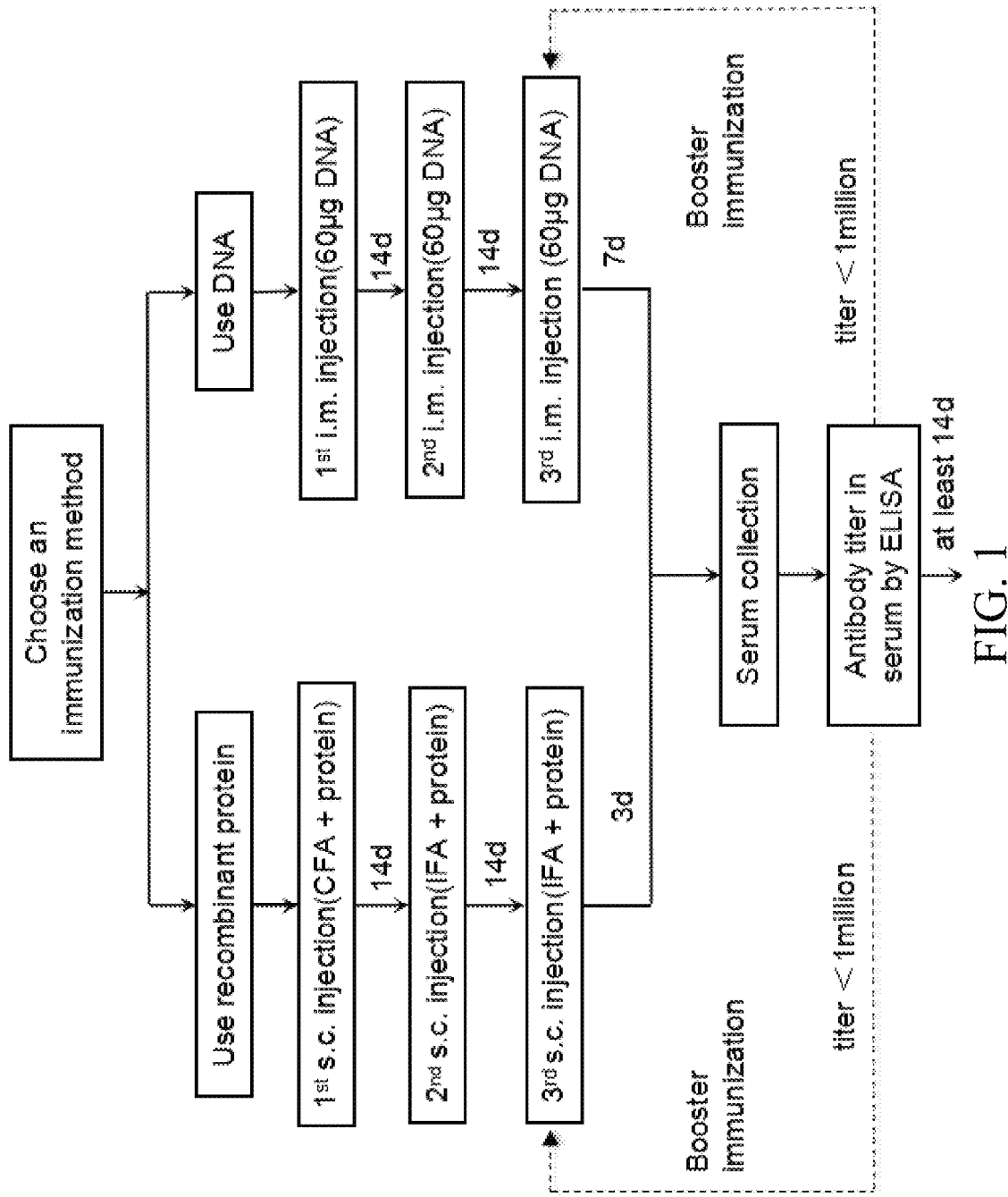
FIG. 1 is a flow chart showing the first part of an exemplary protocol of making anti-OX40 antibodies.

The Sequence Listing associated with this application is provided in text form in lieu of a paper copy, and is hereby incorporated by reference into the specification. The name of the text file containing the Sequence Listing is 45124-0012002 SL.txt. The text file is 53.3 KB, and was created and submitted electronically via EFS-Web on Jan. 5, 2021.

DETAILED DESCRIPTION

The present disclosure provides examples of antibodies, antigen-binding fragment thereof, that bind to OX40 (TNF Receptor Superfamily Member 4, or TNFRSF4; also known as CD134).

The T cell activation process requires TCR to recognize the WIC-peptide complex as the first signal. It also further requires co-stimulatory signals. OX40 is a class of co-stimulatory factors for T cells, which is a member of the tumor necrosis factor receptor (TNFR) superfamily, and a type I transmembrane protein. OX40 can activate the intracellular PI3K-AKT signal as well as the NFAT signal. These signals have a positive effect on the proliferation and survival of T cells. In addition, OX40 can also regulate the function and differentiation direction of T cells.

OX40 is by far the only co-stimulatory molecule that is able to establish peripheral tolerance. It can break the immune tolerance of a tumor and restore immune surveillance. The employment of OX40 as a new target for tumor immunotherapy has already shown certain positive effects. However, since the activation antibody needs to have its epitope for binding and its status to be exactly aligned with the corresponding ligand in order to activate the downstream signaling pathway, which is similar to a key that specifically matches a lock, the development of this type of antibody is challenging. This disclosure provides several anti-OX40 antibodies and humanized anti-OX40 antibodies anti-OX40 antibodies that can effectively inhibit tumor growth and can be used for treating cancers.

OX40 and Cancer

The immune system can differentiate between normal cells in the body and those it sees as "foreign," which allows the immune system to attack the foreign cells while leaving the normal cells alone. This mechanism sometimes involves proteins called immune checkpoints. Immune checkpoints are molecules in the immune system that either turn up a signal (co-stimulatory molecules) or turn down a signal.

Checkpoint inhibitors can prevent the immune system from attacking normal tissue and thereby preventing autoimmune diseases. Many tumor cells also express checkpoint inhibitors. These tumor cells escape immune surveillance by co-opting certain immune-checkpoint pathways, particularly in T cells that are specific for tumor antigens (Creelan, Benjamin C. "Update on immune checkpoint inhibitors in lung cancer." Cancer Control 21.1 (2014): 80-89). Because many immune checkpoints are initiated by ligand-receptor interactions, they can be readily blocked by antibodies against the ligands and/or their receptors.

Tumor necrosis factor receptor superfamily, member 4 (TNFRSF4), also known as CD134 and OX40, is a member of the TNFR-superfamily of receptors which is not constitutively expressed on resting naïve T cells. OX40 is a secondary co-stimulatory immune checkpoint molecule, expressed after 24 to 72 hours following activation; its ligand, OX40L, is also not expressed on resting antigen presenting cells, but is following their activation.

The expression of OX40 on the surface of mouse T-cells typically occurs between 24 h and 96 h after cognate antigen recognition. Engagement of the OX40 receptor on T-cells (in vitro), using anti-OX40 agonistic antibodies, directly promotes an increase in survival of different effector T-cell subsets. Moreover, the immunosuppressive subset of CD4+ T-cells called regulatory T-cells (Tregs) also express high levels of OX40. Of note, murine Tregs seem to constitutively express OX40 whereas human Tregs would upregulate OX40 upon activation. Tregs can inhibit effector T-cells through the secretion of immunosuppressive cytokines such as transforming growth factor-beta (TGFb) and interleukin-10 (IL-10). These negative regulators can be counter balanced by the stimulation of OX40 on effector T-cells and other TNFRSF co-stimulatory receptors such as 41BB (CD137) and glucocorticoid-induced tumor necrosis factor receptor (GITR) (CD357).

OX40 signaling influences Tregs function and impairs their suppressing ability, presumably through direct inhibition of FoxP3 expression. OX40 signaling also acts on the generation of Tregs: it strongly antagonizes TGFb and the antigen mediated-conversion of naive T-cells into FoxP3 þ Tregs.

As OX40 signaling strongly promotes the bioactivity of CD4+ and CD8+ T-cells and counteract Tregs functions, OX40 is as an immunomodulatory target for cancer immunotherapy, for example, OX40 signaling can be induced by OX40 specific agonistic antibodies. A detailed description regarding OX40 and its role as an immunomodulatory target for cancer immunotherapy can be found, e.g., in Aspeslagh, et al. "Rationale for anti-OX40 cancer immunotherapy." European Journal of Cancer 52 (2016): 50-66; Curti, et al. "OX40 is a potent immune-stimulating target in late-stage cancer patients." Cancer research 73.24 (2013): 7189-7198, which are incorporated herein by reference in the entirety.

The present disclosure provides several anti-OX40 antibodies, antigen-binding fragments thereof, and methods of using these anti-OX40 antibodies and antigen-binding fragments to inhibit tumor growth and to treat cancers.

Antibodies and Antigen Binding Fragments

The present disclosure provides anti-OX40 antibodies and antigen-binding fragments thereof. In general, antibodies (also called immunoglobulins) are made up of two classes of polypeptide chains, light chains and heavy chains. A non-limiting antibody of the present disclosure can be an intact, four immunoglobulin chain antibody comprising two heavy chains and two light chains. The heavy chain of the antibody can be of any isotype including IgM, IgG, IgE, IgA, or IgD or sub-isotype including IgG1, IgG2, IgG2a, IgG2b, IgG3, IgG4, IgE1, IgE2, etc. The light chain can be a kappa light chain or a lambda light chain. An antibody can comprise two identical copies of a light chain and two identical copies of a heavy chain. The heavy chains, which each contain one variable domain (or variable region, VH) and multiple constant domains (or constant regions), bind to one another via disulfide bonding within their constant domains to form the "stem" of the antibody. The light chains, which each contain one variable domain (or variable region, VL) and one constant domain (or constant region), each bind to one heavy chain via disulfide binding. The variable region of each light chain is aligned with the variable region of the heavy chain to which it is bound. The variable regions of both the light chains and heavy chains contain three hypervariable regions sandwiched between more conserved framework regions (FR).

These hypervariable regions, known as the complementary determining regions (CDRs), form loops that comprise the principle antigen binding surface of the antibody. The four framework regions largely adopt a beta-sheet conformation and the CDRs form loops connecting, and in some cases forming part of, the beta-sheet structure. The CDRs in each chain are held in close proximity by the framework regions and, with the CDRs from the other chain, contribute to the formation of the antigen-binding region.

Methods for identifying the CDR regions of an antibody by analyzing the amino acid sequence of the antibody are well known, and a number of definitions of the CDRs are commonly used. The Kabat definition is based on sequence variability, and the Chothia definition is based on the location of the structural loop regions. These methods and definitions are described in, e.g., Martin, "Protein sequence and structure analysis of antibody variable domains," Antibody engineering, Springer Berlin Heidelberg, 2001. 422-439; Abhinandan, et al. "Analysis and improvements to Kabat and structurally correct numbering of antibody variable domains," Molecular immunology 45.14 (2008): 3832-3839; Wu, T. T. and Kabat, E. A. (1970) J. Exp. Med. 132: 211-250; Martin et al., Methods Enzymol. 203:121-53 (1991); Morea et al., Biophys Chem. 68(1-3):9-16 (October 1997); Morea et al., J Mol Biol. 275(2):269-94 (January 1998); Chothia et al., Nature 342(6252):877-83 (December 1989); Ponomarenko and Bourne, BMC Structural Biology 7:64 (2007); each of which is incorporated herein by reference in its entirety. Unless specifically indicated in the present disclosure, Kabat numbering is used in the present disclosure as a default.

The CDRs are important for recognizing an epitope of an antigen. As used herein, an "epitope" is the smallest portion of a target molecule capable of being specifically bound by the antigen binding domain of an antibody. The minimal size of an epitope may be about three, four, five, six, or seven amino acids, but these amino acids need not be in a consecutive linear sequence of the antigen's primary structure, as the epitope may depend on an antigen's three-dimensional configuration based on the antigen's secondary and tertiary structure.

In some embodiments, the antibody is an intact immunoglobulin molecule (e.g., IgG1, IgG2a, IgG2b, IgG3, IgM, IgD, IgE, IgA). The IgG subclasses (IgG1, IgG2, IgG3, and IgG4) are highly conserved, differ in their constant region, particularly in their hinges and upper CH2 domains. The sequences and differences of the IgG subclasses are known in the art, and are described, e.g., in Vidarsson, et al, "IgG subclasses and allotypes: from structure to effector functions." Frontiers in immunology 5 (2014); Irani, et al. "Molecular properties of human IgG subclasses and their implications for designing therapeutic monoclonal antibodies against infectious diseases." Molecular immunology 67.2 (2015): 171-182; Shakib, Farouk, ed. The human IgG subclasses: molecular analysis of structure, function and regulation. Elsevier, 2016; each of which is incorporated herein by reference in its entirety.

The antibody can also be an immunoglobulin molecule that is derived from any species (e.g., human, rodent, mouse, camelid). Antibodies disclosed herein also include, but are not limited to, polyclonal, monoclonal, monospecific, polyspecific antibodies, and chimeric antibodies that include an immunoglobulin binding domain fused to another polypeptide. The term "antigen binding domain" or "antigen binding fragment" is a portion of an antibody that retains specific binding activity of the intact antibody, i.e., any portion of an antibody that is capable of specific binding to an epitope on the intact antibody's target molecule. It includes, e.g., Fab, Fab', F(ab')$_2$, and variants of these fragments. Thus, in some embodiments, an antibody or an antigen binding fragment thereof can be, e.g., a scFv, a Fv, a Fd, a dAb, a bispecific antibody, a bispecific scFv, a diabody, a linear antibody, a single-chain antibody molecule, a multi-specific antibody formed from antibody fragments, and any polypeptide that includes a binding domain which is, or is homologous to, an antibody binding domain. Non-limiting examples of antigen binding domains include, e.g., the heavy chain and/or light chain CDRs of an intact antibody, the heavy and/or light chain variable regions of an intact antibody, full length heavy or light chains of an intact antibody, or an individual CDR from either the heavy chain or the light chain of an intact antibody.

In some embodiments, the antigen binding fragment can form a part of a chimeric antigen receptor (CAR). In some embodiments, the chimeric antigen receptor are fusions of single-chain variable fragments (scFv) as described herein, fused to CD3-zeta transmembrane- and endodomain. In some embodiments, the chimeric antigen receptor also comprises intracellular signaling domains from various costimulatory protein receptors (e.g., CD28, 41BB, ICOS). In some embodiments, the chimeric antigen receptor comprises multiple signaling domains, e.g., CD3z-CD28-41BB or CD3z-CD28-OX40, to increase potency. Thus, in one aspect, the disclosure further provides cells (e.g., T cells) that express the chimeric antigen receptors as described herein.

In some embodiments, the scFV has one heavy chain variable domain, and one light chain variable domain.

Anti-OX40 Antibodies and Antigen-Binding Fragments

The disclosure provides antibodies and antigen-binding fragments thereof that specifically bind to OX40. The antibodies and antigen-binding fragments described herein are capable of binding to OX40 and can promote OX40 signaling pathway thus increase immune response. The disclosure provides e.g., mouse anti-OX40 antibodies 07-9H3 ("9H3"), 07-9A4 ("9A4"), 11-5C1 ("5C1"), and 17-5D10 ("5D10"), and chimeric antibodies, the humanized antibodies thereof (e.g., antibodies as shown in Table 3).

The CDR sequences for 9H3, and 9H3 derived antibodies (e.g., humanized antibodies) include CDRs of the heavy chain variable domain, SEQ ID NOs: 1-3, and CDRs of the light chain variable domain, SEQ ID NOs: 4-6 as defined by Kabat numbering. The CDRs can also be defined by Chothia system. Under the Chothia numbering, the CDR sequences of the heavy chain variable domain are set forth in SEQ ID NOs: 25-27, and CDR sequences of the light chain variable domain are set forth in SEQ ID NOs: 28-30.

Similarly, the CDR sequences for 9A4, and 9A4 derived antibodies include CDRs of the heavy chain variable domain, SEQ ID NOs: 7-9, and CDRs of the light chain variable domain, SEQ ID NOs: 10-12, as defined by Kabat numbering. Under Chothia numbering, the CDR sequences of the heavy chain variable domain are set forth in SEQ ID NOs: 31-33, and CDRs of the light chain variable domain are set forth in SEQ ID NOs: 34-36.

The CDR sequences for 5C1, and 5C1 derived antibodies include CDRs of the heavy chain variable domain, SEQ ID NOs: 13-15, and CDRs of the light chain variable domain, SEQ ID NOs: 16-18, as defined by Kabat numbering. Under Chothia numbering, the CDR sequences of the heavy chain variable domain are set forth in SEQ ID NOs: 37-39, and CDRs of the light chain variable domain are set forth in SEQ ID NOs: 40-42.

The CDR sequences for 5D10, and 5D10 derived antibodies include CDRs of the heavy chain variable domain, SEQ ID NOs: 19-21, and CDRs of the light chain variable domain, SEQ ID NOs: 22-24, as defined by Kabat numbering. Under Chothia numbering, the CDR sequences of the heavy chain variable domain are set forth in SEQ ID NOs: 43-45, and CDRs of the light chain variable domain are set forth in SEQ ID NOs: 46-48.

The amino acid sequence for heavy chain variable region and light variable region of humanized antibodies are also provided. As there are different ways to humanize the mouse antibody (e.g., sequence can be substituted by different amino acids), the heavy chain and the light chain of an antibody can have more than one versions of humanized sequences. The amino acid sequences for the heavy chain variable region of humanized 9H3 antibody are set forth in SEQ ID NOs: 53-55. The amino acid sequences for the light chain variable region of humanized 9H3 antibody are set forth in SEQ ID NOs: 56-58. Any of these heavy chain variable region sequences (SEQ ID NO: 53-55) can be paired with any of these light chain variable region sequences (SEQ ID NO: 56-58).

Similarly, the amino acid sequences for the heavy chain variable region of humanized 9A4 antibody are set forth in SEQ ID NOs: 59-61. The amino acid sequences for the light chain variable region of humanized 9A4 antibody are set forth in SEQ ID NOs: 62-65. Any of these heavy chain variable region sequences (SEQ ID NO: 59-61) can be paired with any of these light chain variable region sequences (SEQ ID NO: 62-65).

The amino acid sequences for the heavy chain variable region of humanized 5C1 antibody are set forth in SEQ ID NOs: 66-68. The amino acid sequences for the light chain variable region of humanized 5C1 antibody are set forth in SEQ ID NOs: 69-72. Any of these heavy chain variable region sequences (SEQ ID NOs: 66-68) can be paired with any of these light chain variable region sequences (SEQ ID NOs: 69-72).

The amino acid sequences for the heavy chain variable region of humanized 5D10 antibody are set forth in SEQ ID NOs: 73-75. The amino acid sequences for the light chain variable region of humanized 5D10 antibody are set forth in SEQ ID NOs: 76-78. Any of these heavy chain variable region sequences (SEQ ID NOs: 73-75) can be paired with any of these light chain variable region sequences (SEQ ID NOs: 76-78).

As shown in FIG. 34, humanization percentage means the percentage identity of the heavy chain or light chain variable region sequence as compared to human antibody sequences in International Immunogenetics Information System (IMGT) database. The top hit means that the heavy chain or light chain variable region sequence is closer to a particular species than to other species. For example, top hit to human means that the sequence is closer to human than to other species. Top hit to human and *Macaca fascicularis* means that the sequence has the same percentage identity to the human sequence and the *Macaca fascicularis* sequence, and these percentages identities are highest as compared to the sequences of other species. In some embodiments, humanization percentage is greater than 80%, 81%, 82%, 83%, 84%, 85%, 86%, 87%, 88%, 89%, 90%, 91%, 92%, 93%, 94%, or 95%. A detailed description regarding how to determine humanization percentage and how to determine top hits is known in the art, and is described, e.g., in Jones, Tim D., et al. "The INNs and outs of antibody nonproprietary names." MAbs. Vol. 8. No. 1. Taylor & Francis, 2016, which is incorporated herein by reference in its entirety. A high humanization percentage often has various advantages, e.g., more safe and more effective in humans, more likely to be tolerated by a human subject, and/or less likely to have side effects.

Furthermore, in some embodiments, the antibodies or antigen-binding fragments thereof described herein can also contain one, two, or three heavy chain variable region CDRs selected from the group of SEQ ID NOs: 1-3, SEQ ID NOs:

7-9, SEQ ID NOs: 13-15, SEQ ID NOs: 19-21, SEQ ID NOs: 25-27, SEQ ID NOs: 31-33, SEQ ID NOs: 37-39, and SEQ ID NOs: 43-45; and/or one, two, or three light chain variable region CDRs selected from the group of SEQ ID NOs: 4-6, SEQ ID NOs 10-12, SEQ ID NOs: 16-18, SEQ ID NOs 22-24, SEQ ID NOs 28-30, SEQ ID NOs 34-36, SEQ ID NOs 40-42, and SEQ ID NOs 46-48.

In some embodiments, the antibodies can have a heavy chain variable region (VH) comprising complementarity determining regions (CDRs) 1, 2, 3, wherein the CDR1 region comprises or consists of an amino acid sequence that is at least 80%, 85%, 90%, or 95% identical to a selected VH CDR1 amino acid sequence, the CDR2 region comprises or consists of an amino acid sequence that is at least 80%, 85%, 90%, or 95% identical to a selected VH CDR2 amino acid sequence, and the CDR3 region comprises or consists of an amino acid sequence that is at least 80%, 85%, 90%, or 95% identical to a selected VH CDR3 amino acid sequence, and a light chain variable region (VL) comprising CDRs 1, 2, 3, wherein the CDR1 region comprises or consists of an amino acid sequence that is at least 80%, 85%, 90%, or 95% identical to a selected VL CDR1 amino acid sequence, the CDR2 region comprises or consists of an amino acid sequence that is at least 80%, 85%, 90%, or 95% identical to a selected VL CDR2 amino acid sequence, and the CDR3 region comprises or consists of an amino acid sequence that is at least 80%, 85%, 90%, or 95% identical to a selected VL CDR3 amino acid sequence. The selected VH CDRs 1, 2, 3 amino acid sequences and the selected VL CDRs, 1, 2, 3 amino acid sequences are shown in FIG. 31 (Kabat CDR) and FIG. 32 (Chothia CDR).

In some embodiments, the antibody or an antigen-binding fragment described herein can contain a heavy chain variable domain containing one, two, or three of the CDRs of SEQ ID NO: 1 with zero, one or two amino acid insertions, deletions, or substitutions; SEQ ID NO: 2 with zero, one or two amino acid insertions, deletions, or substitutions; SEQ ID NO: 3 with zero, one or two amino acid insertions, deletions, or substitutions.

In some embodiments, the antibody or an antigen-binding fragment described herein can contain a heavy chain variable domain containing one, two, or three of the CDRs of SEQ ID NO: 7 with zero, one or two amino acid insertions, deletions, or substitutions; SEQ ID NO: 8 with zero, one or two amino acid insertions, deletions, or substitutions; SEQ ID NO: 9 with zero, one or two amino acid insertions, deletions, or substitutions.

In some embodiments, the antibody or an antigen-binding fragment described herein can contain a heavy chain variable domain containing one, two, or three of the CDRs of SEQ ID NO: 13 with zero, one or two amino acid insertions, deletions, or substitutions; SEQ ID NO: 14 with zero, one or two amino acid insertions, deletions, or substitutions; SEQ ID NO: 15 with zero, one or two amino acid insertions, deletions, or substitutions.

In some embodiments, the antibody or an antigen-binding fragment described herein can contain a heavy chain variable domain containing one, two, or three of the CDRs of SEQ ID NO: 19 with zero, one or two amino acid insertions, deletions, or substitutions; SEQ ID NO: 20 with zero, one or two amino acid insertions, deletions, or substitutions; SEQ ID NO: 21 with zero, one or two amino acid insertions, deletions, or substitutions.

In some embodiments, the antibody or an antigen-binding fragment described herein can contain a heavy chain variable domain containing one, two, or three of the CDRs of SEQ ID NO: 25 with zero, one or two amino acid insertions, deletions, or substitutions; SEQ ID NO: 26 with zero, one or two amino acid insertions, deletions, or substitutions; SEQ ID NO: 27 with zero, one or two amino acid insertions, deletions, or substitutions.

In some embodiments, the antibody or an antigen-binding fragment described herein can contain a heavy chain variable domain containing one, two, or three of the CDRs of SEQ ID NO: 31 with zero, one or two amino acid insertions, deletions, or substitutions; SEQ ID NO: 32 with zero, one or two amino acid insertions, deletions, or substitutions; SEQ ID NO: 33 with zero, one or two amino acid insertions, deletions, or substitutions.

In some embodiments, the antibody or an antigen-binding fragment described herein can contain a heavy chain variable domain containing one, two, or three of the CDRs of SEQ ID NO: 37 with zero, one or two amino acid insertions, deletions, or substitutions; SEQ ID NO: 38 with zero, one or two amino acid insertions, deletions, or substitutions; SEQ ID NO: 39 with zero, one or two amino acid insertions, deletions, or substitutions.

In some embodiments, the antibody or an antigen-binding fragment described herein can contain a heavy chain variable domain containing one, two, or three of the CDRs of SEQ ID NO: 43 with zero, one or two amino acid insertions, deletions, or substitutions; SEQ ID NO: 44 with zero, one or two amino acid insertions, deletions, or substitutions; SEQ ID NO: 45 with zero, one or two amino acid insertions, deletions, or substitutions.

In some embodiments, the antibody or an antigen-binding fragment described herein can contain a light chain variable domain containing one, two, or three of the CDRs of SEQ ID NO: 4 with zero, one or two amino acid insertions, deletions, or substitutions; SEQ ID NO: 5 with zero, one or two amino acid insertions, deletions, or substitutions; SEQ ID NO: 6 with zero, one or two amino acid insertions, deletions, or substitutions.

In some embodiments, the antibody or an antigen-binding fragment described herein can contain a light chain variable domain containing one, two, or three of the CDRs of SEQ ID NO: 10 with zero, one or two amino acid insertions, deletions, or substitutions; SEQ ID NO: 11 with zero, one or two amino acid insertions, deletions, or substitutions; SEQ ID NO: 12 with zero, one or two amino acid insertions, deletions, or substitutions.

In some embodiments, the antibody or an antigen-binding fragment described herein can contain a light chain variable domain containing one, two, or three of the CDRs of SEQ ID NO: 16 with zero, one or two amino acid insertions, deletions, or substitutions; SEQ ID NO: 17 with zero, one or two amino acid insertions, deletions, or substitutions; SEQ ID NO: 18 with zero, one or two amino acid insertions, deletions, or substitutions.

In some embodiments, the antibody or an antigen-binding fragment described herein can contain a light chain variable domain containing one, two, or three of the CDRs of SEQ ID NO: 22 with zero, one or two amino acid insertions, deletions, or substitutions; SEQ ID NO: 23 with zero, one or two amino acid insertions, deletions, or substitutions; SEQ ID NO: 24 with zero, one or two amino acid insertions, deletions, or substitutions.

In some embodiments, the antibody or an antigen-binding fragment described herein can contain a light chain variable domain containing one, two, or three of the CDRs of SEQ ID NO: 28 with zero, one or two amino acid insertions, deletions, or substitutions; SEQ ID NO: 29 with zero, one or two amino acid insertions, deletions, or substitutions; SEQ ID NO: 30 with zero, one or two amino acid insertions, deletions, or substitutions.

In some embodiments, the antibody or an antigen-binding fragment described herein can contain a light chain variable domain containing one, two, or three of the CDRs of SEQ ID NO: 34 with zero, one or two amino acid insertions, deletions, or substitutions; SEQ ID NO: 35 with zero, one or two amino acid insertions, deletions, or substitutions; SEQ ID NO: 36 with zero, one or two amino acid insertions, deletions, or substitutions.

In some embodiments, the antibody or an antigen-binding fragment described herein can contain a light chain variable domain containing one, two, or three of the CDRs of SEQ ID NO: 40 with zero, one or two amino acid insertions, deletions, or substitutions; SEQ ID NO: 41 with zero, one or two amino acid insertions, deletions, or substitutions; SEQ ID NO: 42 with zero, one or two amino acid insertions, deletions, or substitutions.

In some embodiments, the antibody or an antigen-binding fragment described herein can contain a light chain variable domain containing one, two, or three of the CDRs of SEQ ID NO: 46 with zero, one or two amino acid insertions, deletions, or substitutions; SEQ ID NO: 47 with zero, one or two amino acid insertions, deletions, or substitutions; SEQ ID NO: 48 with zero, one or two amino acid insertions, deletions, or substitutions.

The insertions, deletions, and substitutions can be within the CDR sequence, or at one or both terminal ends of the CDR sequence.

The disclosure also provides antibodies or antigen-binding fragments thereof that bind to OX40. The antibodies or antigen-binding fragments thereof contain a heavy chain variable region (VH) comprising or consisting of an amino acid sequence that is at least 80%, 85%, 90%, or 95% identical to a selected VH sequence, and a light chain variable region (VL) comprising or consisting of an amino acid sequence that is at least 80%, 85%, 90%, or 95% identical to a selected VL sequence. In some embodiments, the selected VH sequence is SEQ ID NOs: 53, 54, 55, or 79, and the selected VL sequence is SEQ ID NOs: 56, 57, 58, or 80. In some embodiments, the selected VH sequence is SEQ ID NOs: 59, 60, 61, or 81, and the selected VL sequence is SEQ ID NOs: 62, 63, 64, 65, or 82. In some embodiments, the selected VH sequence is SEQ ID NOs: 66, 67, 68, or 83, and the selected VL sequence is SEQ ID NOs: 69, 70, 71, 72, or 84. In some embodiments, the selected VH sequence is SEQ ID NOs: 73, 74, 75, or 85, and the selected VL sequence is SEQ ID NOs: 76, 77, 78, or 86.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences. For purposes of the present disclosure, the comparison of sequences and determination of percent identity between two sequences can be accomplished using a Blossum 62 scoring matrix with a gap penalty of 12, a gap extend penalty of 4, and a frameshift gap penalty of 5.

The disclosure also provides nucleic acid comprising a polynucleotide encoding a polypeptide comprising an immunoglobulin heavy chain or an immunoglobulin heavy chain. The immunoglobulin heavy chain or immunoglobulin light chain comprises CDRs as shown in FIG. 31 or FIG. 32, or have sequences as shown in FIG. 34 or FIG. 35. When the polypeptides are paired with corresponding polypeptide (e.g., a corresponding heavy chain variable region or a corresponding light chain variable region), the paired polypeptides bind to OX40 (e.g., human OX40).

The anti-OX40 antibodies and antigen-binding fragments can also be antibody variants (including derivatives and conjugates) of antibodies or antibody fragments and multispecific (e.g., bi-specific) antibodies or antibody fragments. Additional antibodies provided herein are polyclonal, monoclonal, multi-specific (multimeric, e.g., bi-specific), human antibodies, chimeric antibodies (e.g., human-mouse chimera), single-chain antibodies, intracellularly-made antibodies (i.e., intrabodies), and antigen-binding fragments thereof. The antibodies or antigen-binding fragments thereof can be of any type (e.g., IgG, IgE, IgM, IgD, IgA, and IgY), class (e.g., IgG1, IgG2, IgG3, IgG4, IgA1, and IgA2), or subclass. In some embodiments, the antibody or antigen-binding fragment thereof is an IgG antibody or antigen-binding fragment thereof.

Fragments of antibodies are suitable for use in the methods provided so long as they retain the desired affinity and specificity of the full-length antibody. Thus, a fragment of an antibody that binds to OX40 will retain an ability to bind to OX40. An Fv fragment is an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the VH-VL dimer. Collectively, the six CDRs or a subset thereof confer antigen binding specificity to the antibody. However, even a single variable domain (or half of an Fv comprising only three CDRs specific for an antigen) can have the ability to recognize and bind antigen, although usually at a lower affinity than the entire binding site.

Single-chain Fv or (scFv) antibody fragments comprise the VH and VL domains (or regions) of antibody, wherein these domains are present in a single polypeptide chain. Generally, the scFv polypeptide further comprises a polypeptide linker between the VH and VL domains, which enables the scFv to form the desired structure for antigen binding.

The Fab fragment contains a variable and constant domain of the light chain and a variable domain and the first constant domain (CH1) of the heavy chain. F(ab')$_2$ antibody fragments comprise a pair of Fab fragments which are generally covalently linked near their carboxy termini by hinge cysteines between them. Other chemical couplings of antibody fragments are also known in the art.

Diabodies are small antibody fragments with two antigen-binding sites, which fragments comprise a VH connected to a VL in the same polypeptide chain (VH and VL). By using a linker that is too short to allow pairing between the two domains on the same chain, the domains are forced to pair with the complementary domains of another chain and create two antigen-binding sites.

Linear antibodies comprise a pair of tandem Fd segments (VH-CH1-VH-CH1) which, together with complementary light chain polypeptides, form a pair of antigen binding regions. Linear antibodies can be bispecific or monospecific.

Antibodies and antibody fragments of the present disclosure can be modified in the Fc region to provide desired effector functions or serum half-life.

Multimerization of antibodies may be accomplished through natural aggregation of antibodies or through chemical or recombinant linking techniques known in the art. For example, some percentage of purified antibody preparations (e.g., purified $IgG_1$ molecules) spontaneously form protein aggregates containing antibody homodimers and other higher-order antibody multimers.

Alternatively, antibody homodimers may be formed through chemical linkage techniques known in the art. For example, heterobifunctional crosslinking agents including, but not limited to SMCC (succinimidyl 4-(maleimidomethyl)cyclohexane-1-carboxylate) and SATA (N-succinimidyl S-acetylthio-acetate) can be used to form antibody multimers. An exemplary protocol for the formation of antibody homodimers is described in Ghetie et al. (*Proc. Natl. Acad. Sci. U.S.A.* 94: 7509-7514, 1997). Antibody homodimers can be converted to $Fab'_2$ homodimers through digestion with pepsin. Another way to form antibody homodimers is through the use of the autophilic T15 peptide described in Zhao et al. (*J. Immunol.* 25:396-404, 2002).

In some embodiments, the multi-specific antibody is a bi-specific antibody. Bi-specific antibodies can be made by engineering the interface between a pair of antibody molecules to maximize the percentage of heterodimers that are recovered from recombinant cell culture. For example, the interface can contain at least a part of the CH3 domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. This method is described, e.g., in WO 96/27011, which is incorporated by reference in its entirety.

Bi-specific antibodies include cross-linked or "heteroconjugate" antibodies. For example, one of the antibodies in the heteroconjugate can be coupled to avidin and the other to biotin. Heteroconjugate antibodies can also be made using any convenient cross-linking methods. Suitable cross-linking agents and cross-linking techniques are well known in the art and are disclosed in U.S. Pat. No. 4,676,980, which is incorporated herein by reference in its entirety.

Methods for generating bi-specific antibodies from antibody fragments are also known in the art. For example, bi-specific antibodies can be prepared using chemical linkage. Brennan et al. (*Science* 229:81, 1985) describes a procedure where intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab' TNB derivatives is then reconverted to the Fab' thiol by reduction with mercaptoethylamine, and is mixed with an equimolar amount of another Fab' TNB derivative to form the bi-specific antibody.

Any of the antibodies or antigen-binding fragments described herein may be conjugated to a stabilizing molecule (e.g., a molecule that increases the half-life of the antibody or antigen-binding fragment thereof in a subject or in solution). Non-limiting examples of stabilizing molecules include: a polymer (e.g., a polyethylene glycol) or a protein (e.g., serum albumin, such as human serum albumin). The conjugation of a stabilizing molecule can increase the half-life or extend the biological activity of an antibody or an antigen-binding fragment in vitro (e.g., in tissue culture or when stored as a pharmaceutical composition) or in vivo (e.g., in a human).

In some embodiments, the antibodies or antigen-binding fragments described herein can be conjugated to a therapeutic agent. The antibody-drug conjugate comprising the antibody or antigen-binding fragment thereof can covalently or non-covalently bind to a therapeutic agent. In some embodiments, the therapeutic agent is a cytotoxic or cytostatic agent (e.g., cytochalasin B, gramicidin D, ethidium bromide, emetine, mitomycin, etoposide, tenoposide, vincristine, vinblastine, colchicin, doxorubicin, daunorubicin, dihydroxy anthracin, maytansinoids such as DM-1 and DM-4, dione, mitoxantrone, mithramycin, actinomycin D, 1-dehydrotestosterone, glucocorticoids, procaine, tetracaine, lidocaine, propranolol, puromycin, epirubicin, and cyclophosphamide and analogs).

Antibody Characteristics

The antibodies or antigen-binding fragments thereof described herein can block the binding between OX40 and OX40L.

In some embodiments, by binding to OX40, the antibody can promote OX40 signaling pathway and upregulates the immune response. Thus, in some embodiments, the antibodies or antigen-binding fragments thereof as described herein are OX40 agonist. In some embodiments, the antibodies or antigen-binding fragments thereof are OX40 antagonist.

In some embodiments, the antibodies or antigen-binding fragments thereof as described herein can increase immune response, activity of OX40, activity or number of T cells (e.g., CD8+ and/or CD4+ cells) by at least 10%, 20%, 30%, 40%, 50%, 60%, 70%, 80%, 90%, 100%, 2 folds, 3 folds, 5 folds, 10 folds, or 20 folds. In some embodiments, the antibodies or antigen-binding fragments thereof as described herein can decrease the activity or number of Treg by at least 10%, 20%, 30%, 40%, 50%, 60%, 70%, 80%, 90%, 100%, 2 folds, 3 folds, 5 folds, 10 folds, or 20 folds.

In some implementations, the antibody (or antigen-binding fragments thereof) specifically binds to OX40 (e.g., human OX40, monkey OX40, mouse OX40, and/or chimeric OX40) with a dissociation rate (koff) of less than 0.1 $s^{-1}$, less than 0.01 $s^{-1}$, less than 0.001 $s^{-1}$, less than 0.0001 $s^{-1}$, or less than 0.0001 $s^{-1}$. In some embodiments, the dissociation rate (koff) is greater than 0.01 $s^{-1}$, greater than 0.001 $s^{-1}$, greater than 0.0001 $s^{-1}$, greater than 0.0001 $s^{-1}$, or greater than 0.00001 $s^{-1}$.

In some embodiments, kinetic association rates (kon) is greater than $1\times10^2$/Ms, greater than $1\times10^3$/Ms, greater than $1\times10^4$/Ms, greater than $1\times10^5$/Ms, or greater than $1\times10^6$/Ms. In some embodiments, kinetic association rates (kon) is less than $1\times10^5$/Ms, less than $1\times10^6$/Ms, or less than $1\times10^7$/Ms.

Affinities can be deduced from the quotient of the kinetic rate constants (KD=koff/kon). In some embodiments, KD is less than $1\times10^{-6}$ M, less than $1\times10^{-7}$ M, less than $1\times10^{-8}$ M, less than $1\times10^{-9}$ M, or less than $1\times10^{-10}$ M. In some embodiments, the KD is less than 30 nM, 20 nM, 15 nM, 10 nM, 9 nM, 8 nM, 7 nM, 6 nM, 5 nM, 4 nM, 3 nM, 2 nM, or 1 nM. In some embodiments, KD is greater than $1 \times 10^{-7}$ M, greater than $1 \times 10^{-8}$ M, greater than $1 \times 10^{-9}$ M, greater than $1 \times 10^{-10}$ M, greater than $1 \times 10^{-11}$ M, or greater than $1 \times 10^{-12}$ M. In some embodiments, the antibody binds to human OX40 with KD less than or equal to about 1.5 nM.

General techniques for measuring the affinity of an antibody for an antigen include, e.g., ELISA, RIA, and surface plasmon resonance (SPR). In some embodiments, the antibody binds to human OX40 (SEQ ID NO: 49), monkey OX40 (e.g., rhesus macaque OX40, SEQ ID NO: 51), chimeric OX40 (SEQ ID NO: 52), and/or mouse OX40 (SEQ ID NO: 50). In some embodiments, the antibody does not bind to human OX40 (SEQ ID NO: 49), monkey OX40 (e.g., rhesus macaque OX40, SEQ ID NO: 51; cynomolgus OX40), chimeric OX40 (SEQ ID NO: 52), and/or mouse OX40 (SEQ ID NO: 50).

In some embodiments, thermal stabilities are determined. The antibodies or antigen binding fragments as described herein can have a Tm greater than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C. As IgG can be described as a multi-domain protein, the melting curve sometimes shows two transitions, with a first denaturation temperature, Tm D1, and a second denaturation temperature Tm D2. The presence of these two peaks often indicate the denaturation of the Fc domains (Tm D1) and Fab domains (Tm D2), respectively. When there are two peaks, Tm usually refers to Tm D2.

Thus, in some embodiments, the antibodies or antigen binding fragments as described herein has a Tm D1 greater than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C. In some embodiments, the antibodies or antigen binding fragments as described herein has a Tm D2 greater than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C.

In some embodiments, Tm, Tm D1, Tm D2 are less than 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95° C.

In some embodiments, the antibody has a tumor growth inhibition percentage (TGI %) that is greater than 10%, 20%, 30%, 40%, 50%, 60%, 70%, 80%, 90%, 100%, 110%, 120%, 130%, 140%, 150%, 160%, 170%, 180%, 190%, or 200%. In some embodiments, the antibody has a tumor growth inhibition percentage that is less than 60%, 70%, 80%, 90%, 100%, 110%, 120%, 130%, 140%, 150%, 160%, 170%, 180%, 190%, or 200%. The TGI % can be determined, e.g., at 3, 4, 5, 6, 7, 8, 9, 10, 11, 12, 13, 14, 15, 16, 17, 18, 19, 20, 21, 22, 23, 24, 25, 26, 27, 28, 29, or 30 days after the treatment starts, or 1, 2, 3, 4, 5, 6, 7, 8, 9, 10, 11, or 12 months after the treatment starts. As used herein, the tumor growth inhibition percentage (TGI %) is calculated using the following formula:

$$TGI (\%) = [1 - (Ti - T0)/(Vi - V0)] \times 100$$

Ti is the average tumor volume in the treatment group on day i. T0 is the average tumor volume in the treatment group on day zero. Vi is the average tumor volume in the control group on day i. V0 is the average tumor volume in the control group on day zero.

In some embodiments, the antibodies or antigen-binding fragments thereof as described herein are OX40 agonist. In some embodiments, the antibodies or antigen binding fragments increase OX40 signal transduction in a target cell that expresses OX40. In some embodiments, OX40 signal transduction is detected by monitoring NFkB downstream signaling.

In some embodiments, the antibodies or antigen binding fragments enhance CD4+ effector T cell function, for example, by increasing CD4+ effector T cell proliferation and/or increasing gamma interferon production by the CD4+ effector T cell (e.g., as compared to proliferation and/or cytokine production prior to treatment with the antibodies or antigen binding fragments). In some embodiments, the cytokine is gamma interferon. In some embodiments, the antibodies or antigen binding fragments increase number of intratumoral (infiltrating) CD4+ effector T cells (e.g., total number of CD4+ effector T cells, or e.g., percentage of CD4+ cells in CD45+ cells), e.g., as compared to number of intratumoral (infiltrating) CD4+ T cells prior to treatment with antibodies or antigen binding fragments. In some embodiments, the antibodies or antigen binding fragments increase number of intratumoral (infiltrating) CD4+ effector T cells that express gamma interferon (e.g., total gamma interferon expressing CD4+ cells, or e.g., percentage of gamma interferon expressing CD4+ cells in total CD4+ cells), e.g., as compared to number of intratumoral (infiltrating) CD4+ T cells that express gamma interferon prior to treatment.

In some embodiments, the antibodies or antigen binding fragments increase number of intratumoral (infiltrating) CD8+ effector T cells (e.g., total number of CD8+ effector T cells, or e.g., percentage of CD8+ in CD45+ cells), e.g., as compared to number of intratumoral (infiltrating) CD8+ T effector cells prior to treatment. In some embodiments, the antibodies or antigen binding fragments increase number of intratumoral (infiltrating) CD8+ effector T cells that express gamma interferon (e.g., percentage of CD8+ cells that express gamma interferon in total CD8+ cells), e.g., compared to number of intratumoral (infiltrating) CD8+ T cells that express gamma interferon prior to treatment with anti-human OX40 antibody.

In some embodiments, the antibodies or antigen binding fragments enhance memory T cell function, for example by increasing memory T cell proliferation and/or increasing cytokine (e.g., gamma interferon) production by the memory cell.

In some embodiments, the antibodies or antigen binding fragments inhibit Treg function, for example, by decreasing Treg suppression of effector T cell function (e.g., effector T cell proliferation and/or effector T cell cytokine secretion). In some embodiments, the effector T cell is a CD4+ effector T cell. In some embodiments, the antibodies or antigen binding fragments reduce the number of intratumoral (infiltrating) Treg (e.g., total number of Treg or e.g., percentage of Fox3p+ cells in CD4+ cells).

In some embodiments, the antibodies or antigen binding fragments are depleting anti-hOX40 antibody (e.g., depletes cells that express human OX40). In some embodiments, the antibodies or antigen binding fragments deplete cells that express human OX40 in vitro. In some embodiments, the human OX40 expressing cells are CD4+ effector T cells, or Treg cells. In some embodiments, depleting is by ADCC and/or phagocytosis.

In some embodiments, the antibodies or antigen binding fragments have a functional Fc region. In some embodiments, effector function of a functional Fc region is antibody-dependent cell-mediated cytotoxicity (ADCC). In some embodiments, effector function of a functional Fc region is phagocytosis. In some embodiments, effector function of a functional Fc region is ADCC and phagocytosis. In some embodiments, the Fc region is human IgG1, human IgG2, human IgG3, or human IgG4.

In some embodiments, the antibodies or antigen binding fragments do not induce apoptosis in OX40-expressing cells (e.g., Treg).

In some embodiments, the antibodies or antigen binding fragments do not have a functional Fc region. For example, the antibodies or antigen binding fragments are Fab, Fab', F(ab')2, and FIT fragments.

Methods of Making Anti-OX40 Antibodies

An isolated fragment of human OX40 can be used as an immunogen to generate antibodies using standard techniques for polyclonal and monoclonal antibody preparation. Polyclonal antibodies can be raised in animals by multiple injections (e.g., subcutaneous or intraperitoneal injections) of an antigenic peptide or protein. In some embodiments, the antigenic peptide or protein is injected with at least one adjuvant. In some embodiments, the antigenic peptide or protein can be conjugated to an agent that is immunogenic in the species to be immunized. Animals can be injected with the antigenic peptide or protein more than one time (e.g., twice, three times, or four times).

The full-length polypeptide or protein can be used or, alternatively, antigenic peptide fragments thereof can be used as immunogens. The antigenic peptide of a protein comprises at least 8 (e.g., at least 10, 15, 20, or 30) amino acid residues of the amino acid sequence of OX40 and encompasses an epitope of the protein such that an antibody raised against the peptide forms a specific immune complex with the protein. As described above, the full length sequence of human OX40 is known in the art (SEQ ID NO: 49).

An immunogen typically is used to prepare antibodies by immunizing a suitable subject (e.g., human or transgenic animal expressing at least one human immunoglobulin locus). An appropriate immunogenic preparation can contain, for example, a recombinantly-expressed or a chemically-synthesized polypeptide (e.g., a fragment of human OX40). The preparation can further include an adjuvant, such as Freund's complete or incomplete adjuvant, or a similar immunostimulatory agent.

Polyclonal antibodies can be prepared as described above by immunizing a suitable subject with a OX40 polypeptide, or an antigenic peptide thereof (e.g., part of OX40) as an immunogen. The antibody titer in the immunized subject can be monitored over time by standard techniques, such as with an enzyme-linked immunosorbent assay (ELISA) using the immobilized OX40 polypeptide or peptide. If desired, the antibody molecules can be isolated from the mammal (e.g., from the blood) and further purified by well-known techniques, such as protein A of protein G chromatography to obtain the IgG fraction. At an appropriate time after immunization, e.g., when the specific antibody titers are highest, antibody-producing cells can be obtained from the subject and used to prepare monoclonal antibodies by standard techniques, such as the hybridoma technique originally described by Kohler et al. (*Nature* 256:495-497, 1975), the human B cell hybridoma technique (Kozbor et al., *Immunol. Today* 4:72, 1983), the EBV-hybridoma technique (Cole et al., Monoclonal Antibodies and Cancer Therapy, Alan R. Liss, Inc., pp. 77-96, 1985), or trioma techniques. The technology for producing hybridomas is well known (see, generally, Current Protocols in Immunology, 1994, Coligan et al. (Eds.), John Wiley & Sons, Inc., New York, NY). Hybridoma cells producing a monoclonal antibody are detected by screening the hybridoma culture supernatants for antibodies that bind the polypeptide or epitope of interest, e.g., using a standard ELISA assay.

Variants of the antibodies or antigen-binding fragments described herein can be prepared by introducing appropriate nucleotide changes into the DNA encoding a human, humanized, or chimeric antibody, or antigen-binding fragment thereof described herein, or by peptide synthesis. Such variants include, for example, deletions, insertions, or substitutions of residues within the amino acids sequences that make-up the antigen-binding site of the antibody or an antigen-binding domain. In a population of such variants, some antibodies or antigen-binding fragments will have increased affinity for the target protein, e.g., OX40. Any combination of deletions, insertions, and/or combinations can be made to arrive at an antibody or antigen-binding fragment thereof that has increased binding affinity for the target. The amino acid changes introduced into the antibody or antigen-binding fragment can also alter or introduce new post-translational modifications into the antibody or antigen-binding fragment, such as changing (e.g., increasing or decreasing) the number of glycosylation sites, changing the type of glycosylation site (e.g., changing the amino acid sequence such that a different sugar is attached by enzymes present in a cell), or introducing new glycosylation sites.

Antibodies disclosed herein can be derived from any species of animal, including mammals. Non-limiting examples of native antibodies include antibodies derived from humans, primates, e.g., monkeys and apes, cows, pigs, horses, sheep, camelids (e.g., camels and llamas), chicken, goats, and rodents (e.g., rats, mice, hamsters and rabbits), including transgenic rodents genetically engineered to produce human antibodies.

Human and humanized antibodies include antibodies having variable and constant regions derived from (or having the same amino acid sequence as those derived from) human germline immunoglobulin sequences. Human antibodies may include amino acid residues not encoded by human germline immunoglobulin sequences (e.g., mutations introduced by random or site-specific mutagenesis in vitro or by somatic mutation in vivo), for example in the CDRs.

A humanized antibody, typically has a human framework (FR) grafted with non-human CDRs. Thus, a humanized antibody has one or more amino acid sequence introduced into it from a source which is non-human. These non-human amino acid residues are often referred to as "import" residues, which are typically taken from an "import" variable domain. Humanization can be essentially performed by e.g., substituting rodent CDRs or CDR sequences for the corresponding sequences of a human antibody. These methods are described in e.g., Jones et al., Nature, 321:522-525 (1986); Riechmann et al., Nature, 332:323-327 (1988); Verhoeyen et al., Science, 239:1534-1536 (1988); each of which is incorporated by reference herein in its entirety. Accordingly, "humanized" antibodies are chimeric antibodies wherein substantially less than an intact human V domain has been substituted by the corresponding sequence from a non-human species. In practice, humanized antibodies are typically mouse antibodies in which some CDR residues and some FR residues are substituted by residues from analogous sites in human antibodies.

The choice of human VH and VL domains to be used in making the humanized antibodies is very important for reducing immunogenicity. According to the so-called "best-fit" method, the sequence of the V domain of a mouse antibody is screened against the entire library of known human-domain sequences. The human sequence which is closest to that of the mouse is then accepted as the human FR for the humanized antibody (Sims et al., J. Immunol., 151:2296 (1993); Chothia et al., J. Mol. Biol., 196:901 (1987)).

It is further important that antibodies be humanized with retention of high specificity and affinity for the antigen and other favorable biological properties. To achieve this goal, humanized antibodies can be prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved.

Ordinarily, amino acid sequence variants of the human, humanized, or chimeric anti-OX40 antibody will contain an amino acid sequence having at least 75%, 80%, 85%, 90%, 95%, 96%, 97%, 98%, or 99% percent identity with a sequence present in the light or heavy chain of the original antibody.

Identity or homology with respect to an original sequence is usually the percentage of amino acid residues present within the candidate sequence that are identical with a sequence present within the human, humanized, or chimeric anti-OX40 antibody or fragment, after aligning the sequences and introducing gaps, if necessary, to achieve the maximum percent sequence identity, and not considering any conservative substitutions as part of the sequence identity.

Additional modifications to the anti-OX40 antibodies or antigen-binding fragments can be made. For example, a cysteine residue(s) can be introduced into the Fc region, thereby allowing interchain disulfide bond formation in this region. The homodimeric antibody thus generated may have any increased half-life in vitro and/or in vivo. Homodimeric antibodies with increased half-life in vitro and/or in vivo can also be prepared using heterobifunctional cross-linkers as described, for example, in Wolff et al. (*Cancer Res.* 53:2560-2565, 1993). Alternatively, an antibody can be engineered which has dual Fc regions (see, for example, Stevenson et al., *Anti-Cancer Drug Design* 3:219-230, 1989).

In some embodiments, a covalent modification can be made to the anti-OX40 antibody or antigen-binding fragment thereof. These covalent modifications can be made by chemical or enzymatic synthesis, or by enzymatic or chemical cleavage. Other types of covalent modifications of the antibody or antibody fragment are introduced into the molecule by reacting targeted amino acid residues of the antibody or fragment with an organic derivatization agent that is capable of reacting with selected side chains or the N- or C-terminal residues.

In some embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues; or position 314 in Kabat numbering); however, Asn297 may also be located about ±3 amino acids upstream or downstream of position 297, i.e., between positions 294 and 300, due to minor sequence variations in antibodies. Such fucosylation variants may have improved ADCC function. In some embodiments, to reduce glycan heterogeneity, the Fc region of the antibody can be further engineered to replace the Asparagine at position 297 with Alanine (N297A).

Recombinant Vectors

The present disclosure also provides recombinant vectors (e.g., an expression vectors) that include an isolated polynucleotide disclosed herein (e.g., a polynucleotide that encodes a polypeptide disclosed herein), host cells into which are introduced the recombinant vectors (i.e., such that the host cells contain the polynucleotide and/or a vector comprising the polynucleotide), and the production of recombinant antibody polypeptides or fragments thereof by recombinant techniques.

As used herein, a "vector" is any construct capable of delivering one or more polynucleotide(s) of interest to a host cell when the vector is introduced to the host cell. An "expression vector" is capable of delivering and expressing the one or more polynucleotide(s) of interest as an encoded polypeptide in a host cell into which the expression vector has been introduced. Thus, in an expression vector, the polynucleotide of interest is positioned for expression in the vector by being operably linked with regulatory elements such as a promoter, enhancer, and/or a poly-A tail, either within the vector or in the genome of the host cell at or near or flanking the integration site of the polynucleotide of interest such that the polynucleotide of interest will be translated in the host cell introduced with the expression vector.

A vector can be introduced into the host cell by methods known in the art, e.g., electroporation, chemical transfection (e.g., DEAE-dextran), transformation, transfection, and infection and/or transduction (e.g., with recombinant virus). Thus, non-limiting examples of vectors include viral vectors (which can be used to generate recombinant virus), naked DNA or RNA, plasmids, cosmids, phage vectors, and DNA or RNA expression vectors associated with cationic condensing agents.

In some implementations, a polynucleotide disclosed herein (e.g., a polynucleotide that encodes a polypeptide disclosed herein) is introduced using a viral expression system (e.g., vaccinia or other pox virus, retrovirus, or adenovirus), which may involve the use of a non-pathogenic (defective), replication competent virus, or may use a replication defective virus. In the latter case, viral propagation generally will occur only in complementing virus packaging cells. Suitable systems are disclosed, for example, in Fisher-Hoch et al., 1989, Proc. Natl. Acad. Sci. USA 86:317-321; Flexner et al., 1989, Ann. N.Y. Acad Sci. 569:86-103; Flexner et al., 1990, Vaccine, 8:17-21; U.S. Pat. Nos. 4,603, 112, 4,769,330, and 5,017,487; WO 89/01973; U.S. Pat. No. 4,777,127; GB 2,200,651; EP 0,345,242; WO 91/02805; Berkner-Biotechniques, 6:616-627, 1988; Rosenfeld et al., 1991, Science, 252:431-434; Kolls et al., 1994, Proc. Natl. Acad. Sci. USA, 91:215-219; Kass-Eisler et al., 1993, Proc. Natl. Acad. Sci. USA, 90:11498-11502; Guzman et al., 1993, Circulation, 88:2838-2848; and Guzman et al., 1993, Cir. Res., 73:1202-1207. Techniques for incorporating DNA into such expression systems are well known to those of ordinary skill in the art. The DNA may also be "naked," as described, for example, in Ulmer et al., 1993, Science, 259:1745-1749, and Cohen, 1993, Science, 259:1691-1692. The uptake of naked DNA may be increased by coating the DNA onto biodegradable beads that are efficiently transported into the cells.

For expression, the DNA insert comprising an antibody-encoding or polypeptide-encoding polynucleotide disclosed herein can be operatively linked to an appropriate promoter (e.g., a heterologous promoter), such as the phage lambda PL promoter, the E. coli lac, trp and tac promoters, the SV40 early and late promoters and promoters of retroviral LTRs, to name a few. Other suitable promoters are known to the skilled artisan. The expression constructs can further contain sites for transcription initiation, termination and, in the transcribed region, a ribosome binding site for translation. The coding portion of the mature transcripts expressed by the constructs may include a translation initiating at the beginning and a termination codon (UAA, UGA, or UAG) appropriately positioned at the end of the polypeptide to be translated.

As indicated, the expression vectors can include at least one selectable marker. Such markers include dihydrofolate reductase or neomycin resistance for eukaryotic cell culture and tetracycline or ampicillin resistance genes for culturing in E. coli and other bacteria. Representative examples of appropriate hosts include, but are not limited to, bacterial cells, such as E. coli, Streptomyces, and Salmonella typhimurium cells; fungal cells, such as yeast cells; insect cells such as Drosophila S2 and Spodoptera Sf9 cells; animal cells such as CHO, COS, Bowes melanoma, and HK 293 cells; and plant cells. Appropriate culture mediums and conditions for the host cells described herein are known in the art.

Non-limiting vectors for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Non-limiting eukaryotic vectors include pWL-NEO, pSV2CAT, pOG44, pXT1 and pSG available from Stratagene; and pSVK3, pBPV, pMSG and pSVL available from Pharmacia. Other suitable vectors will be readily apparent to the skilled artisan.

Non-limiting bacterial promoters suitable for use include the E. coli lad and lacZ promoters, the T3 and T7 promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

In the yeast Saccharomyces cerevisiae, a number of vectors containing constitutive or inducible promoters such as alpha factor, alcohol oxidase, and PGH may be used. For reviews, see Ausubel et al. (1989) Current Protocols in Molecular Biology, John Wiley & Sons, New York, N.Y, and Grant et al., Methods Enzymol., 153: 516-544 (1997).

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., Basic Methods In Molecular Biology (1986).

Transcription of DNA encoding an antibody of the present disclosure by higher eukaryotes may be increased by inserting an enhancer sequence into the vector. Enhancers are cis-acting elements of DNA, usually about from 10 to 300 bp that act to increase transcriptional activity of a promoter in a given host cell-type. Examples of enhancers include the SV40 enhancer, which is located on the late side of the replication origin at base pairs 100 to 270, the cytomegalovirus early promoter enhancer, the polyoma enhancer on the late side of the replication origin, and adenovirus enhancers.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide (e.g., antibody) can be expressed in a modified form, such as a fusion protein (e.g., a GST-fusion) or with a histidine-tag, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties can be added to the polypeptide to facilitate purification. Such regions can be removed prior to final preparation of the polypeptide. The addition of peptide moieties to polypeptides to engender secretion or excretion, to improve stability and to facilitate purification, among others, are familiar and routine techniques in the art.

Methods of Treatment

The antibodies or antibody or antigen-binding fragments thereof of the present disclosure can be used for various therapeutic purposes. In one aspect, the disclosure provides methods for treating a cancer in a subject, methods of reducing the rate of the increase of volume of a tumor in a subject over time, methods of reducing the risk of developing a metastasis, or methods of reducing the risk of developing an additional metastasis in a subject. In some embodiments, the treatment can halt, slow, retard, or inhibit progression of a cancer. In some embodiments, the treatment can result in the reduction of in the number, severity, and/or duration of one or more symptoms of the cancer in a subject.

In one aspect, the disclosure features methods that include administering a therapeutically effective amount of an antibody or antigen-binding fragment thereof disclosed herein to a subject in need thereof (e.g., a subject having, or identified or diagnosed as having, a cancer), e.g., breast cancer (e.g., triple-negative breast cancer), carcinoid cancer, cervical cancer, endometrial cancer, glioma, head and neck cancer, liver cancer, lung cancer, small cell lung cancer, lymphoma, melanoma, ovarian cancer, pancreatic cancer, prostate cancer, renal cancer, colorectal cancer, gastric cancer, testicular cancer, thyroid cancer, bladder cancer, urethral cancer, or hematologic malignancy. In some embodiments, the cancer is unresectable melanoma or metastatic melanoma, non-small cell lung carcinoma (NSCLC), small cell lung cancer (SCLC), bladder cancer, or metastatic hormone-refractory prostate cancer. In some embodiments, the subject has a solid tumor. In some embodiments, the cancer is squamous cell carcinoma of the head and neck (SCCHN), renal cell carcinoma (RCC), triple-negative breast cancer (TNBC), or colorectal carcinoma.

In some embodiments, the compositions and methods disclosed herein can be used for treatment of patients at risk for a cancer. Patients with cancer can be identified with various methods known in the art.

As used herein, by an "effective amount" is meant an amount or dosage sufficient to effect beneficial or desired results including halting, slowing, retarding, or inhibiting progression of a disease, e.g., a cancer. An effective amount will vary depending upon, e.g., an age and a body weight of a subject to which the antibody, antigen binding fragment, antibody-encoding polynucleotide, vector comprising the polynucleotide, and/or compositions thereof is to be administered, a severity of symptoms and a route of administration, and thus administration can be determined on an individual basis.

An effective amount can be administered in one or more administrations. By way of example, an effective amount of an antibody or an antigen binding fragment is an amount sufficient to ameliorate, stop, stabilize, reverse, inhibit, slow and/or delay progression of a cancer in a patient or is an amount sufficient to ameliorate, stop, stabilize, reverse, slow and/or delay proliferation of a cell (e.g., a biopsied cell, any of the cancer cells described herein, or cell line (e.g., a cancer cell line)) in vitro. As is understood in the art, an effective amount of an antibody or antigen binding fragment may vary, depending on, inter alia, patient history as well as other factors such as the type (and/or dosage) of antibody used.

Effective amounts and schedules for administering the antibodies, antibody-encoding polynucleotides, and/or compositions disclosed herein may be determined empirically, and making such determinations is within the skill in the art. Those skilled in the art will understand that the dosage that must be administered will vary depending on, for example, the mammal that will receive the antibodies, antibody-encoding polynucleotides, and/or compositions disclosed herein, the route of administration, the particular type of antibodies, antibody-encoding polynucleotides, antigen binding fragments, and/or compositions disclosed herein used and other drugs being administered to the mammal. Guidance in selecting appropriate doses for antibody or antigen binding fragment can be found in the literature on therapeutic uses of antibodies and antigen binding fragments, e.g., Handbook of Monoclonal Antibodies, Ferrone et al., eds., Noges Publications, Park Ridge, N.J., 1985, ch. 22 and pp. 303-357; Smith et al., Antibodies in Human Diagnosis and Therapy, Haber et al., eds., Raven Press, New York, 1977, pp. 365-389.

A typical daily dosage of an effective amount of an antibody is 0.01 mg/kg to 100 mg/kg. In some embodiments, the dosage can be less than 100 mg/kg, 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.5 mg/kg, or 0.1 mg/kg. In some embodiments, the dosage can be greater than 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.5 mg/kg, 0.1 mg/kg, 0.05 mg/kg, or 0.01 mg/kg. In some embodiments, the dosage is about 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.9 mg/kg, 0.8 mg/kg, 0.7 mg/kg, 0.6 mg/kg, 0.5 mg/kg, 0.4 mg/kg, 0.3 mg/kg, 0.2 mg/kg, or 0.1 mg/kg.

In any of the methods described herein, the at least one antibody, antigen-binding fragment thereof, or pharmaceutical composition (e.g., any of the antibodies, antigen-binding fragments, or pharmaceutical compositions described herein) and, optionally, at least one additional therapeutic agent can be administered to the subject at least once a week (e.g., once a week, twice a week, three times a week, four times a week, once a day, twice a day, or three times a day). In some embodiments, at least two different antibodies and/or antigen-binding fragments are administered in the same composition (e.g., a liquid composition). In some embodiments, at least one antibody or antigen-binding fragment and at least one additional therapeutic agent are administered in the same composition (e.g., a liquid composition). In some embodiments, the at least one antibody or antigen-binding fragment and the at least one additional therapeutic agent are administered in two different compositions (e.g., a liquid composition containing at least one antibody or antigen-binding fragment and a solid oral composition containing at least one additional therapeutic agent). In some embodiments, the at least one additional therapeutic agent is administered as a pill, tablet, or capsule. In some embodiments, the at least one additional therapeutic agent is administered in a sustained-release oral formulation.

In some embodiments, the one or more additional therapeutic agents can be administered to the subject prior to, or after administering the at least one antibody, antigen-binding antibody fragment, or pharmaceutical composition (e.g., any of the antibodies, antigen-binding antibody fragments, or pharmaceutical compositions described herein). In some embodiments, the one or more additional therapeutic agents and the at least one antibody, antigen-binding antibody fragment, or pharmaceutical composition (e.g., any of the antibodies, antigen-binding antibody fragments, or pharmaceutical compositions described herein) are administered to the subject such that there is an overlap in the bioactive period of the one or more additional therapeutic agents and the at least one antibody or antigen-binding fragment (e.g., any of the antibodies or antigen-binding fragments described herein) in the subject.

In some embodiments, the subject can be administered the at least one antibody, antigen-binding antibody fragment, or pharmaceutical composition (e.g., any of the antibodies, antigen-binding antibody fragments, or pharmaceutical compositions described herein) over an extended period of time (e.g., over a period of at least 1 week, 2 weeks, 3 weeks, 1 month, 2 months, 3 months, 4 months, 5 months, 6 months, 7 months, 8 months, 9 months, 10 months, 11 months, 12 months, 1 year, 2 years, 3 years, 4 years, or 5 years). A skilled medical professional may determine the length of the treatment period using any of the methods described herein for diagnosing or following the effectiveness of treatment (e.g., the observation of at least one symptom of cancer). As described herein, a skilled medical professional can also change the identity and number (e.g., increase or decrease) of antibodies or antigen-binding antibody fragments (and/or one or more additional therapeutic agents) administered to the subject and can also adjust (e.g., increase or decrease) the dosage or frequency of administration of at least one antibody or antigen-binding antibody fragment (and/or one or more additional therapeutic agents) to the subject based on an assessment of the effectiveness of the treatment (e.g., using any of the methods described herein and known in the art).

In some embodiments, one or more additional therapeutic agents can be administered to the subject. The additional therapeutic agent can comprise one or more inhibitors selected from the group consisting of an inhibitor of B-Raf, an EGFR inhibitor, an inhibitor of a MEK, an inhibitor of ERK, an inhibitor of K-Ras, an inhibitor of c-Met, an inhibitor of anaplastic lymphoma kinase (ALK), an inhibitor of a phosphatidylinositol 3-kinase (PI3K), an inhibitor of an Akt, an inhibitor of mTOR, a dual PI3K/mTOR inhibitor, an inhibitor of Bruton's tyrosine kinase (BTK), and an inhibitor of Isocitrate dehydrogenase 1 (IDH1) and/or Isocitrate dehydrogenase 2 (IDH2).

In some embodiments, the additional therapeutic agent can comprise one or more inhibitors selected from the group consisting of an inhibitor of HER3, an inhibitor of LSD1, an inhibitor of MDM2, an inhibitor of BCL2, an inhibitor of CHK1, an inhibitor of activated hedgehog signaling pathway, and an agent that selectively degrades the estrogen receptor.

In some embodiments, the additional therapeutic agent can comprise one or more therapeutic agents selected from the group consisting of Trabectedin, nab-paclitaxel, Trebananib, Cediranib, Palbociclib, everolimus, fluoropyrimidine, IFL, regorafenib, Reolysin® (Pelareorep), Alimta® (Pemetrexed), Zykadia® (Ceritinib), Sutent® (Sunitinib), temsirolimus, axitinib, everolimus, sorafenib, Votrient ° (Pazopanib), IMA-901, AGS-003, cabozantinib, Vinflunine, an Hsp90 inhibitor, Ad-GM-CSF, Temazolomide, IL-2, IFNa, vinblastine, Thalomid, dacarbazine, cyclophosphamide, lenalidomide, azacytidine, lenalidomide, bortezomid, amrubicine, carfilzomib, pralatrexate, and enzastaurin. In some embodiments, the additional therapeutic agent can comprise one or more therapeutic agents selected from the group consisting of an adjuvant, a TLR agonist, tumor necrosis factor (TNF) alpha, IL-1, HMGB1, an IL-10 antagonist, an IL-4 antagonist, an IL-13 antagonist, an IL-17 antagonist, an HVEM antagonist, an ICOS agonist, a treatment targeting CX3CL1, a treatment targeting CXCL9, a treatment targeting CXCL10, a treatment targeting CCL5, an LFA-1 agonist, an ICAM1 agonist, and a Selectin agonist.

In some embodiments, carboplatin, nab-paclitaxel, paclitaxel, cisplatin, pemetrexed, gemcitabine, FOLFOX, or FOLFIRI are administered to the subject.

In some embodiments, the additional therapeutic agent is an anti-PD1 antibody, an anti-PD-L1 antibody, an anti-LAG-3 antibody, an anti-TIGIT antibody, an anti-BTLA antibody, an anti-CTLA-4 antibody, or an anti-GITR antibody.

Methods of modifying and using the anti-OX40 antibodies are described, e.g., in US 20150307617, which is incorporated herein by reference in its entirety.

Pharmaceutical Compositions and Routes of Administration

Also provided herein are pharmaceutical compositions that contain at least one (e.g., one, two, three, or four) of the antibodies or antigen-binding fragments described herein. Two or more (e.g., two, three, or four) of any of the antibodies or antigen-binding fragments described herein can be present in a pharmaceutical composition in any combination. The pharmaceutical compositions may be formulated in any manner known in the art.

Pharmaceutical compositions are formulated to be compatible with their intended route of administration (e.g., intravenous, intraarterial, intramuscular, intradermal, subcutaneous, or intraperitoneal). The compositions can include a sterile diluent (e.g., sterile water or saline), a fixed oil, polyethylene glycol, glycerine, propylene glycol or other synthetic solvents, antibacterial or antifungal agents, such as benzyl alcohol or methyl parabens, chlorobutanol, phenol, ascorbic acid, thimerosal, and the like, antioxidants, such as ascorbic acid or sodium bisulfate, chelating agents, such as ethylenediaminetetraacetic acid, buffers, such as acetates, citrates, or phosphates, and isotonic agents, such as sugars (e.g., dextrose), polyalcohols (e.g., mannitol or sorbitol), or salts (e.g., sodium chloride), or any combination thereof. Liposomal suspensions can also be used as pharmaceutically acceptable carriers (see, e.g., U.S. Pat. No. 4,522,811).

Preparations of the compositions can be formulated and enclosed in ampules, disposable syringes, or multiple dose vials. Where required (as in, for example, injectable formulations), proper fluidity can be maintained by, for example, the use of a coating, such as lecithin, or a surfactant. Absorption of the antibody or antigen-binding fragment thereof can be prolonged by including an agent that delays absorption (e.g., aluminum monostearate and gelatin). Alternatively, controlled release can be achieved by implants and microencapsulated delivery systems, which can include biodegradable, biocompatible polymers (e.g., ethylene vinyl acetate, polyanhydrides, polyglycolic acid, collagen, polyorthoesters, and polylactic acid; Alza Corporation and Nova Pharmaceutical, Inc.).

Compositions containing one or more of any of the antibodies or antigen-binding fragments described herein can be formulated for parenteral (e.g., intravenous, intraarterial, intramuscular, intradermal, subcutaneous, or intraperitoneal) administration in dosage unit form (i.e., physically discrete units containing a predetermined quantity of active compound for ease of administration and uniformity of dosage).

Toxicity and therapeutic efficacy of compositions can be determined by standard pharmaceutical procedures in cell cultures or experimental animals (e.g., monkeys). One can, for example, determine the LD50 (the dose lethal to 50% of the population) and the ED50 (the dose therapeutically effective in 50% of the population): the therapeutic index being the ratio of LD50:ED50. Agents that exhibit high therapeutic indices are preferred. Where an agent exhibits an undesirable side effect, care should be taken to minimize potential damage (i.e., reduce unwanted side effects). Toxicity and therapeutic efficacy can be determined by other standard pharmaceutical procedures.

Data obtained from cell culture assays and animal studies can be used in formulating an appropriate dosage of any given agent for use in a subject (e.g., a human). A therapeutically effective amount of the one or more (e.g., one, two, three, or four) antibodies or antigen-binding fragments thereof (e.g., any of the antibodies or antibody fragments described herein) will be an amount that treats the disease in a subject (e.g., kills cancer cells) in a subject (e.g., a human subject identified as having cancer), or a subject identified as being at risk of developing the disease (e.g., a subject who has previously developed cancer but now has been cured), decreases the severity, frequency, and/or duration of one or more symptoms of a disease in a subject (e.g., a human). The effectiveness and dosing of any of the antibodies or antigen-binding fragments described herein can be determined by a health care professional or veterinary professional using methods known in the art, as well as by the observation of one or more symptoms of disease in a subject (e.g., a human). Certain factors may influence the dosage and timing required to effectively treat a subject (e.g., the severity of the disease or disorder, previous treatments, the general health and/or age of the subject, and the presence of other diseases).

Exemplary doses include milligram or microgram amounts of any of the antibodies or antigen-binding fragments described herein per kilogram of the subject's weight (e.g., about 1 µg/kg to about 500 mg/kg; about 100 µg/kg to about 500 mg/kg; about 100 µg/kg to about 50 mg/kg; about 10 µg/kg to about 5 mg/kg; about 10 µg/kg to about 0.5 mg/kg; or about 1 µg/kg to about 50 µg/kg). While these doses cover a broad range, one of ordinary skill in the art will understand that therapeutic agents, including antibodies and antigen-binding fragments thereof, vary in their potency, and effective amounts can be determined by methods known in the art. Typically, relatively low doses are administered at first, and the attending health care professional or veterinary professional (in the case of therapeutic application) or a researcher (when still working at the development stage) can subsequently and gradually increase the dose until an appropriate response is obtained. In addition, it is understood that the specific dose level for any particular subject will depend upon a variety of factors including the activity of the specific compound employed, the age, body weight, general health, gender, and diet of the subject, the time of administration, the route of administration, the rate of excretion, and the half-life of the antibody or antibody fragment in vivo.

The pharmaceutical compositions can be included in a container, pack, or dispenser together with instructions for administration. The disclosure also provides methods of manufacturing the antibodies or antigen binding fragments thereof for various uses as described herein.

EXAMPLES

The invention is further described in the following examples, which do not limit the scope of the invention described in the claims.

Example 1. Generating Mouse Anti-hOX40 Antibodies

Figure 2:
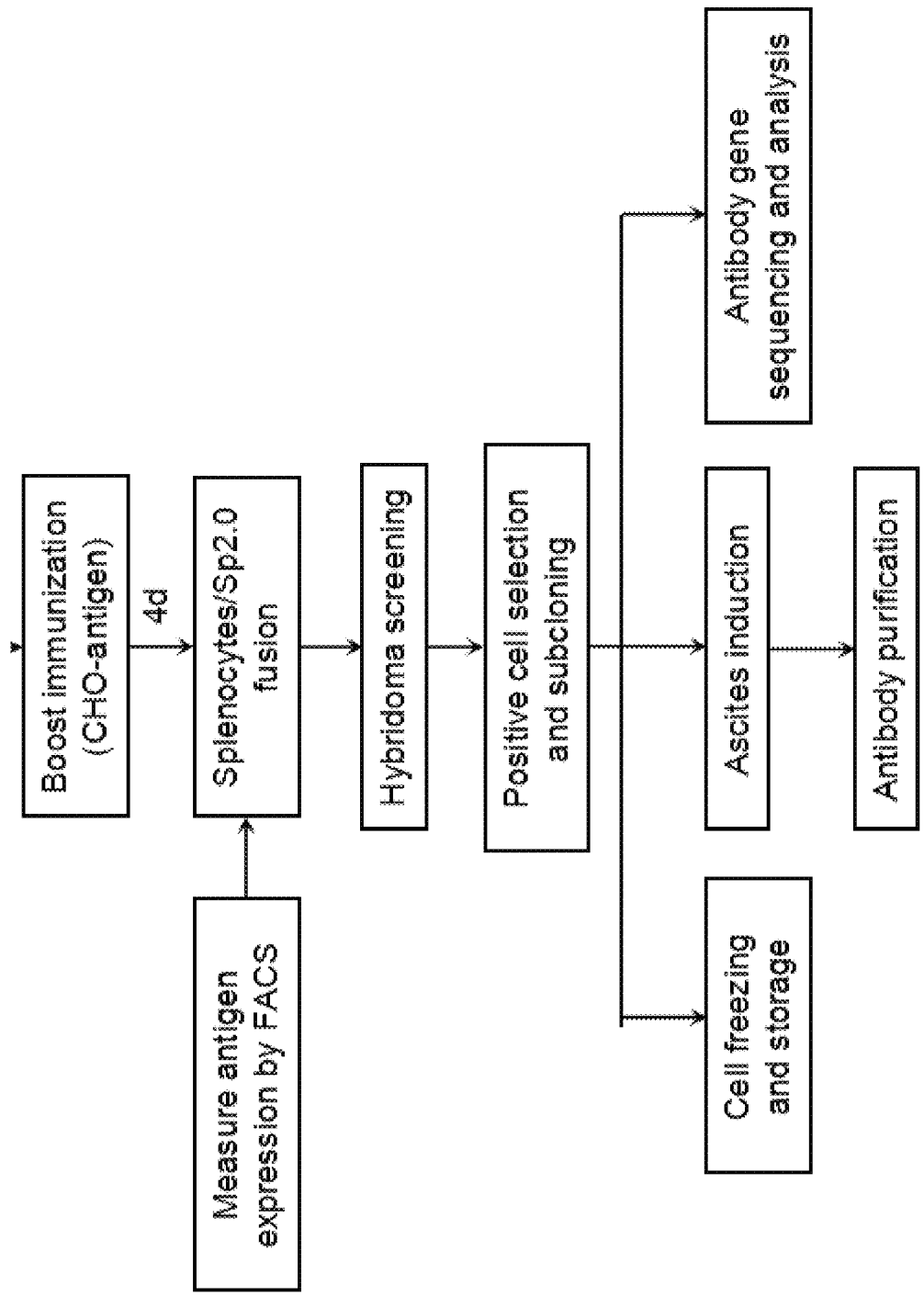
FIG. 2 is a flow chart showing the second part of an exemplary protocol of making anti-OX40 antibodies.

To generate mouse antibodies against human OX40 (hOX40; SEQ ID NO: 49), 6-8 weeks old female BALB/c mice were immunized with human OX40. Anti-hOX40 antibodies were collected by the methods as described below (FIG. 1 and FIG. 2).

Immunization of Mice 6-8 weeks old female BALB/c mice were immunized with His-tagged human OX40 proteins at 20 ug/mouse at a concentration of 100 ug/ml. The His-tagged human OX40 proteins were emulsified with adjuvant and injected at four positions on the back of the mice. For the first subcutaneous (s.c.) injection, the diluted antigen was emulsified with Complete Freund's Adjuvant (CFA) in equal volume. In the following subcutaneous injections, the protein was emulsified with Incomplete Freund's Adjuvant (IFA) in equal volume. Three days after the third injection or the booster immunization, blood (serum) was collected and analyzed for antibody titer using ELISA.

In another experiment, 6-8 weeks old female BALB/c mice were immunized by injecting the expression plasmid encoding human OX40 into the mice. The plasmids encoding the antigen were injected into the tibialis anterior muscle (intramuscular injection; i.m. injection) of the mice by using gene guns at the concentration of 1000 ug/ul at 60 ug per mouse. At least four injections were performed with at least 14 days between each injection. Blood (serum) was collected seven days after the last immunization and the serum was tested for antibody titer by ELISA.

Procedures to enhance immunization were also performed at least fourteen days after the previous immunization (either by injecting the plasmid or by injecting the proteins). CHO cells that express OX40 antigen on the surface were intravenously injected into the mice through tail veins. Spleen was then collected four days after the injection.

Fusion of SP2/0 cells and spleen cells

Spleen tissues were grinded. Spleen cells were first selected by CD3E Microbeads and Anti-Mouse IgM Microbeads, and then fused with SP2/0 cells. The cells were then plated in 96-well plates with hypoxanthine-aminopterin-thymidine (HAT) medium.

Primary Screening of Hybridoma

Primary screening of the hybridoma supernatant in the 96-well plates was performed using Fluorescence-Activated Cell Sorting (FACS) pursuant to standard procedures. Chinese hamster ovary (CHO) cells were added to 96-well plates (2×10 4 cells per well) before the screening. 50 ul of supernatant was used. The antibodies that were used in experiments were (1) Fluorescein (FITC)-conjugated AffiniPure F(ab)$_2$ Fragment Goat Anti-Mouse IgG, Fcγ Fragment Specific, and (2) Alexa Fluor® 647-conjugated AffiniPure F(ab)$_2$ Fragment Goat Anti-Human IgG, Fcγ Fragment Specific.

Sub-Cloning

Sub-cloning was performed using ClonePix® 2. In short, the positive wells identified during the primary screening were transferred to semisolid medium, and IgG positive clones were identified and tested. FITC anti-mouse IgG Fc antibody was used.

Ascites Fluid Antibodies

1×10$^6$ positive hybridoma cells were injected intraperitoneally to B-NDG® mice (Beijing Biocytogen, Beijing, China). Monoclonal antibodies were produced by growing hybridoma cells within the peritoneal cavity of the mouse. The hybridoma cells multiplied and produced ascites fluid in the abdomens of the mice. The fluid contained a high concentration of antibody which can be harvested for later use.

Purification of Antibodies

Antibodies in ascites fluid were purified using GE AKTA protein chromatography (GE Healthcare, Chicago, Illinois, United States). 07-9H3 ("9H3"), 07-9A4 ("9A4"), 11-5C1 ("5C1"), 17-5D10 ("5D10"), 08-6A11 ("6A11") and 14-7F11 ("7F11") were among the mouse antibodies produced by the methods described above.

The VH, VL and CDR regions for some of the antibodies were determined. The heavy chain and light chain CDR1, CDR2, and CDR3 amino acid sequences for 9H3 were shown in SEQ ID NOs: 1-6 (Kabat numbering) or SEQ ID NOs: 25-30 (Chothia numbering).

The heavy chain and light chain CDR1, CDR2, and CDR3 amino acid sequences for 9A4 were shown in SEQ ID NOs: 7-12 (Kabat numbering) or SEQ ID NOs: 31-36 (Chothia numbering).

The heavy chain and light chain CDR1, CDR2, and CDR3 amino acid sequences for 5C1 were shown in SEQ ID NOs: 13-18 (Kabat numbering) or SEQ ID NOs: 37-42 (Chothia numbering).

The heavy chain and light chain CDR1, CDR2, and CDR3 amino acid sequences for 5D10 were shown in SEQ ID NOs: 19-24 (Kabat numbering) or SEQ ID NOs: 43-48 (Chothia numbering).

Example 2. Humanization of the Mice Antibodies

The starting point for humanization was the mouse antibodies (e.g., 9H3, 9A4, 5C1, and 5D10). The amino acid sequences for the heavy chain variable region and the light chain variable region of these mouse antibodies were determined.

Three humanized heavy chain variable region variants (SEQ ID NOs: 53-55) and three humanized light chain variable region variants (SEQ ID NOs: 56-58) for 9H3 were constructed containing different permutations of substitutions.

Three humanized heavy chain variable region variants (SEQ ID NOs: 59-61) and four humanized light chain variable region variants (SEQ ID NOs: 62-65) for 9A4 were constructed containing different permutations of substitutions.

Three humanized heavy chain variable region variants (SEQ ID NOs: 66-68) and four humanized light chain variable region variants (SEQ ID NOs: 69-72) for 5C1 were constructed containing different permutations of substitutions.

Three humanized heavy chain variable region variants (SEQ ID NOs: 73-75) and three humanized light chain variable region variants (SEQ ID NOs: 76-78) for 5D10 were constructed containing different permutations of substitutions.

These humanized heavy chain variable region variants can be combined with any of the corresponding humanized light chain variable region variants. For example, 9H3-H1 (SEQ ID NO: 53) can be combined with any 9H3 humanized light chain variable region variant (e.g., 9H3-K2 (SEQ ID NO: 57)), and the antibody is labeled accordingly (e.g., 9H3-H1K2).

These humanized antibodies were then generated with the use of BioLuminate® 1.0 (Schrodinger, Shanghai, China).

Example 3. In Vitro Testing of the Mouse Anti-hOX40 Antibodies: Blocking the Binding of Human OX40 (hOX40) and Human OX40L (hOX40L)

Blocking assays were performed to determine whether anti-hOX40 antibodies can block the binding between hOX40 and hOX40L.

Anti-hOX40 antibodies were collected from mouse ascites fluid, and were purified by chromatography. 25 ul CHO cells transiently transfected with human OX40 were added to each well in a plate. The purified antibodies were titrated to final concentrations of 50, 5, 0.5, 0.05, 0.005 ug/ml. The titrated antibodies were added to each well at 25 ul per well at 4° C. and incubated for 30 minutes.

hOX40L-Fc was diluted at 1:200. 50 ul of the ligand solution was added to each well. The cells with hOX40L-Fc and the antibodies were incubated at 4° C. for 15 minutes.

After being washed with phosphate-buffered saline (PBS) twice, 50 ul of anti-mouse IgG Fc antibody Phycoerythrin conjugate (anti-mIgG Fc-PE) at 1:500 dilution and anti-human IgG Fc antibody fluorescein isothiocyanate conjugate (anti-hIgG Fc-FITC) at 1:100 dilution were added into each well incubated for 30 minutes at 4° C., followed by PBS wash. The signals for FITC and PE were determined by flow cytometry.

Figure 3:
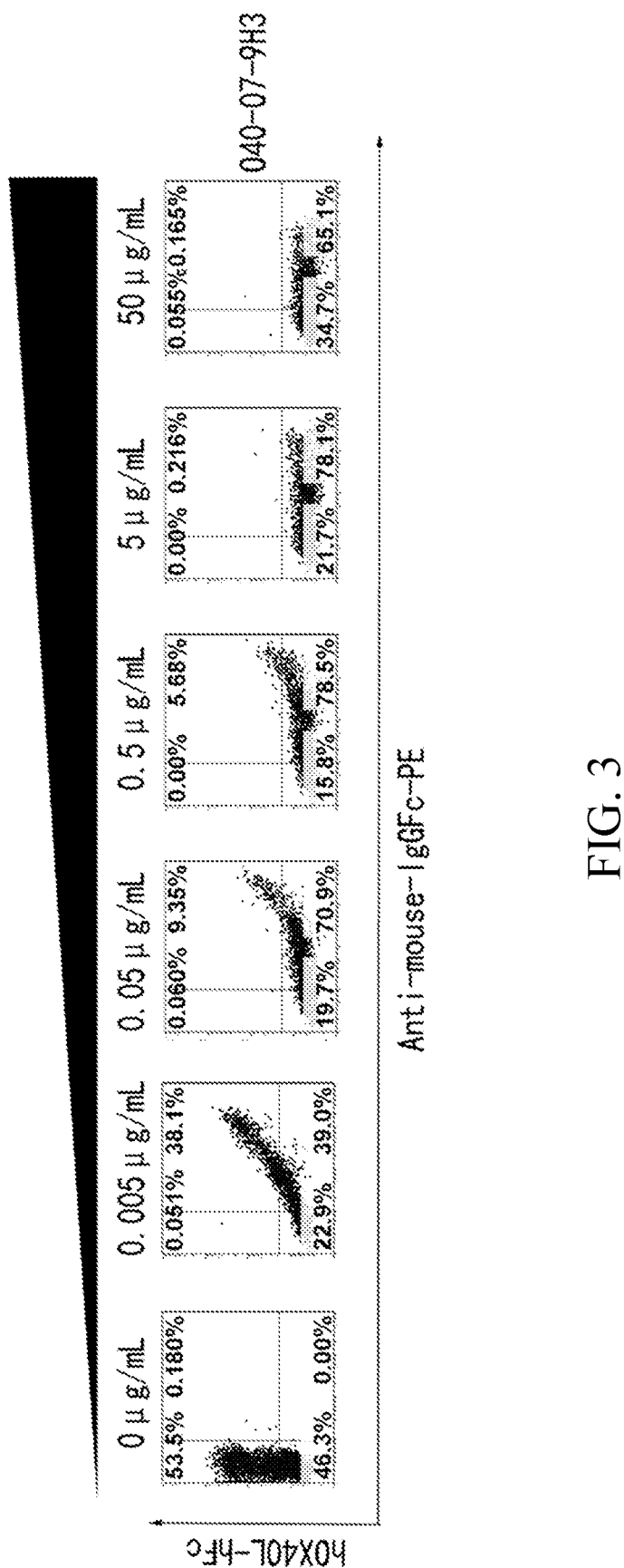
FIG. 3 is a set of flow cytometry graphs showing the anti-OX40 antibodies block the binding between OX40 and OX40L.

As shown in FIG. 3, when the concentration of the mouse anti-hOX40 antibody 9H3 ("07-9H3") increased, the signal for FITC decreased, suggesting that the binding between human OX40 and OX40L was blocked by anti-hOX40 antibodies.

Example 4. Binding Activity of Anti-hOX40 Antibodies to Human OX40

Anti-hOX40 antibodies were collected from mouse ascites fluid, and were purified by chromatography. 25 ul CHO cells transiently transfected with human OX40 were added to each well in a plate. The purified antibodies were titrated to final concentrations of 50, 5, 0.5, 0.05, 0.005 ug/ml. The titrated antibodies were added to each well at 25 ul per well at 4° C. and incubated for 30 minutes.

After being washed with phosphate-buffered saline (PBS) twice, 50 ul of anti-mouse IgG Fc antibody Phycoerythrin conjugate (anti-mIgG Fc-PE) with 1:500 dilution were added into each well, and incubated for 30 minutes at 4° C., followed by PBS wash. The signals for PE were determined by flow cytometry.

Figure 4:
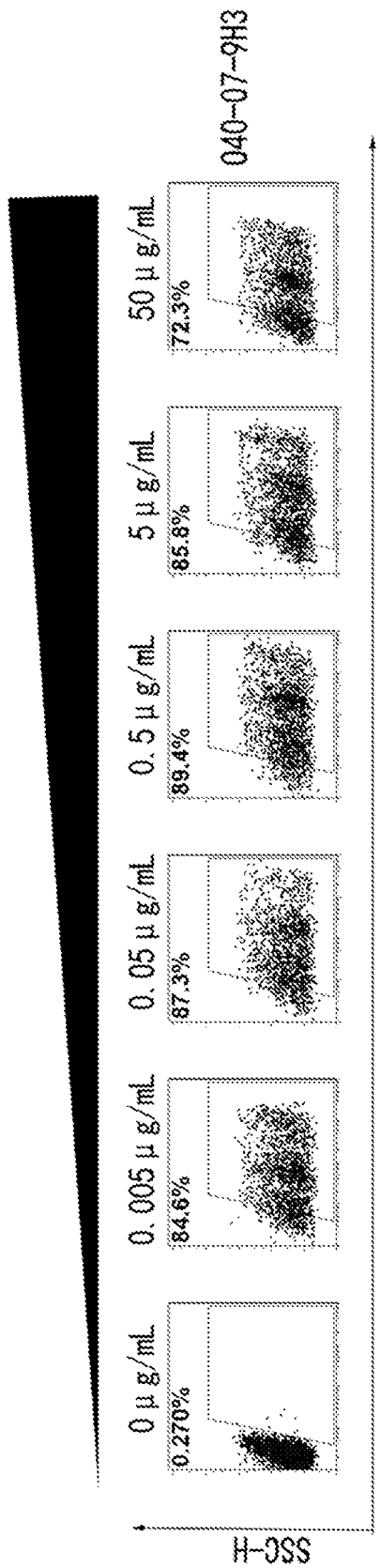
FIG. 4 is a set of flow cytometry graphs showing the anti-OX40 antibodies can bind to human OX40.

As shown in FIG. 4, when the concentration of the mouse anti-hOX40 antibody 9H3 ("07-9H3") increased, the signal for PE increased, suggesting that the 9H3 can bind to human OX40.

Example 5. Cross-Reactivity of Anti-hOX40 Antibodies Against Monkey, Mouse, and Human-Mouse Chimeric OX40 (chiOX40)

CHO cells were transfected with rhesus macaque OX40 (rmOX40, SEQ ID NO: 51), mouse OX40 (mOX40, SEQ ID NO: 50), and chimeric (mouse and human) OX40 (chiOX40, SEQ ID NO: 52).

25 ul CHO cells were added to each well. 25 ul purified anti-hOX40 antibodies (1 ug/ml) (9H3 or "07-9H3") were added to each well and were incubated at 4° C. for 30 minutes.

After being washed with PBS (1200 rmp, 5 min) twice, 50 ul of anti-mouse IgG Fc antibody fluorescein isothiocyanate conjugate (anti-mIgG Fc-FITC) with 1:500 dilution was added into each well and was incubated at 4° C. for 30 minutes, followed by PBS wash (1200 rmp, 5 min). The signals for FITC were determined by flow cytometry.

Figure 5:
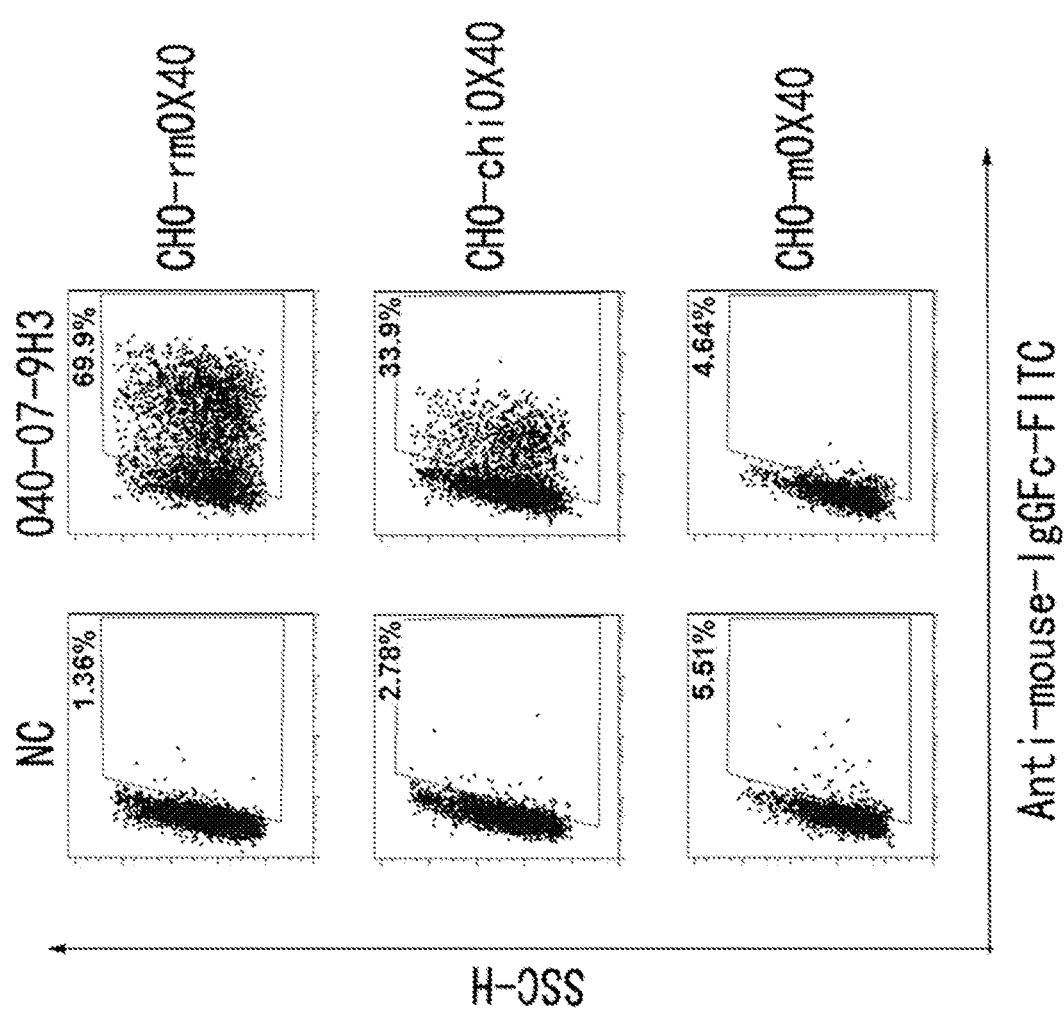
FIG. 5 is a set of graphs showing flow cytometry results of anti-OX40 antibodies' cross-reactivity against monkey (rmOX40), mouse (mOX40), and human-mouse chimeric OX40 (chiOX40).

As shown in FIG. 5, 9H3 did not cross react with mouse OX40, but had strong cross reactivity with rmOX40 and chimeric OX40. In FIG. 5, NC stands for negative control.

Example 6. Bind Affinity of Anti-hOX40 Antibodies

The antibodies were tested for hOX40 binding. The affinity of an antibody was determined by surface plasmon resonance (Biacore™ T200 biosensor, Biacore, INC, Piscataway N.J.) equipped with pre-immobilized Protein A sensor chips.

Figure 6:
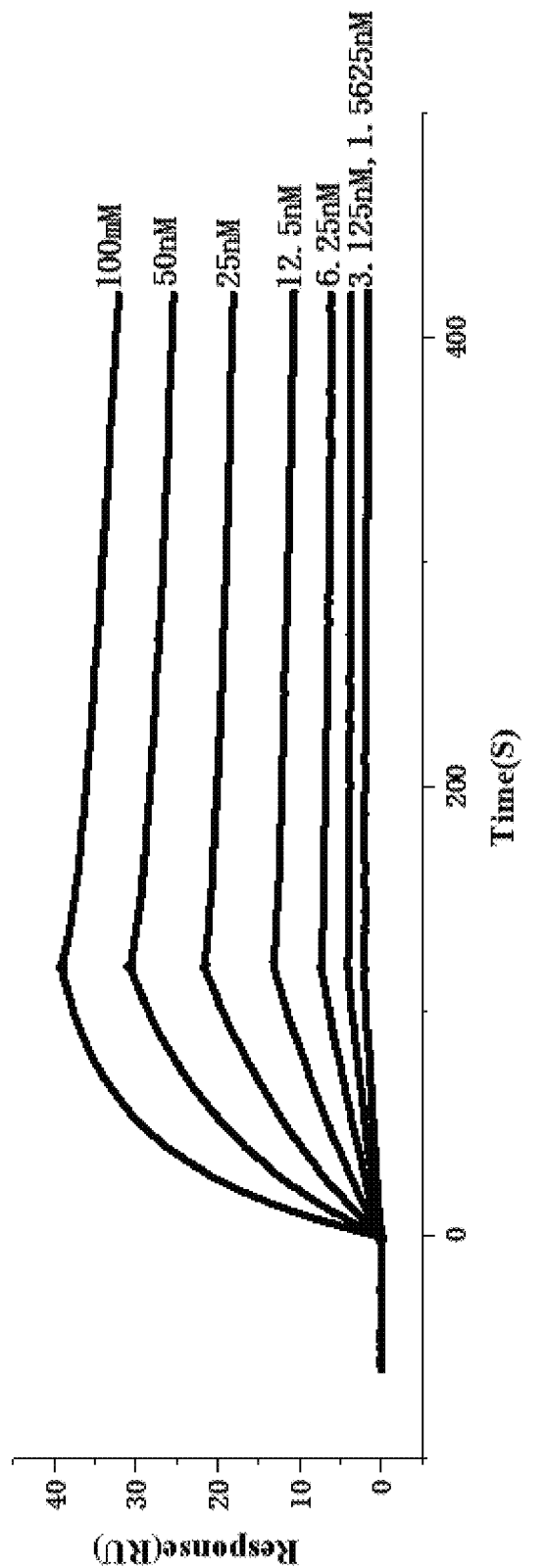
FIG. 6 is a graph showing association rate and disassociation rate between chimeric anti-hOX40 antibody (9H3-mHvKv-IgG1) and human OX40.

Anti-hOX40 antibody 9H3-mHvKv-IgG1 (1 µg/mL) were injected into Biacore™ T200 biosensor at 10 µL/min for 25 seconds to achieve to a desired protein density (about 112 response units (RU)). Human OX40 proteins (hOX40-His)) at the concentration of 100, 50, 25, 12.5, 6.25, 3.125, 1.5625 nM were then injected at 30 µL/min for 120 seconds. Dissociation was monitored for 300 seconds. The chip was regenerated after the last injection of each titration with Glycine (pH 2.0, 30 µL/min for 12 seconds). The result for 9H3-mHvKv-IgG1 was shown in FIG. 6.

Kinetic association rates (kon) and dissociation rates (koff) were obtained simultaneously by fitting the data globally to a 1:1 Langmuir binding model (Karlsson, R. Roos, H. Fagerstam, L. Petersson, B., 1994. Methods Enzymology 6. 99-110) using Biacore™ T200 Evaluation Software 3.0. Affinities were deduced from the quotient of the kinetic rate constants (KD=koff/kon).

The same method with necessary appropriate adjustments for parameters (e.g., concentrations of the antibodies) were performed for all other tested antibodies. The results for the tested anti-hOX40 antibodies are summarized in the table below.

TABLE 1

| Anti-hOX40 antibodies | Association rate kon (1/Ms) | Dissociation rate koff (1/s) | Affinity KD (M) |
|---|---|---|---|
| 9H3-mHvKv-IgG1 | 2.575E+05 | 5.938E-04 | 2.306E-09 |
| 9H3-H2K1-IgG1 | 2.230E+05 | 7.483E-04 | 3.355E-09 |
| 9H3-H2K2-IgG1 | 2.267E+05 | 8.696E-04 | 3.836E-09 |
| 9H3-H2K3-IgG1 | 2.543E+05 | 3.931E-04 | 1.546E-09 |
| 9H3-H3K1-IgG1 | 2.437E+05 | 6.059E-04 | 2.486E-09 |
| 9H3-H3K2-IgG1 | 1.923E+05 | 6.424E-04 | 3.341E-09 |
| 9H3-H3K3-IgG1 | 2.351E+05 | 4.509E-04 | 1.918E-09 |
| 5C1-mHvKv-IgG1 | 5.489E+04 | 1.633E-03 | 2.975E-08 |
| 5D10-mHvKv-IgG1 | 3.171E+05 | 1.474E-02 | 4.649E-08 |
| 9A4-mHvKv-IgG1 | 1.210E+05 | 6.693E-03 | 5.534E-08 |
| 9A4 (mouse antibody) | 8.910E+04 | 1.922E-03 | 2.160E-08 |

Among these tested antibodies, 9A4 is the mouse anti-hOX40 antibody in Example 1. 9H3-mHvKv-IgG1, 5C1-mHvKv-IgG1, 5D10-mHvKv-IgG1, and 9A4-mHvKv-IgG1 are chimeric anti-hOX40 antibodies. They have heavy chain variable domain and light chain variable domain from the mouse anti-hOX40 antibodies, and human IgG1 antibody constant domains (CL, CH1, CH2, CH3).

9H3-H2K1-IgG1, 9H3-H2K2-IgG1, 9H3-H2K3-IgG1, 9H3-H3K1-IgG1, 9H3-H3K2-IgG1, and 9H3-H3K3-IgG1 are humanized antibodies. They have human IgG1 antibody constant domains (CL, CH1, CH2, CH3). The number in the middle indicates the humanized variable domain variants (FIG. 34). For example, 9H3-H2K1-IgG1 has humanized 9H3 heavy chain variable domain H2 (SEQ ID NO: 54) and humanized 9H3 light chain variable domain K1 (SEQ ID NO: 56). Similarly, 9H3-H2K3-IgG1 has humanized 9H3 heavy chain variable domain H2 (SEQ ID NO: 54) and humanized 9H3 light chain variable domain K3 (SEQ ID NO: 58).

Example 7. Thermal Stability of Anti-hOX40 Antibodies

Thermofluor assay analysis was performed using the Protein Thermal Shift™ Dye Kit (Thermo Fisher Scientific) and QuantStudio™ 5 Real Time PCR Systems (Thermo Fisher Scientific). This assay measured thermostability using a fluorescent dye that binds to hydrophobic patches exposed as the protein unfolds.

The experiments were performed according to the manufacturer's protocol. 2 µL of antibody, 10.5 µL of water, 5 µL of Protein Thermal Shift™ buffer, and 2.5 µL of diluted Protein Thermal Shift™ Dye were mixed. Samples were heated to 25° C. at 1.6° C./second, and then heated to 99° C. at 0.05° C./second.

As IgG can be described as a multi-domain protein, the melting curve usually shows two transitions, with a first denaturation temperature, Tm D1, and a second denaturation temperature Tm D2. The presence of these two peaks often indicate the denaturation of the Fc and Fab domains, respectively. However, in some cases, only one peak can be observed.

The table below summarizes the Tm for various anti-hOX40 antibodies. If there were two transitions, Tm D2 was treated as Tm in the table below.

TABLE 2

| Antibody | Variable Domains | Type (constant domains) | Thermal stability (Tm) |
|---|---|---|---|
| 9H3 (mouse antibody) | mHvKv | Mouse IgG | 74.94 |
| 9H3 chimeric antibody | mHvKv | Human IgG1 | 79.12 |
|  |  | Human IgG2 | 79.68 |
|  |  | Human IgG4 | 78.72 |
|  |  | Human IgG1 with N297A mutation | 80.31 |
| 9H3 humanized antibody | H2K1 | Human IgG1 | 73.93 |
|  | H2K2 | Human IgG1 | 74.08 |
|  | H2K3 | Human IgG1 | 73.49 |
|  | H3K1 | Human IgG1 | 81.18 |
|  |  | Human IgG2 | 81.47 |
|  |  | Human IgG4 | 80.59 |
|  |  | Human IgG1-N297A | 81.92 |
|  | H3K3 | Human IgG1 | 81.62 |
|  |  | Human IgG2 | 81.47 |
|  |  | Human IgG4 | 80.29 |
|  |  | Human IgG1-N297A | 81.62 |
| 9A4 chimeric antibody | mHvKv | Human IgG1 | 81.78 |
| 9A4 humanized antibody | H1K1 | Human IgG1 | 85.33 |
|  | H1K2 | Human IgG1 | 84.89 |
|  | H2K1 | Human IgG1 | 84.30 |
|  | H2K2 | Human IgG1 | 83.04 |
| 5C1 chimeric antibody | mHvKv | Human IgG1 | 71.21 |
| 5C1 humanized antibody | H1K1 | Human IgG1 | 82.52 |
|  | H1K2 | Human IgG1 | 82.82 |
|  | H1K3 | Human IgG1 | 82.59 |
|  | H1K4 | Human IgG1 | 83.56 |
|  | H2K2 | Human IgG1 | 83.26 |
|  | H2K3 | Human IgG1 | 82.67 |
|  | H2K4 | Human IgG1 | 83.63 |
|  | H3K1 | Human IgG1 | 79.12 |
|  | H3K2 | Human IgG1 | 79.64 |
|  | H3K3 | Human IgG1 | 79.12 |
|  | H3K4 | Human IgG1 | 79.93 |
| 5D10 chimeric antibody | mHvKv | Human IgG1 | 74.39 |
| 5D10 humanized antibody | H1K1 | Human IgG1 | 86.51 |
|  | H1K2 | Human IgG1 | 87.10 |
|  | H2K1 | Human IgG1 | 86.59 |
|  | H2K2 | Human IgG1 | 87.10 |

In Table 2, except for 9H3 mouse antibody, all antibodies are either chimeric antibodies or humanized antibodies. The name and the sequences for these antibodies are listed below. The name indicates the source, the variable region, and constant region of the antibody. For example, a humanized 5D10 antibody with humanized heavy chain variable region H1 and humanized light chain variable region K1 and human IgG1 constant regions is labeled as 5D10-H1K1-IgG1 in the present disclosure. Similarly, a 5C1 chimeric antibody with mouse VH and VL, and human IgG1 constant regions are labeled as 5C1-mHvKv-IgG1. Furthermore, to reduce glycan heterogeneity, the Fc region of some antibodies was further engineered to replace the Asparagine at position 297 with Alanine (N297A).

TABLE 3

| Type | Antibody name | VH SEQ ID NO: | VL SEQ ID NO: | Constant regions |
|---|---|---|---|---|
| 9H3 chimeric antibody | 9H3-mHvKv-IgG1 | 79 | 80 | Human IgG1 |
| | 9H3-mHvKv-IgG2 | 79 | 80 | Human IgG2 |
| | 9H3-mHvKv-IgG4 | 79 | 80 | Human IgG4 |
| | 9H3-mHvKv-IgG1-N297A | 79 | 80 | Human IgG1 with N297A mutation |
| 9H3 humanized antibody | 9H3-H2K1-IgG1 | 54 | 56 | Human IgG1 |
| | 9H3-H2K2-IgG1 | 54 | 57 | Human IgG1 |
| | 9H3-H2K3-IgG1 | 54 | 58 | Human IgG1 |
| | 9H3-H3K1-IgG1 | 55 | 56 | Human IgG1 |
| | 9H3-H3K1-IgG2 | 55 | 56 | Human IgG2 |
| | 9H3-H3K1-IgG4 | 55 | 56 | Human IgG4 |
| | 9H3-H3K1-IgG1-N297A | 55 | 56 | Human IgG1 with N297A mutation |
| | 9H3-H3K2-IgG1 | 55 | 57 | Human IgG1 |
| | 9H3-H3K3-IgG1 | 55 | 58 | Human IgG1 |
| | 9H3-H3K3-IgG2 | 55 | 58 | Human IgG2 |
| | 9H3-H3K3-IgG4 | 55 | 58 | Human IgG4 |
| | 9H3-H3K3--IgG1-N297A | 55 | 58 | Human IgG1 with N297A mutation |
| 9A4 chimeric antibody | 9A4-mHvKv-IgG1 | 81 | 82 | Human IgG1 |
| 9A4 humanized antibody | 9A4-H1K1-IgG1 | 59 | 62 | Human IgG1 |
| | 9A4-H1K2-IgG1 | 59 | 63 | Human IgG1 |
| | 9A4-H2K1-IgG1 | 60 | 62 | Human IgG1 |
| | 9A4-H2K2-IgG1 | 60 | 63 | Human IgG1 |
| 5C1 chimeric antibody | 5C1-mHvKv-IgG1 | 83 | 84 | Human IgG1 |
| 5C1 humanized antibody | 5C1-H1K1-IgG1 | 66 | 69 | Human IgG1 |
| | 5C1-H1K2-IgG1 | 66 | 70 | Human IgG1 |
| | 5C1-H1K3-IgG1 | 66 | 71 | Human IgG1 |
| | 5C1-H1K4-IgG1 | 66 | 72 | Human IgG1 |
| | 5C1-H2K2-IgG1 | 67 | 70 | Human IgG1 |
| | 5C1-H2K3-IgG1 | 67 | 71 | Human IgG1 |
| | 5C1-H2K4-IgG1 | 67 | 72 | Human IgG1 |
| | 5C1-H3K1-IgG1 | 68 | 69 | Human IgG1 |
| | 5C1-H3K2-IgG1 | 68 | 70 | Human IgG1 |
| | 5C1-H3K3-IgG1 | 68 | 71 | Human IgG1 |
| | 5C1-H3K4-IgG1 | 68 | 72 | Human IgG1 |
| 5D10 chimeric antibody | 5D10-mHvKv-IgG1 | 85 | 86 | Human IgG1 |
| 5D10 humanized antibody | 5D10-H1K1-IgG1 | 73 | 76 | Human IgG1 |
| | 5D10-H1K2-IgG1 | 73 | 77 | Human IgG1 |
| | 5D10-H2K1-IgG1 | 74 | 76 | Human IgG1 |
| | 5D10-H2K2-IgG1 | 74 | 77 | Human IgG1 |

Two transitions were observed in some of the tested antibodies. The results for Tm D1 and Tm D2 for some of the tested antibodies are shown in the tables below.

TABLE 4

| Antibodies | Tm D1 | Tm D2 |
|---|---|---|
| 9H3-H2K1-IgG1 | None* | 73.93 |
| 9H3-H2K2-IgG1 | None* | 74.08 |
| 9H3-H2K3-IgG1 | None* | 73.49 |
| 9H3-H3K2-IgG1 | 70.68 | 81.18 |

*Only one transition curve was observed.

The result shows that 9H3-H2K1-IgG1, 9H3-H2K2-IgG1, and 9H3-H2K3-IgG1 have much lower Tm D2 than some other antibodies (e.g., 9H3-H3K2-IgG1). It is possible that the 9H3 humanized heavy chain H2 (SEQ ID NO: 54) are not as stable as other humanized heavy chains. This result was also consistent with thermal stability results from CHO-S supernatant (containing expressed antibodies) as determined by FACS.

TABLE 5

| Antibodies | Tm D1 | Tm D2 |
|---|---|---|
| 9H3-H3K1-IgG1 | 70.09 | 81.18 |
| 9H3-H3K1-IgG1-N297A | 61.37 | 81.92 |
| 9H3-H3K1-IgG2 | 69.65 | 81.47 |
| 9H3-H3K1-IgG4 | 65.65 | 80.59 |

TABLE 6

| Antibodies | Tm D1 | Tm D2 |
|---|---|---|
| 9H3-H3K3-IgG1 | 70.09 | 81.62 |
| 9H3-H3K3-IgG1-297N/A | 61.37 | 81.62 |
| 9H3-H3K3-IgG2 | 69.65 | 81.47 |
| 9H3-H3K3-IgG4 | 66.25 | 80.29 |

The results in Table 5 and Table 6 show that humanized antibodies with IgG1 constant regions and IgG2 constant regions had similar Tm D1 and had similar Tm D2. The mutation N297A in IgG1 can significantly reduce Tm D1, but not Tm D2. Furthermore, humanized antibodies with IgG4 constant regions had lower Tm D1 and Tm D2.

Example 8. In Vivo Testing of Mouse and Chimeric Anti-hOX40 Antibodies

In order to test the anti-hOX40 antibodies in vivo and to predict the effects of these antibodies in human body, an OX40 humanized mouse model was generated. The OX40 humanized mouse model was engineered to express a chimeric OX40 protein (SEQ ID NO: 52) wherein a part of the extracellular region of the mouse OX40 protein was replaced by the human OX40 extracellular region. The amino acid residues 31-195 of mouse OX40 (SEQ ID NO: 50) were replaced by amino acid residues 35-197 of human OX40 (SEQ ID NO:49). The humanized mouse model (B-hOX40 humanized mice) provides a new tool for testing new therapeutic treatments in a clinical setting by significantly decreasing the difference between clinical outcome in human and in ordinary mice expressing mouse OX40. A detailed description regarding OX40 humanized mouse model can be found in PCT/CN2017/099575, which is incorporated herein by reference in its entirety.

The anti-hOX40 antibodies were tested to demonstrate their effect on tumor growth in vivo in a model of colon carcinoma. MC-38 cancer tumor cells (colon adenocarcinoma cell) were injected subcutaneously in B-hOX40 humanized mice. When the tumors in the mice reached a volume of 150±50 mm$^3$, the mice were randomly placed into different groups based on the volume of the tumor.

The mice were then injected with Physiological saline (PS) and anti-hOX40 antibodies by intraperitoneal administration. The antibody was given on the first day and the fourth day of each week for 3 weeks (6 injections in total).

The injected volume was calculated based on the weight of the mouse at 3 mg/kg. The length of the long axis and short axis of the tumor was measured and the volume of the tumor was calculated as 0.5×(long axis)×(short axis). The weight of the mice was also measured before the injection, when the mice were placed into different groups (before the first antibody injection), twice a week during the antibody injection period, and before euthanization.

The tumor growth inhibition percentage (TGI %) was calculated using the following formula: TGI (%)=[1−(Ti−T0)/(Vi−V0)]×100. Ti is the average tumor volume in the treatment group on day i. T0 is the average tumor volume in the treatment group on day zero. Vi is the average tumor volume in the control group on day i. V0 is the average tumor volume in the control group on day zero.

T-test was performed for statistical analysis. A TGI % higher than 60% indicates significant suppression of tumor growth. P<0.05 is a threshold to indicate significant difference.

Figure 7:
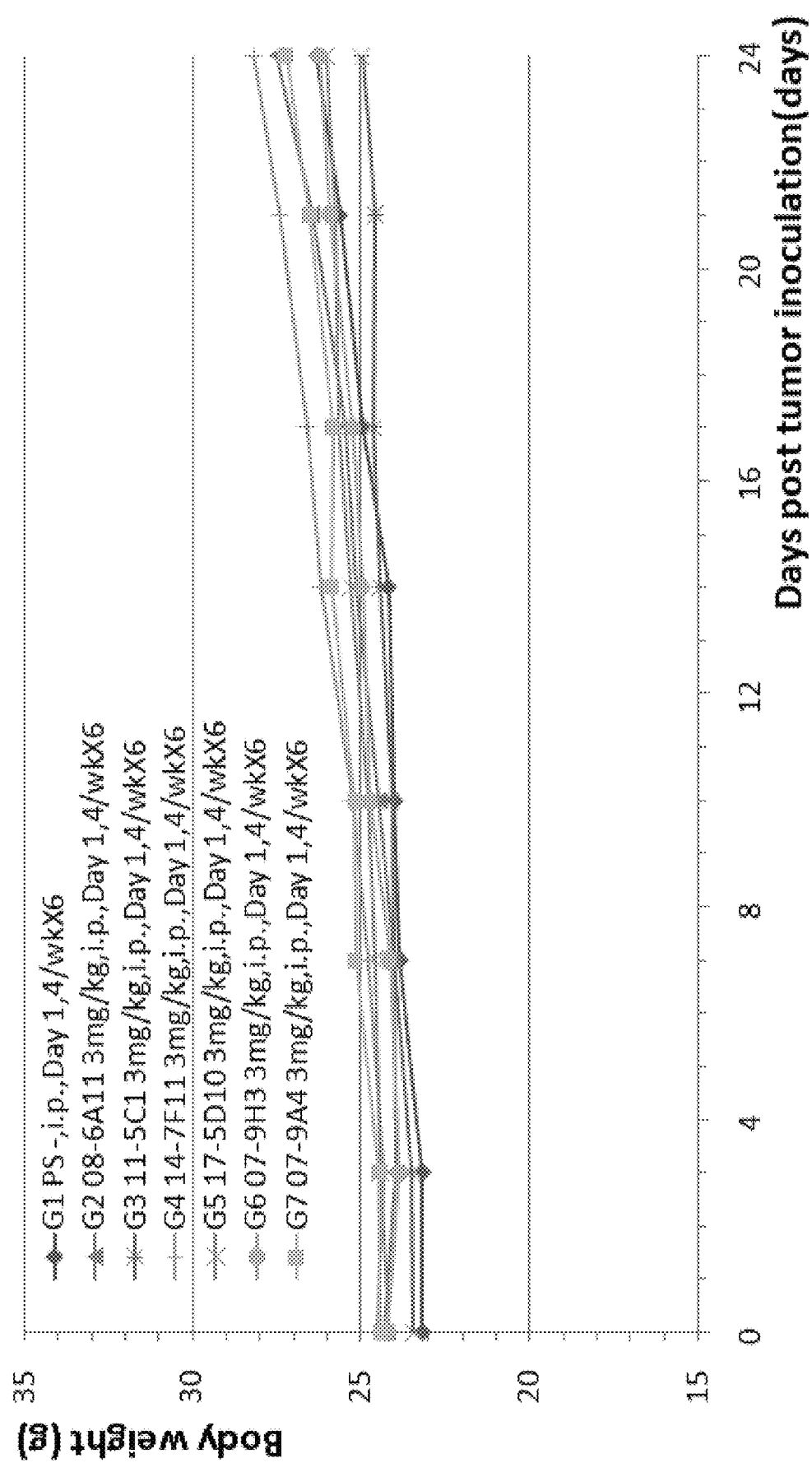
FIG. 7 is a graph showing body weight over time of OX40 humanized mice (B-hOX40) with MC-38 tumor cells treated with mouse anti-hOX40 antibodies 07-9H3, 07-9A4, 11-5C1, 17-5D10, 08-6A11, and 14-7F11.
Figure 8:
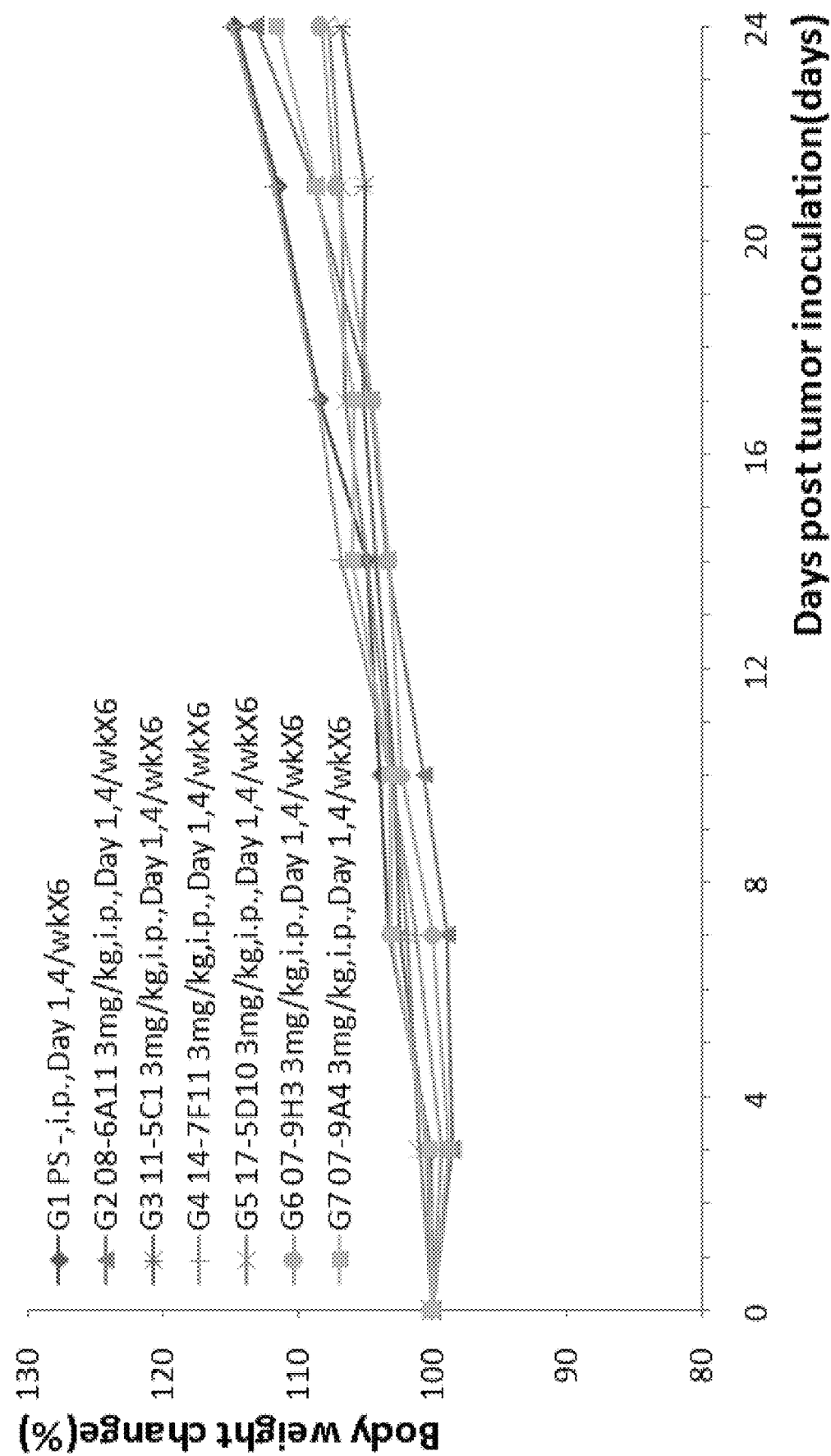
FIG. 8 is a graph showing percentage change of body weight over time of OX40 humanized mice (B-hOX40) with MC-38 tumor cells treated with mouse anti-hOX40 antibodies 07-9H3, 07-9A4, 11-5C1, 17-5D10, 08-6A11, and 14-7F11.

In vivo results for mouse anti-hOX40 antibodies 07-9H3, 07-9A4, 11-5C1, 17-5D10, 08-6A11, and 14-7F11 Mouse anti-hOX40 antibodies 07-9H3, 07-9A4, 11-5C1, 17-5D10, 08-6A11, and 14-7F11 were administered to B-hOX40 humanized mice (OX40 humanized mice). The weight of the mice was monitored during the entire treatment period. The weight of mice in different groups all increased (FIG. 7, and FIG. 8). No significant difference in weight was observed between the control group and the anti-hOX40 treatment groups. The results showed that anti-hOX40 antibodies were well tolerated and not toxic to the mice.

Figure 9:
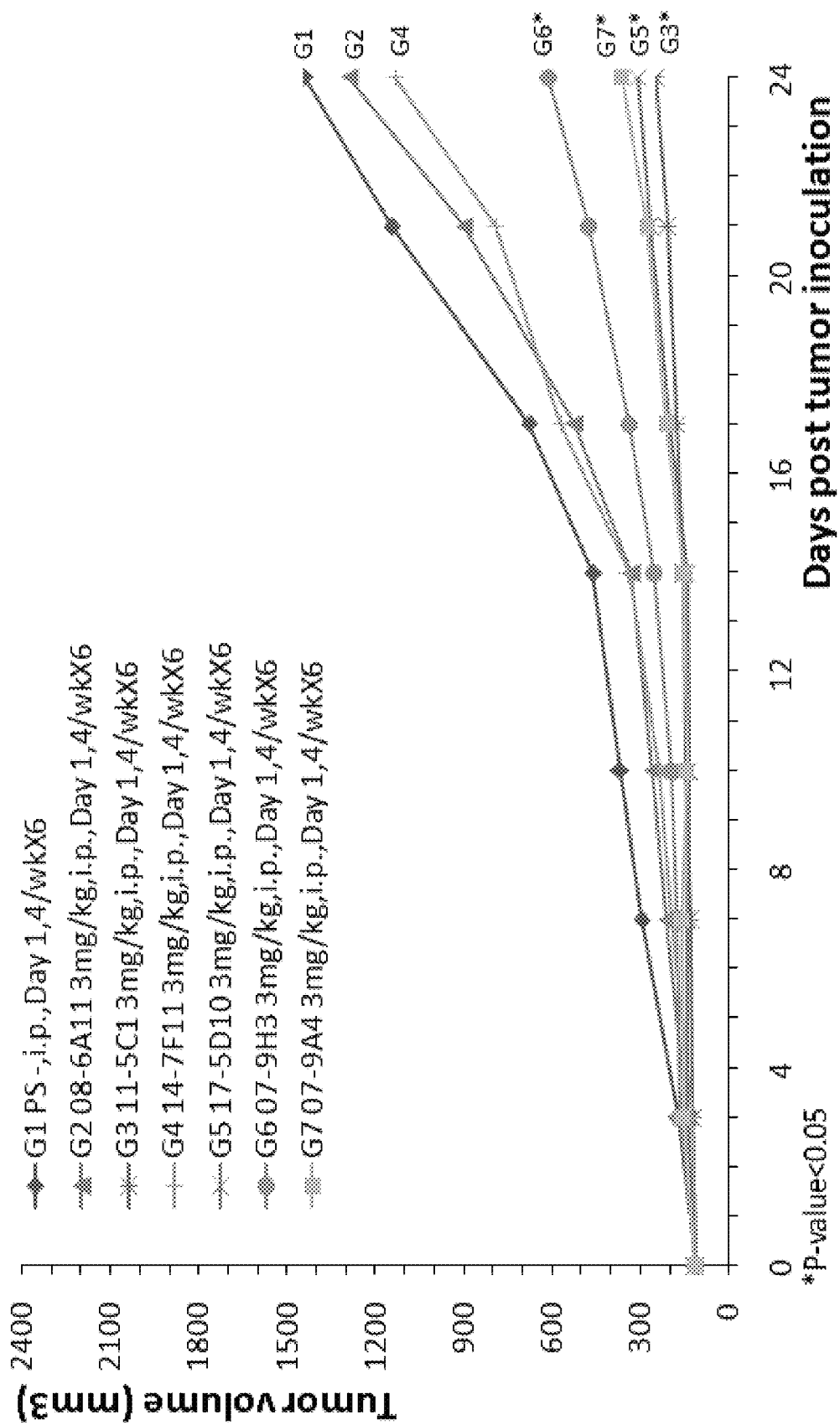
FIG. 9 is a graph showing tumor size over time in OX40 humanized mice (B-hOX40) with MC-38 tumor cells treated with mouse anti-hOX40 antibodies 07-9H3, 07-9A4, 11-5C1, 17-5D10, 08-6A11, and 14-7F11.

The tumor size, however, showed significant difference in groups treated with antibodies 07-9H3, 07-9A4, 11-5C1, and 17-5D10. (FIG. 9).

The TGI % at day 24 for each treatment group was also calculated as shown in the table below.

TABLE 7

| Group | Antibodies | Average tumor size at Day 24 | TGI % | P value |
|---|---|---|---|---|
| G1 | PS | 1441 | — | — |
| G2 | 08-6A11 (3 mg/kg) | 1288 | 11.5% | 0.704 |
| G3 | 11-5C1 (3 mg/kg) | 248 | 90.0% | 0.005 |
| G4 | 14-7F11 (3 mg/kg) | 1133 | 23.3% | 0.403 |
| G5 | 17-5D10 (3 mg/kg) | 311 | 85.3% | 0.010 |
| G6 | 07-9H3 (3 mg/kg) | 614 | 62.4% | 0.031 |
| G7 | 07-9A4 (3 mg/kg) | 366 | 81.1% | 0.010 |

The result shows that 5C1 had the best TGI %. 6A11 and 7F11 were not effective in inhibiting tumor growth.

In Vivo Results for Chimeric Anti-hOX40 Antibodies

Mouse anti-hOX40 antibody 9H3, and chimeric anti-hOX40 antibodies 9H3-mHvKv-IgG1, 9H3-mHvKv-IgG2, 9H3-mHvKv-IgG4, and 9H3-mHvKv-IgG1-N297A were administered into B-hOX40 humanized mice (humanized OX40 mice) by intraperitoneal administration. The injected amount was calculated based on the weight of the mouse at 3 mg/kg. The antibody was given on the first day and the fourth day of each week (5 injections in total).

Figure 10:
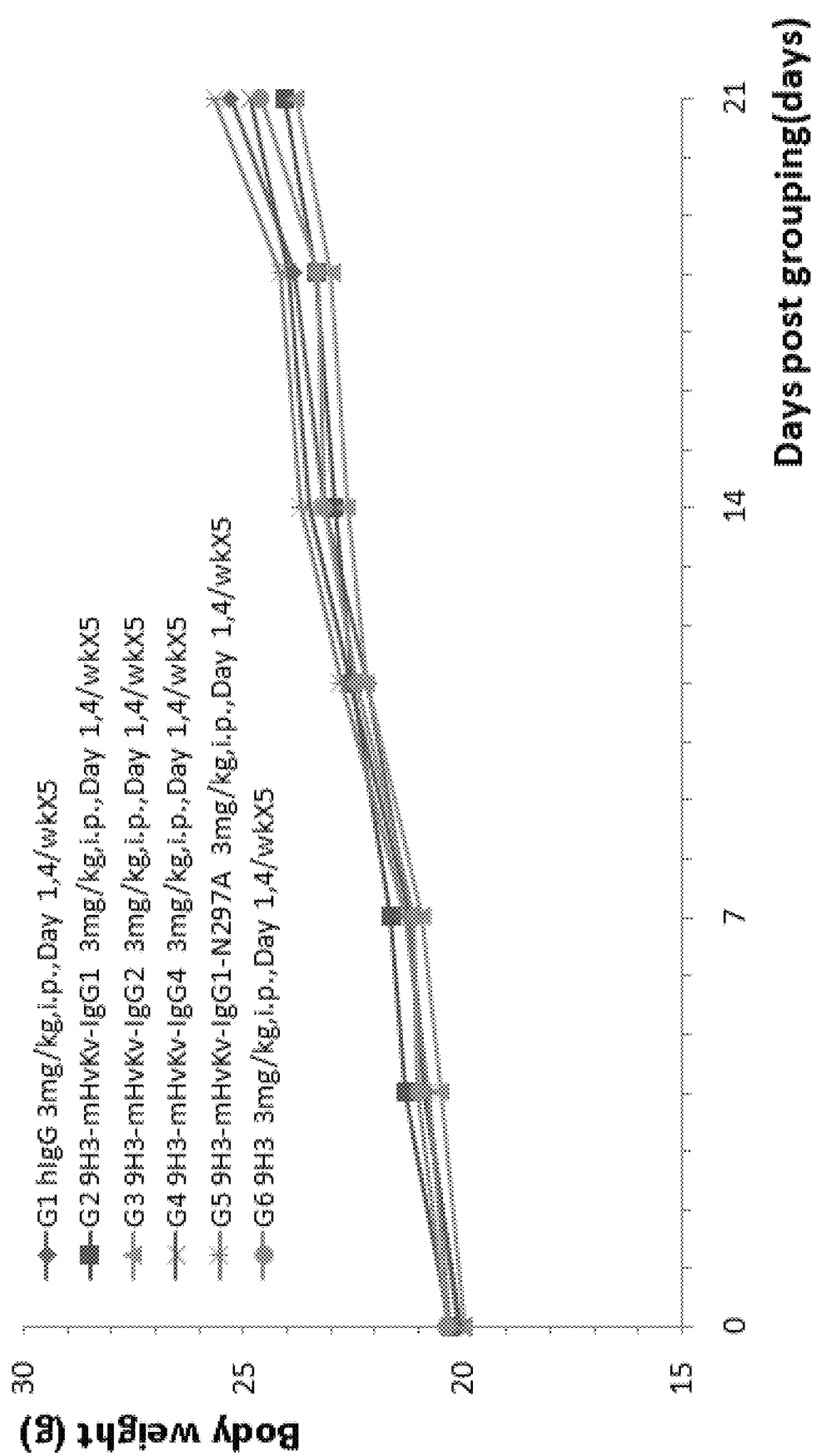
FIG. 10 is a graph showing body weight over time of OX40 humanized mice (B-hOX40) with MC-38 tumor cells treated with chimeric anti-hOX40 antibodies.
Figure 11:
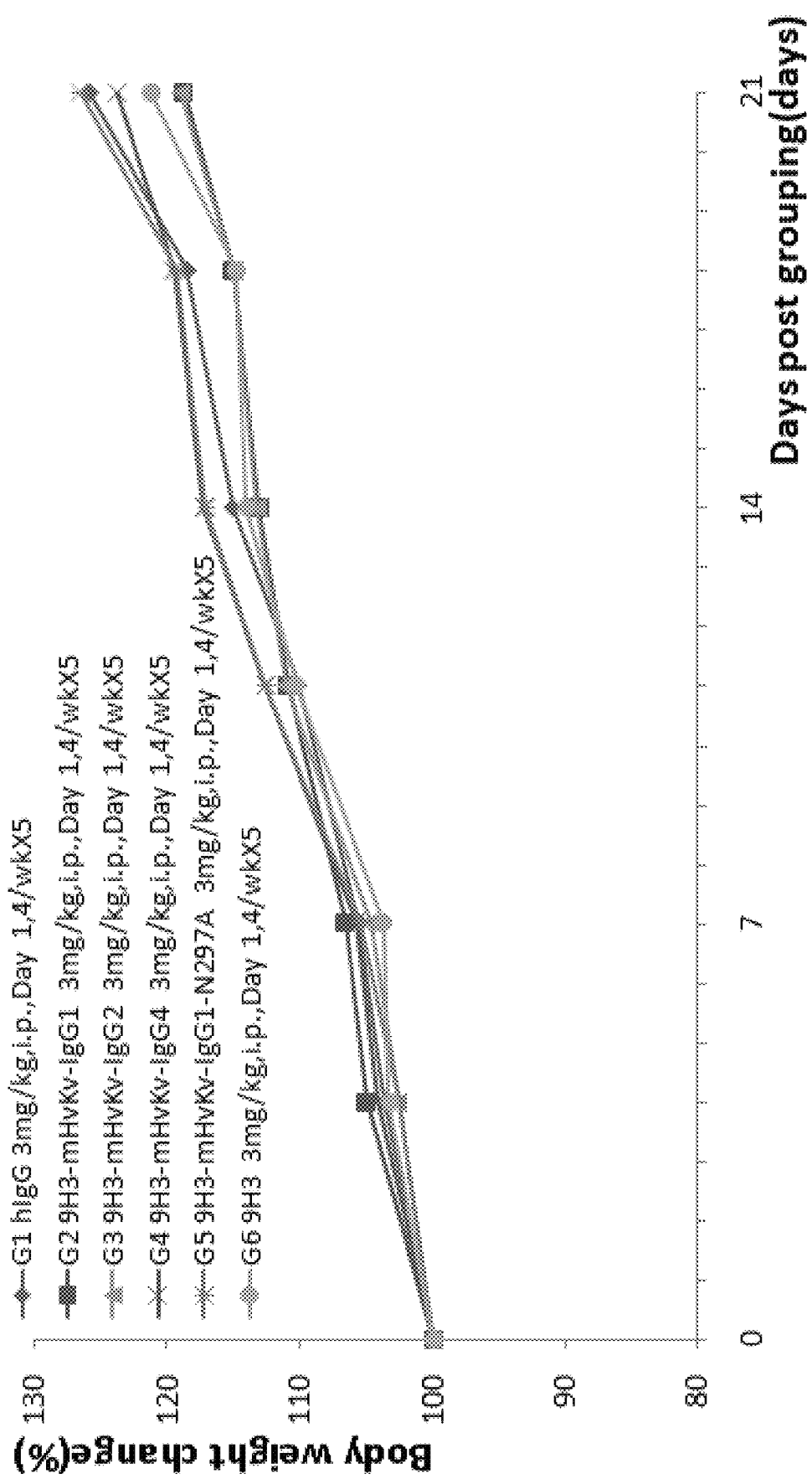
FIG. 11 is a graph showing percentage change of body weight over time of OX40 humanized mice (B-hOX40) with MC-38 tumor cells treated with chimeric anti-hOX40 antibodies.

The weight of the mice was monitored during the entire treatment period. The weight of mice in different groups all increased (FIG. 10, and FIG. 11). No significant difference in weight was observed between the control group and the anti-hOX40 treatment groups. The results showed that anti-hOX40 antibodies were well tolerated and not toxic to the mice.

Figure 12:
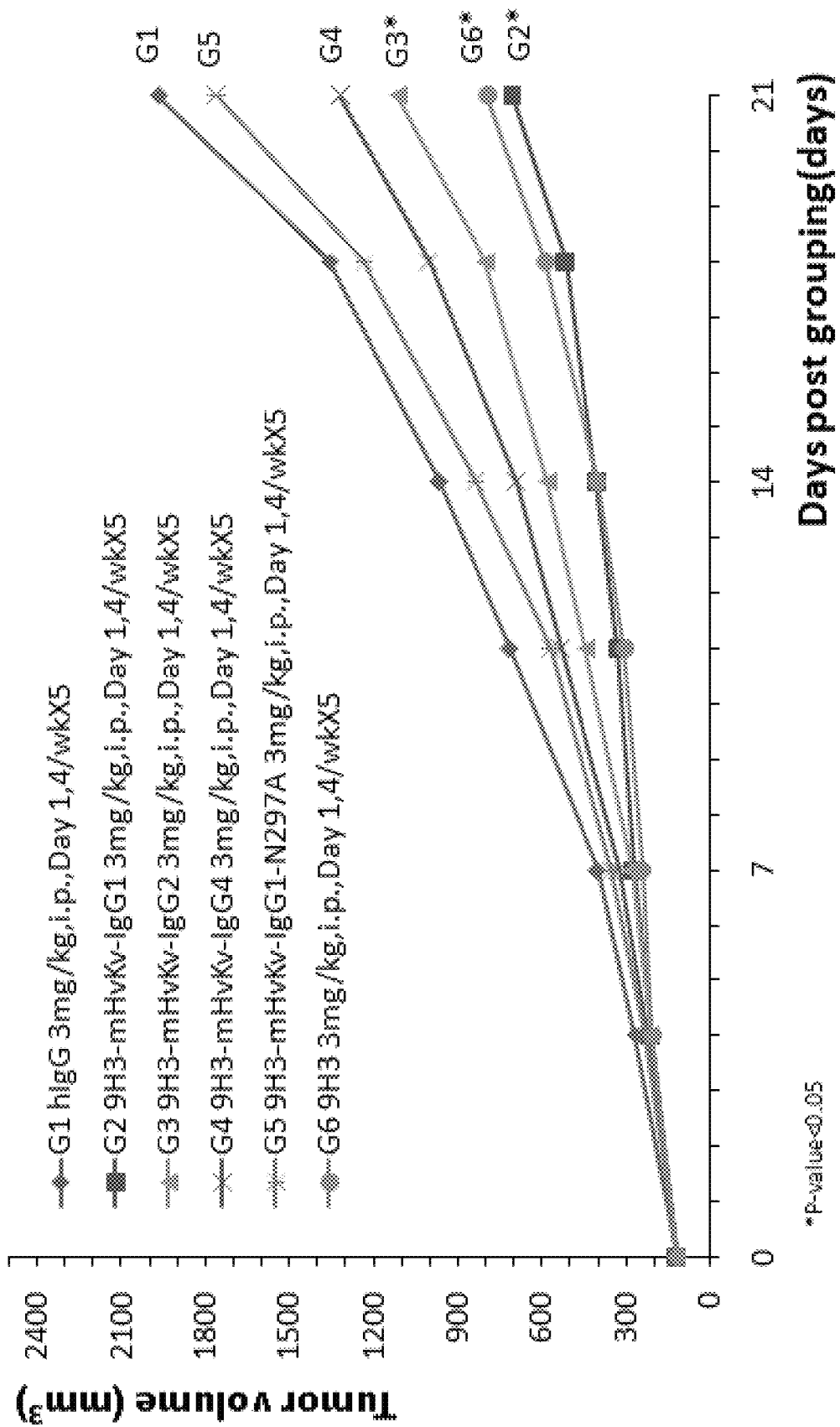
FIG. 12 is a graph showing tumor size over time in OX40 humanized mice (B-hOX40) with MC-38 tumor cells treated with chimeric anti-hOX40 antibodies.

The tumor size, however, showed significant difference in groups treated with antibodies 9H3-mHvKv-IgG1, 9H3-mHvKv-IgG2, 9H3-mHvKv-IgG4, and 9H3-mHvKv-IgG1-N297A (FIG. 12).

The TGI % at day 21 for each treatment group was also calculated as shown in the table below.

TABLE 8

| Group | Antibodies | Average tumor size at Day 21 | TGI % | P value |
|---|---|---|---|---|
| G1 | PS | 1971 | — | — |
| G2 | 9H3-mHvKv-IgG1 (3 mg/kg; i.p. administration; twice a week; 5 injections in total) | 706 | 68.3% | 0.009 |
| G3 | 9H3-mHvKv-IgG2 (3 mg/kg; i.p. administration; twice a week; 5 injections in total) | 1117 | 46.1% | 0.031 |
| G4 | 9H3-mHvKv-IgG4 (3 mg/kg; i.p. administration; twice a week; 5 injections in total) | 1323 | 35.0% | 0.117 |
| G5 | 9H3-mHvKv-IgG1-N297A (3 mg/kg; i.p. administration; twice a week; 5 injections in total) | 1760 | 11.4% | 0.573 |
| G6 | 9H3 (3 mg/kg; i.p. administration; twice a week; 5 injections in total) | 794 | 63.5% | 0.003 |

The results show that mouse anti-hOX40 antibody 9H3, and chimeric anti-hOX40 antibody 9H3-mHvKv-IgG1 and 9H3-mHvKv-IgG2 can significantly inhibit tumor growth. Among them, 9H3-mHvKv-IgG1 had the highest TGI %.

Example 9. In Vivo Testing of Humanized Anti-hOX40 Antibodies

The humanized anti-hOX40 antibodies were tested in OX40 humanized mice to demonstrate their effect on tumor growth in vivo.

MC-38 cancer tumor cells (colon adenocarcinoma cell) were injected subcutaneously in B-hOX40 humanized mice. When the tumors in the mice reached a volume of 150±50 mm$^3$, the mice were randomly placed into different groups based on the volume of the tumor (8 mice in each group).

The mice were then injected with human IgG (control) and anti-hOX40 antibodies by intraperitoneal injection at either 3 mg/kg or 1 mg/kg. The antibody was given on the first day and the fourth day of each week for 3 weeks (6 injections in total).

Figure 13:
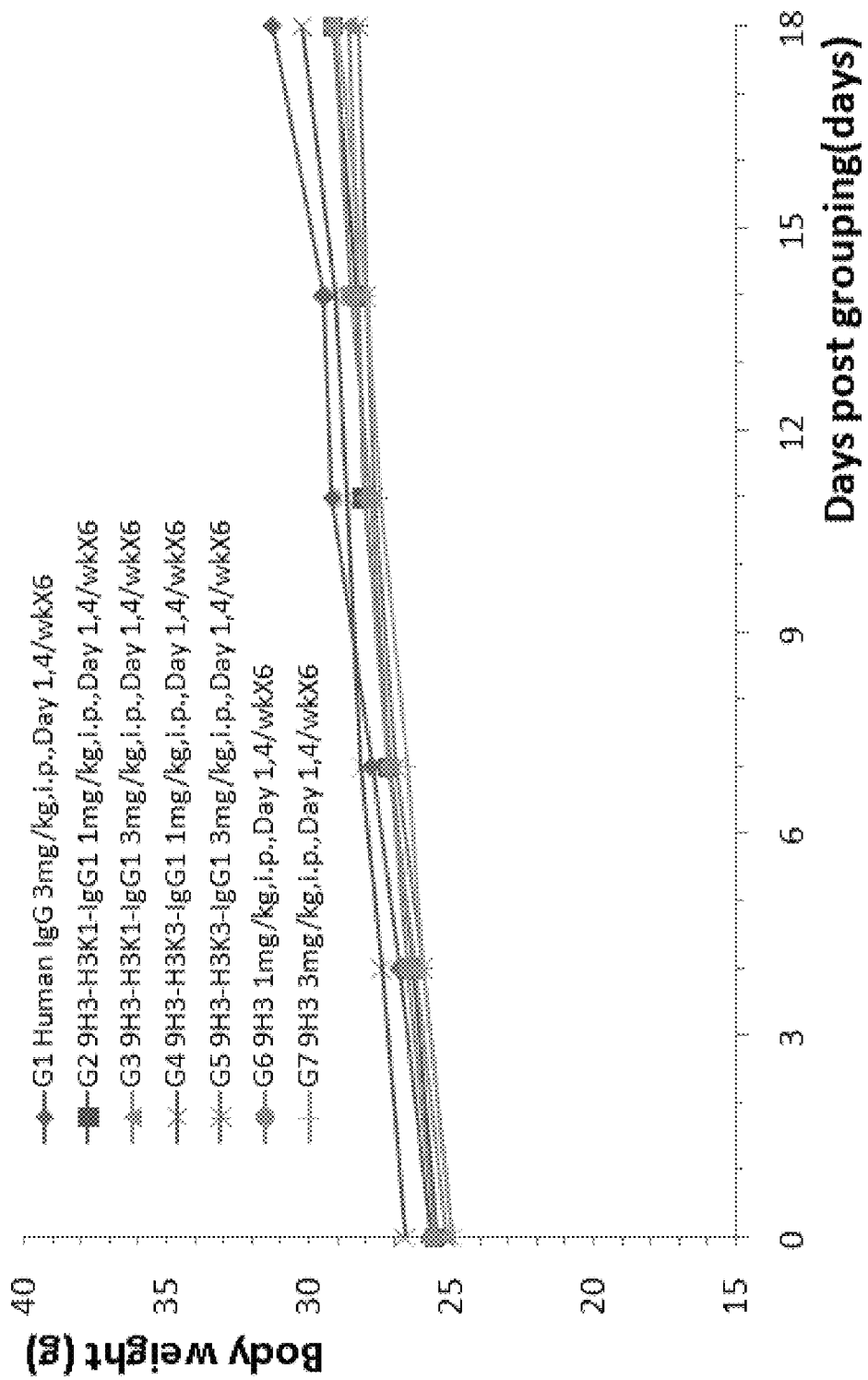
FIG. 13 is a graph showing body weight over time of OX40 humanized mice (B-hOX40) with MC-38 tumor cells treated with humanized anti-hOX40 antibodies.
Figure 14:
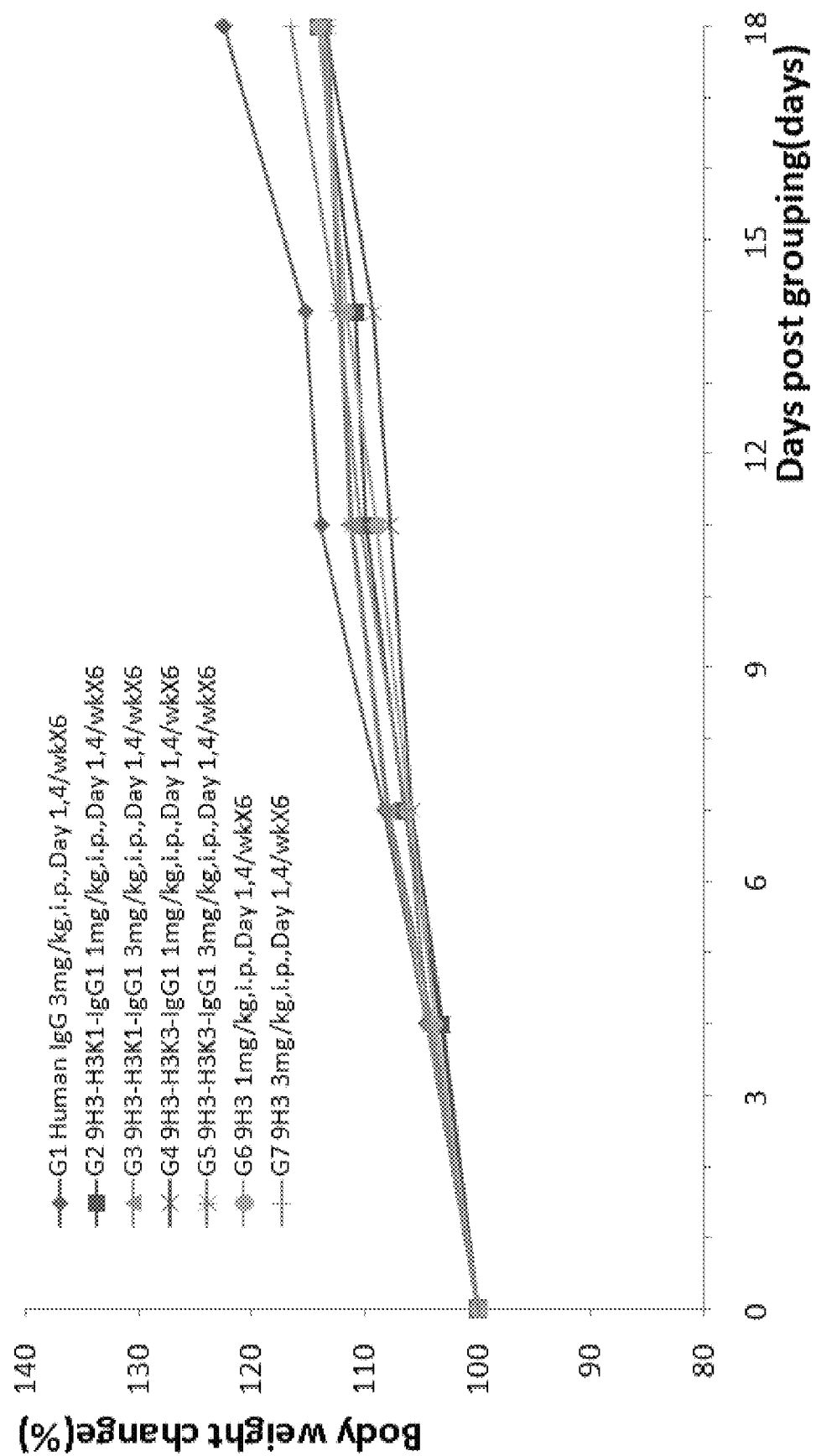
FIG. 14 is a graph showing percentage change of body weight over time of OX40 humanized mice (B-hOX40) with MC-38 tumor cells treated humanized anti-hOX40 antibodies.

The weight of the mice was monitored during the entire treatment period. The weight of mice in different groups all increased (FIG. 13, and FIG. 14). No significant difference in weight was observed between the control group and the anti-hOX40 treatment groups. The results showed that anti-hOX40 antibodies were well tolerated and not toxic to the mice.

Figure 15:
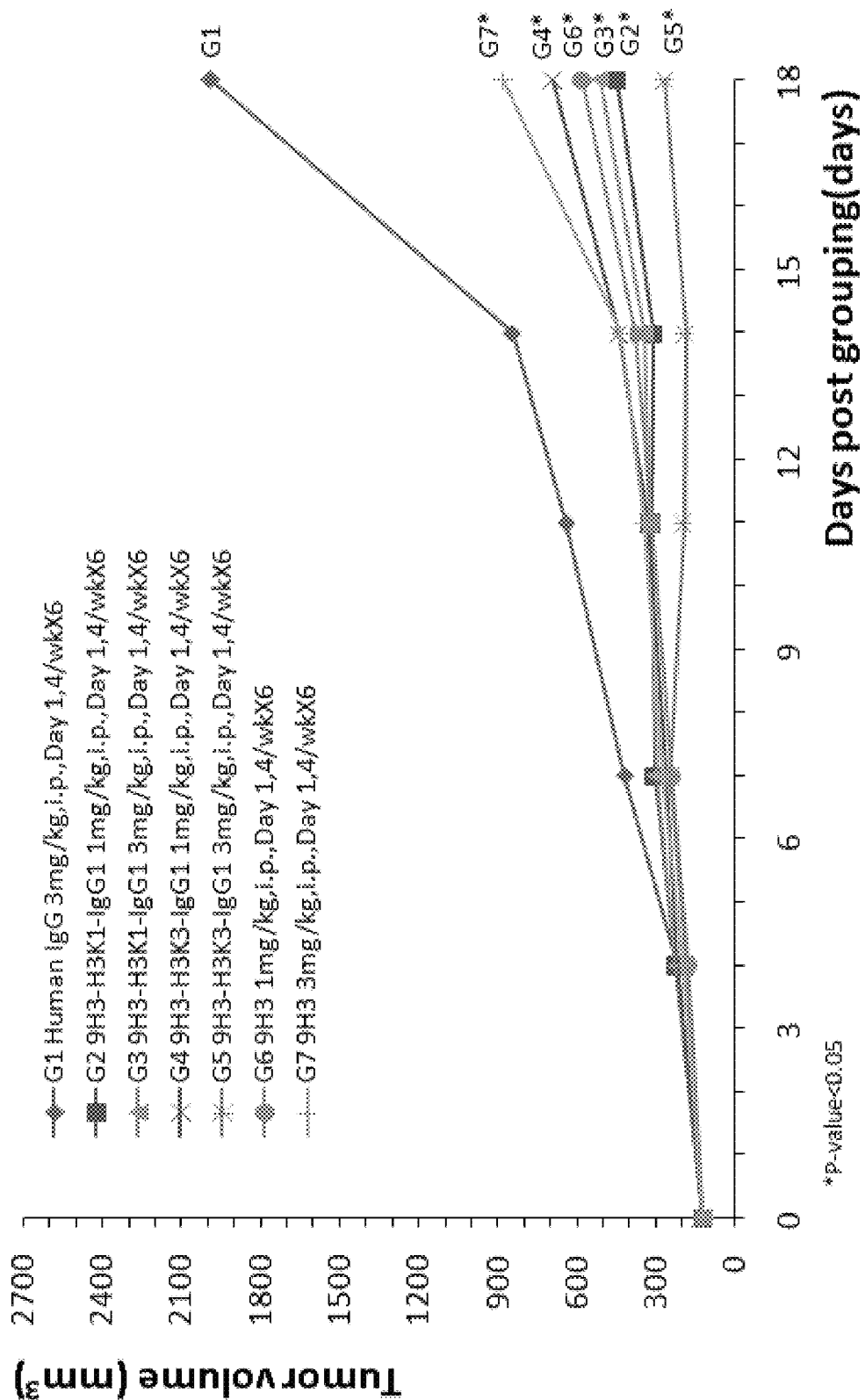
FIG. 15 is a graph showing tumor size over time in OX40 humanized mice (B-hOX40) with MC-38 tumor cells treated with humanized anti-hOX40 antibodies.

The tumor size showed significant difference in groups treated with anti-hOX40 antibodies (FIG. 15).

The TGI % at Day 18 (18 days after grouping) for each treatment group was also calculated as shown in the table below.

TABLE 9

| Group | Antibodies | Average tumor size at Day 18 | TGI % | P value |
|---|---|---|---|---|
| G1 | Human IgG (3 mg/kg) | 1989 | — | — |
| G2 | 9H3-H3K1-IgG1 (1 mg/kg) | 447 | 82.7% | 0.004 |
| G3 | 9H3-H3K1-IgG1 (3 mg/kg) | 514 | 79.0% | 0.005 |
| G4 | 9H3-H3K3-IgG1 (1 mg/kg) | 694 | 69.4% | 0.025 |
| G5 | 9H3-H3K3-IgG1 (3 mg/kg) | 268 | 92.3% | 0.001 |
| G6 | 9H3 (1 mg/kg) | 583 | 75.3% | 0.006 |
| G7 | 9H3 (3 mg/kg) | 880 | 59.4% | 0.042 |

The results above show that all anti-hOX40 antibodies can inhibit tumor growth. Among them, 9H3-H3K3-IgG1 (3 mg/kg) had the highest tumor growth inhibition percentage.

Three mice in G1 group and three mice in G5 group were selected for further evaluation.

Figure 16:
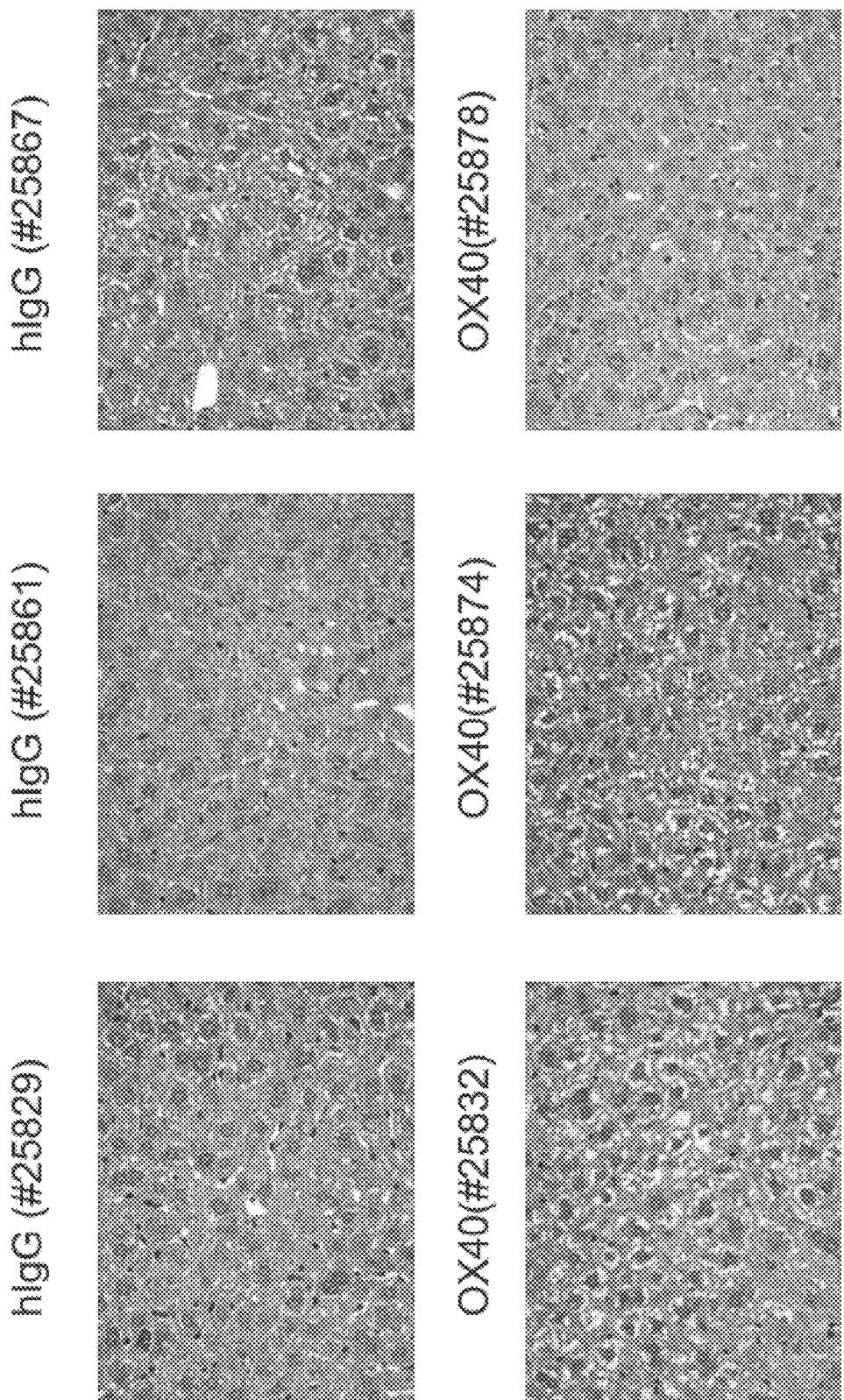
FIG. 16 is a set of liver tissue pathology H&E staining images (400×).

The liver tissues of these mice were examined (FIG. 16). The results were summarized in the tables below. The result shows that compared to the control group, no significant liver damage was observed.

TABLE 10

| Mouse number | Group | Antibody | Dose and administration | Pathological analysis for liver tissue |
|---|---|---|---|---|
| 25829 | G1 | Human IgG | 3 mg/kg, twice a week, 6 injections in total | Liver tissue structure is generally normal with mild hepatocellular edema and mild Kupffer cell hyperplasia. Multiple small focal hepatocyte necrosis sites were observed. |
| 25861 | G1 | Human IgG | 3 mg/kg, twice a week, 6 injections in total | Mild hepatocellular edema. One small focal hepatocyte necrosis site was observed. |
| 25878 | G1 | Human IgG | 3 mg/kg, twice a week, 6 injections in total | Mild to moderate hepatocellular edema. Two small focal hepatocyte necrosis sites were observed. |
| 25832 | G5 | 9H3-H3K3-IgG1 | 3 mg/kg, twice a week, 6 injections in total | Liver tissue structure is generally normal with moderate hepatocellular edema. Some cells had ballooning degeneration. |
| 25867 | G5 | 9H3-H3K3-IgG1 | 3 mg/kg, twice a week, 6 injections in total | Mild hepatocellular edema. |
| 25874 | G5 | 9H3-H3K3-IgG1 | 3 mg/kg, twice a week, 6 injections in total | Mild hepatocellular edema. One small focal hepatocyte necrosis site was observed. |

Figure 17:
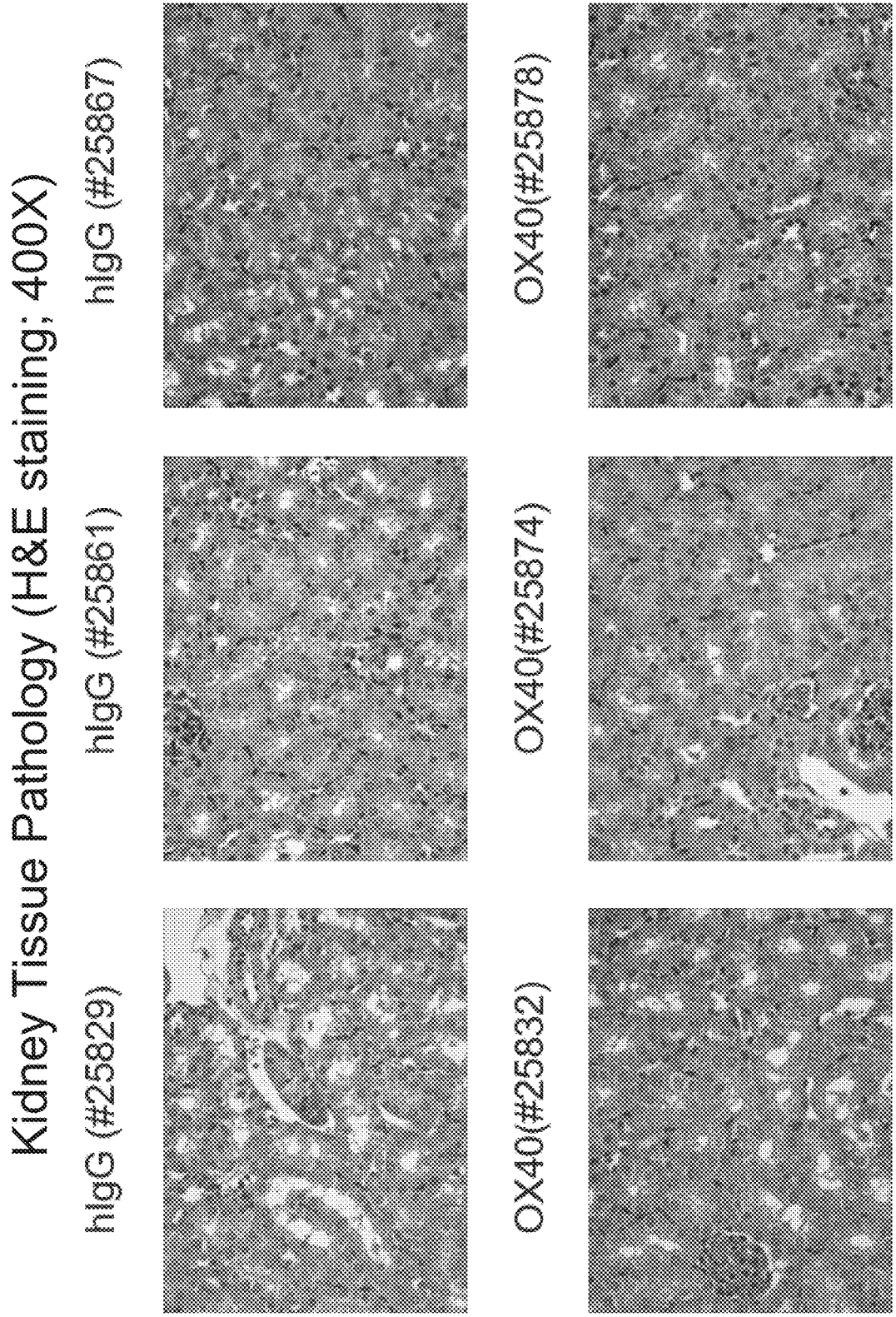
FIG. 17 is a set of kidney tissue pathology H&E staining images (400×).

The kidney of these mice were also examined (FIG. 17). The results were summarized in the tables below. The result shows that compared to the control group, 9H3-H3K3-IgG1 did not cause serious damages in kidneys.

TABLE 11

| Mouse number | Group | Antibody | Dose and administration | Pathological analysis for kidneys |
|---|---|---|---|---|
| 25829 | G1 | Human IgG | 3 mg/kg, twice a week, 6 injections in total | The structure of the kidneys is generally normal, with moderate edema at proximal tubule. |
| 25861 | G1 | Human IgG | 3 mg/kg, twice a week, 6 injections in total | The structure of the kidneys is generally normal, with moderate edema at proximal tubule. |
| 25878 | G1 | Human IgG | 3 mg/kg, twice a week, 6 injections in total | The structure of the kidneys is generally normal, with moderate edema at proximal tubule. |
| 25832 | G5 | 9H3-H3K3-IgG1 | 3 mg/kg, twice a week, 6 injections in total | The structure of the kidneys is generally normal, with moderate edema at proximal tubule. |
| 25867 | G5 | 9H3-H3K3-IgG1 | 3 mg/kg, twice a week, 6 injections in total | The structure of the kidneys is generally normal, with moderate edema at proximal tubule. |
| 25874 | G5 | 9H3-H3K3-IgG1 | 3 mg/kg, twice a week, 6 injections in total | The structure of the kidneys is generally normal, with moderate edema at proximal tubule. |

Figure 18:
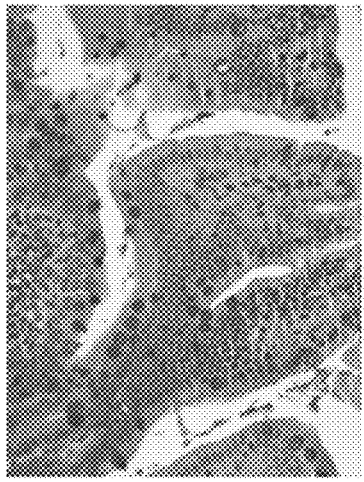
FIG. 18 is a set of intestine tissue pathology H&E staining images (400×).
Figure 18:
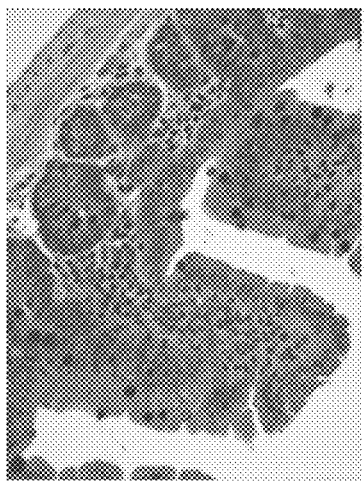
Figure 18:
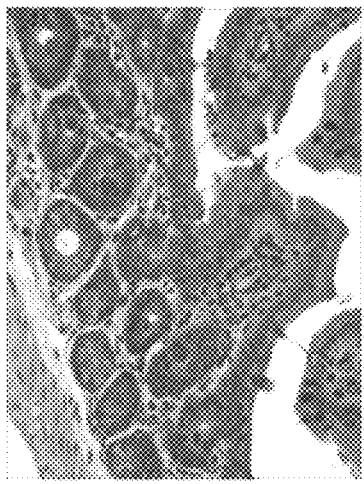
Figure 18:
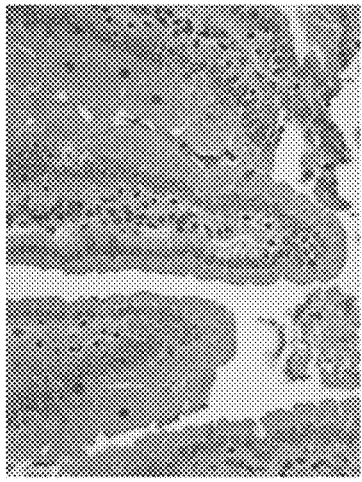
Figure 18:
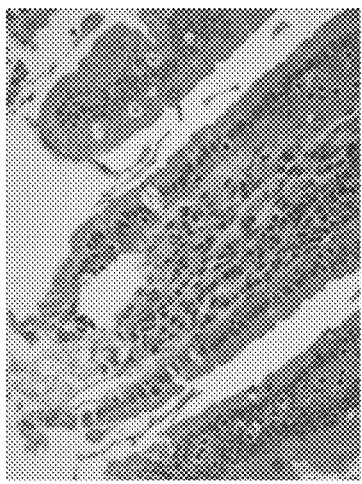
Figure 18:
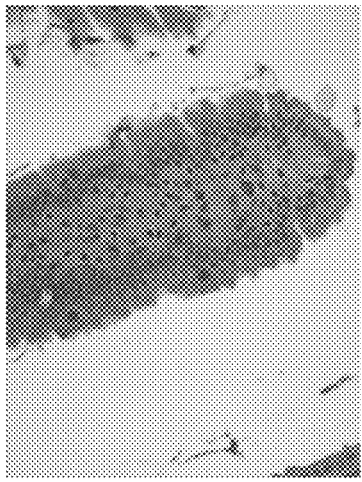

The intestines of these mice were also examined (FIG. 18). The results were summarized in the tables below. The result shows that compared to the control group, 9H3-H3K3-IgG1 does not cause serious damages in intestines.

TABLE 12

| Mouse number | Group | Antibody | Dose and administration | Pathological analysis for intestines |
|---|---|---|---|---|
| 25829 | G1 | Human IgG | 3 mg/kg, twice a week, 6 injections in total | Intestinal mucosal tissue with mild chronic inflammation. |
| 25861 | G1 | Human IgG | 3 mg/kg, twice a week, 6 injections in total | Intestinal mucosal tissue with mild chronic inflammation. |
| 25867 | G1 | Human IgG | 3 mg/kg, twice a week, 6 injections in total | Intestinal mucosal tissue with mild chronic inflammation. |
| 25832 | G5 | 9H3-H3K3-IgG1 | 3 mg/kg, twice a week, 6 injections in total | No obvious pathological changes were found. |
| 25874 | G5 | 9H3-H3K3-IgG1 | 3 mg/kg, twice a week, 6 injections in total | Intestinal mucosal tissue with mild chronic inflammation. |
| 25878 | G5 | 9H3-H3K3-IgG1 | 3 mg/kg, twice a week, 6 injections in total | Intestinal mucosal tissue with mild chronic inflammation. |

Overall, the result suggests that 9H3-H3K3-IgG1 has no serious side effects in humanized mice.

Example 10. Combination Therapy with Keytruda® (Pembrolizumab)

To evaluate the efficacy of combination therapy, anti-hOX40 antibodies were administered to mice with some other therapeutic agents.

In Vivo Results for 9H3 and Keytruda® for MC-38 Cancer Tumor Cells in Humanized Mice MC-38 cancer tumor cells were injected subcutaneously in B-hOX40 humanized mice. When the tumors in the mice reached a volume of 150±50 mm$^3$, the mice were randomly placed into different groups based on the volume of the tumor (6 mice in each group). The mice were then injected with (G1) PS (control), (G2) Keytruda® (0.3 mg/kg) (Merck), (G3) 9H3 (3 mg/kg), and (G4) Keytruda® (0.3 mg/kg) and 9H3 (3 mg/kg) by intraperitoneal injection. The antibody was given on the first day and the fourth day of each week for 3 weeks (6 injections in total).

Figure 19:
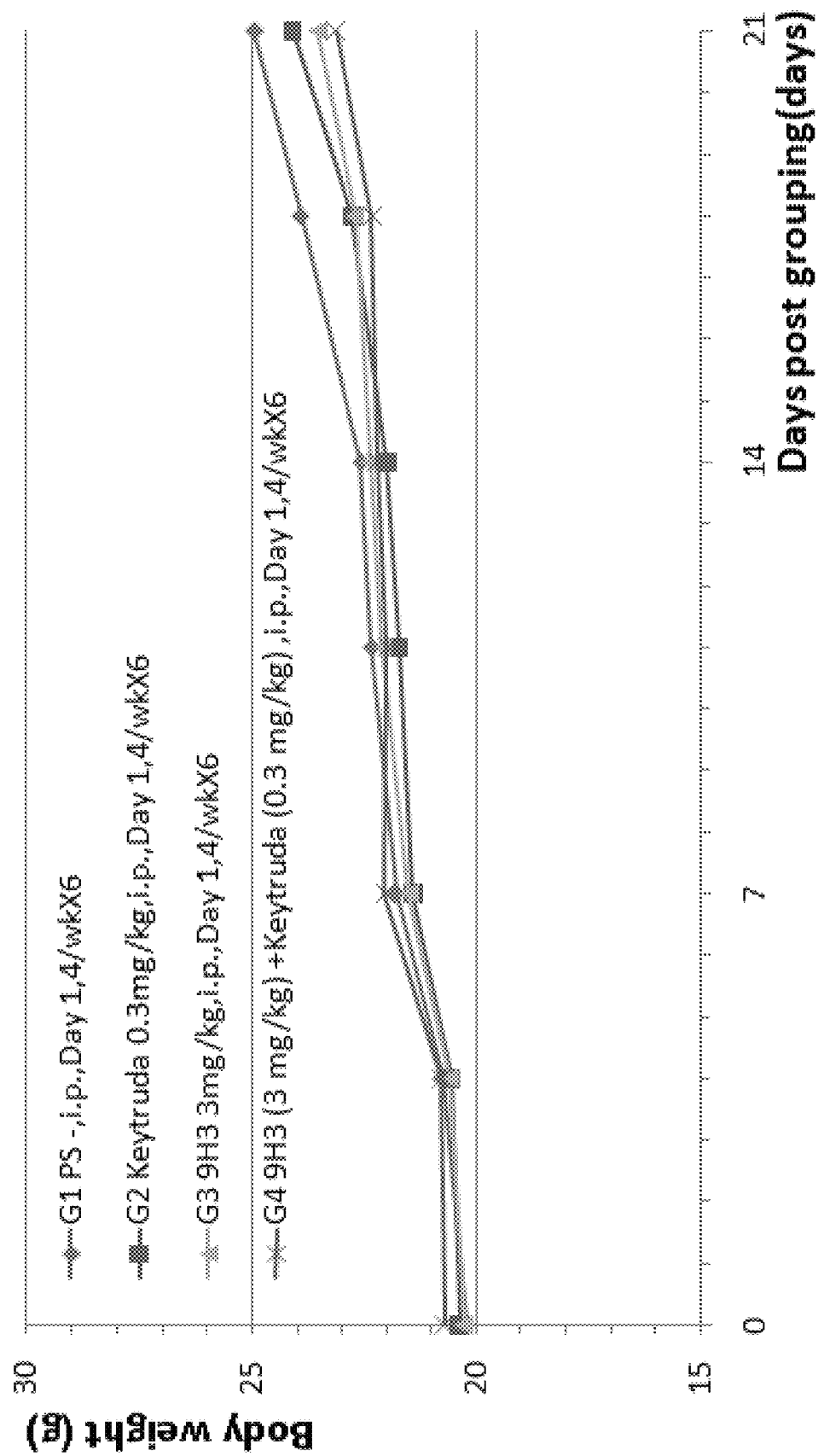
FIG. 19 is a graph showing body weight over time of OX40 humanized mice (B-hOX40) with MC-38 tumor cells treated with 9H3 and Keytruda®.
Figure 20:
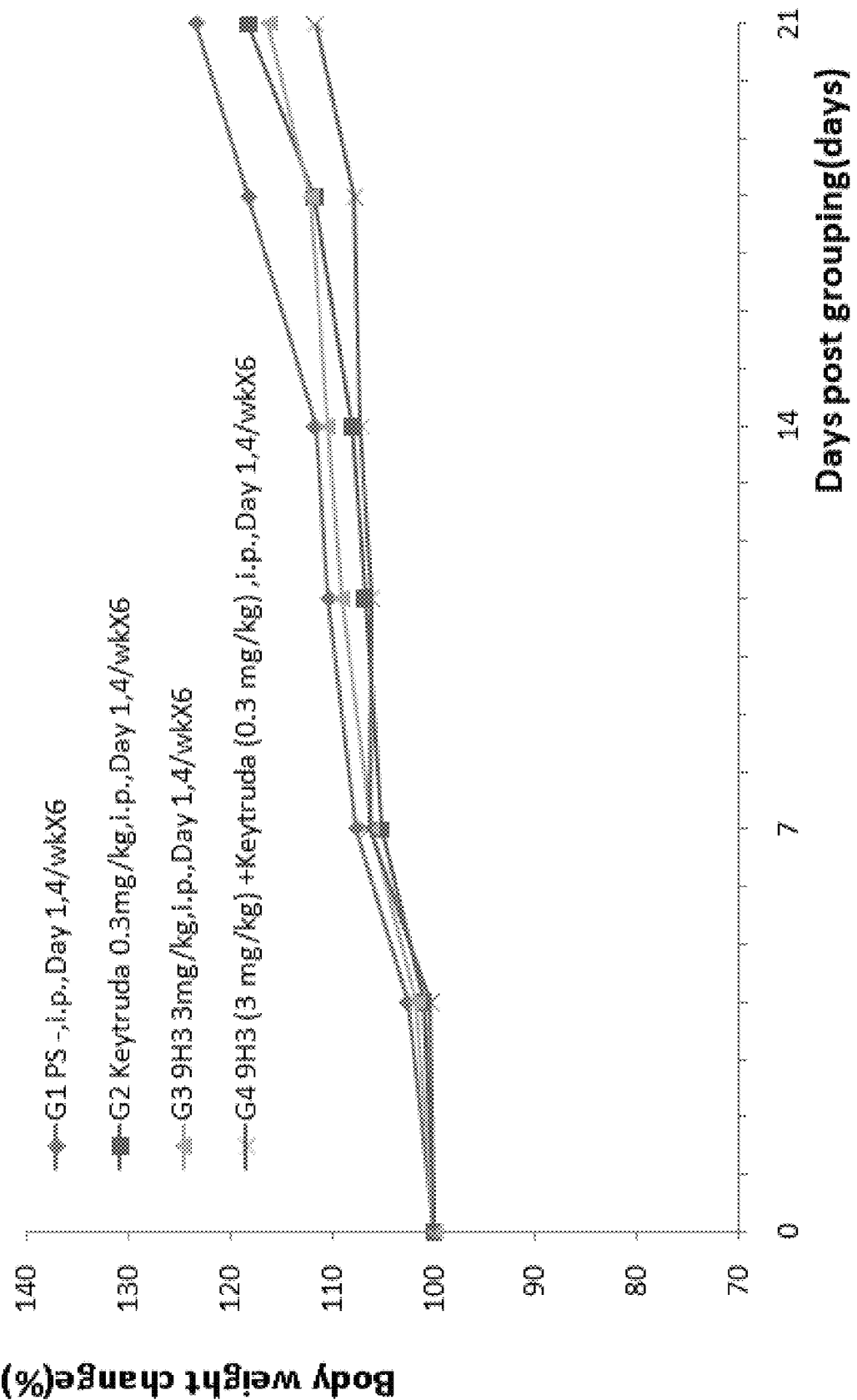
FIG. 20 is a graph showing percentage change of body weight over time of OX40 humanized mice (B-hOX40) with MC-38 tumor cells treated with 9H3 and Keytruda®.

The weight of the mice was monitored during the entire treatment period. The weight of mice in different groups all increased (FIG. 19, and FIG. 20). No significant difference in weight was observed between the control group and the anti-hOX40 treatment groups. The results showed that these antibodies were well tolerated and not toxic to the mice.

Figure 21:
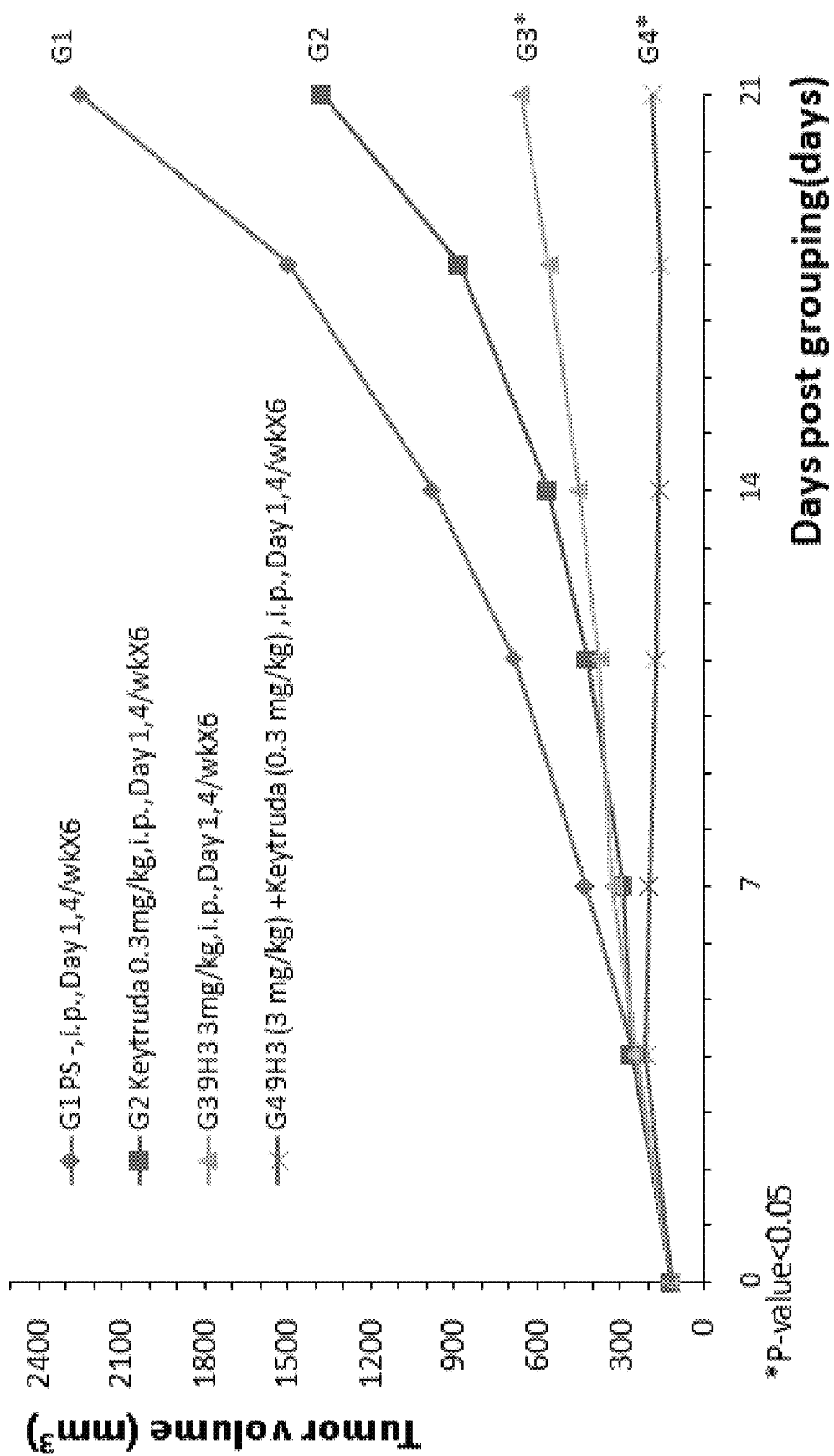
FIG. 21 is a graph showing tumor size over time in OX40 humanized mice (B-hOX40) with MC-38 tumor cells treated with 9H3 and Keytruda®.

The tumor size showed significant difference in groups treated with anti-hOX40 antibodies (FIG. 21). The TGI % at Day 21 (21 days after grouping) for each treatment group was also calculated and is shown in the table below.

TABLE 13

| Group | Antibodies | Average tumor size at Day 21 | TGI % | P value |
|---|---|---|---|---|
| G1 | PS | 2256 | — | — |
| G2 | Keytruda ® (Pembrolizumab) (0.3 mg/kg) | 1380 | 41.0% | 0.127 |
| G3 | 9H3 (3 mg/kg) | 662 | 74.6% | 0.003 |
| G4 | 9H3 (3 mg/kg) + Keytruda ® (0.3 mg/kg) | 187 | 96.8% | 0.0003 |

The result shows that 9H3 in combination with Keytruda® can improve tumor growth inhibition effects.

In Vivo Results for 9H3 and Keytruda® for EL4 Cancer Tumor Cells in Humanized Mice EL4 cancer tumor cells (murine tumor cell line derived from a chemically induced lymphoma) were injected subcutaneously in B-hOX40 humanized mice. When the tumors in the mice reached a volume of 150±50 mm$^3$, the mice were randomly placed into different groups based on the volume of the tumor (5 mice in each group). The mice were then injected with (G1) PS (control), (G2) 9H3 (3 mg/kg), (G3) Keytruda® (3 mg/kg), and (G4) Keytruda® (3 mg/kg) and 9H3 (3 mg/kg) by intraperitoneal injection. The antibody was given on the first day and the fourth day of each week for 3 weeks (6 injections in total).

Figure 22:
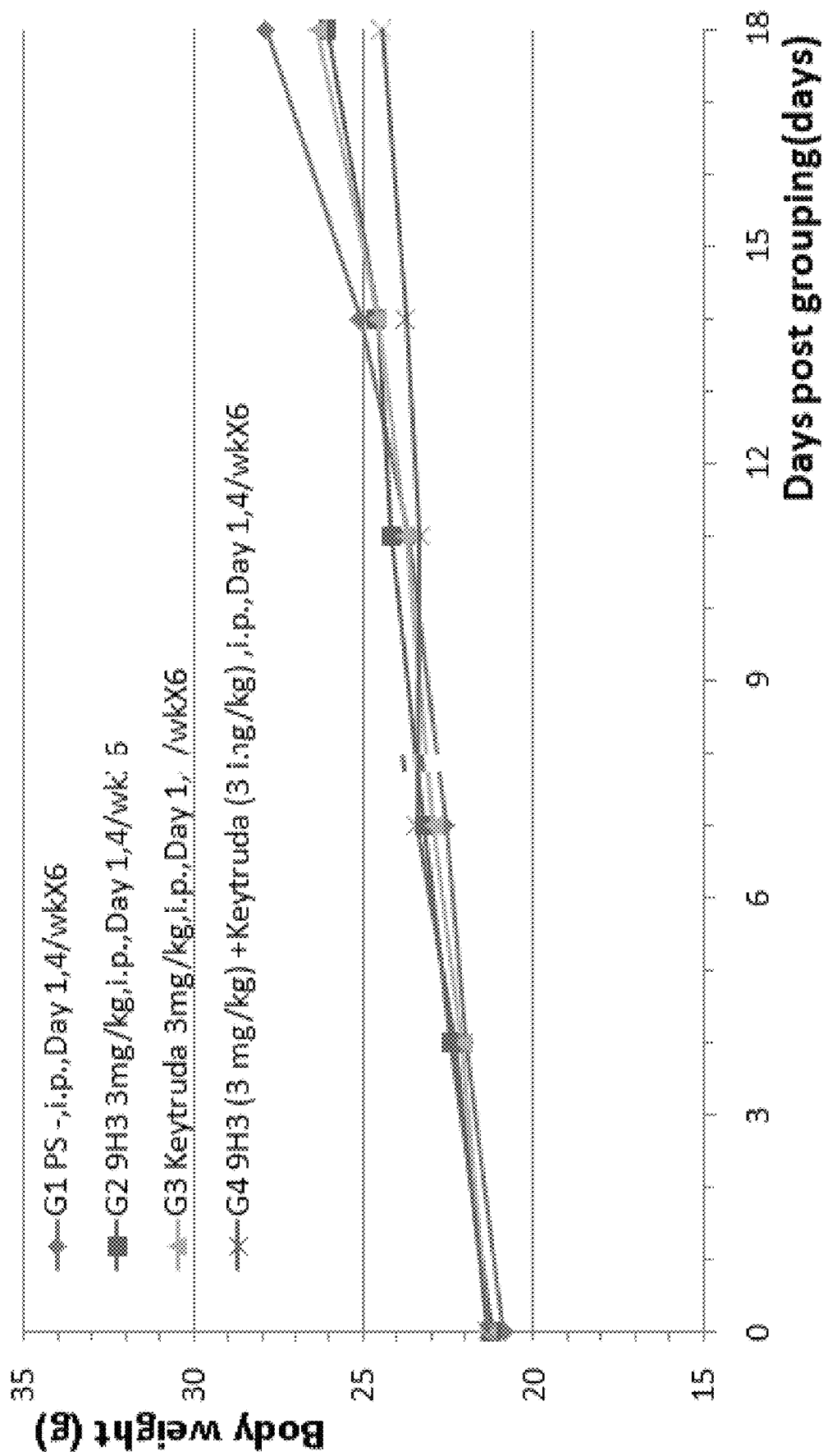
FIG. 22 is a graph showing body weight over time of OX40 humanized mice (B-hOX40) with EL4 cancer cells treated with 9H3 and Keytruda®.
Figure 23:
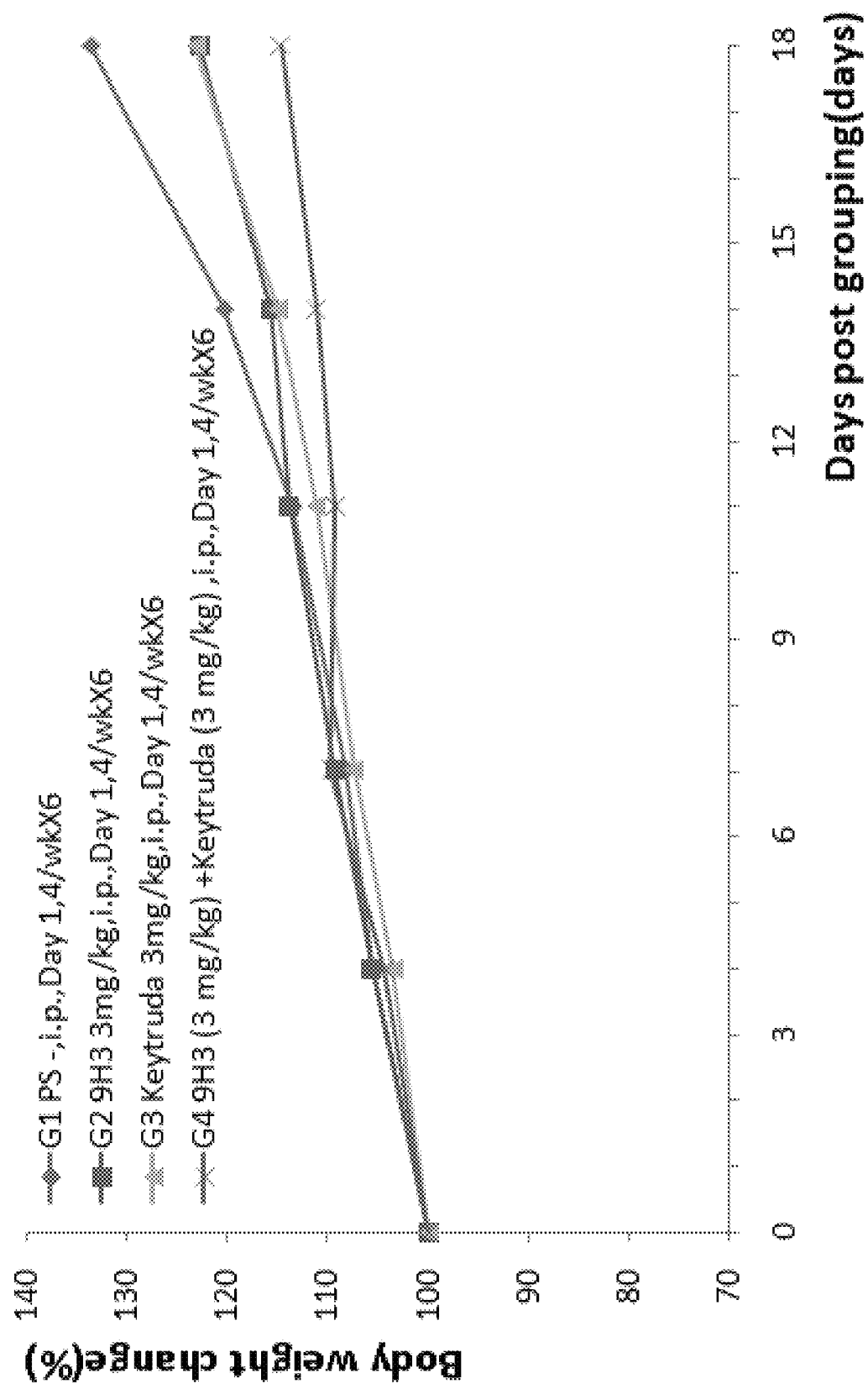
FIG. 23 is a graph showing percentage change of body weight over time of OX40 humanized mice (B-hOX40) with EL4 cancer cells treated with 9H3 and Keytruda®.

The weight of the mice was monitored during the entire treatment period. The weight of mice in different groups all increased (FIG. 22, and FIG. 23). The results showed that these antibodies were well tolerated and not toxic to the mice.

Figure 24:
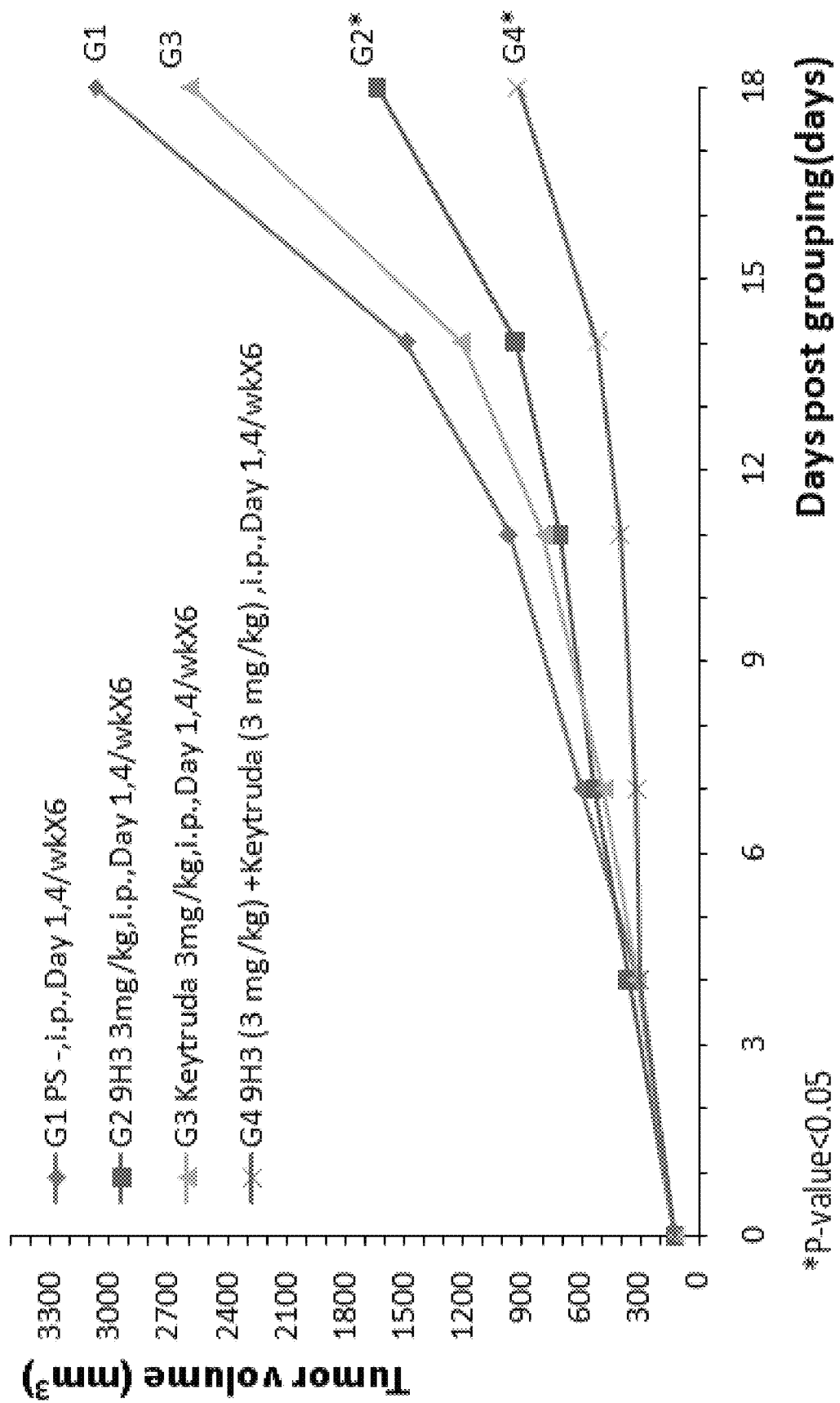
FIG. 24 is a graph showing tumor size over time in OX40 humanized mice (B-hOX40) with EL4 cancer cells treated with 9H3 and Keytruda®.

The tumor size showed significant difference in groups treated with 9H3 and the combination of 9H3 and Keytruda® (FIG. 24). The TGI % at Day 18 (18 days after grouping) for each treatment group was shown in the table below.

TABLE 14

| Group | Antibodies | Average tumor size at Day 18 | TGI % | P value |
|---|---|---|---|---|
| G1 | PS | 3075 | — | — |
| G2 | 9H3 (3 mg/kg) | 1637 | 48.7% | 0.048 |
| G3 | Keytruda ® (Pembrolizumab) (3 mg/kg) | 2592 | 16.3% | 0.545 |
| G4 | 9H3 (3 mg/kg) + Keytruda ® (3 mg/kg) | 920 | 73.0% | 0.018 |

The result shows that Keytruda® by itself cannot inhibit tumor growth. However, the combination of Keytruda® and 9H3 had better TGI % than using 9H3 alone.

Example 11. Combination Therapy with Anti-PD1 or Anti-PDL1 Antibodies

To evaluate the efficacy of combination therapy, anti-hOX40 antibodies were administered to mice with anti-PD1 or anti-PDL1 antibodies.

MC-38 cancer tumor cells were injected subcutaneously in B-hOX40 humanized mice. When the tumors in the mice reached a volume of 150±50 mm$^3$, the mice were randomly placed into different groups based on the volume of the tumor (5 mice in each group). The mice were then injected with (G1) PS (control); (G2) 9H3 (1 mg/kg); (G3) mPD-1 (RMP1-14) (mouse anti-mPD1 antibody; BioXcell, catalog number BE0146) (1 mg/kg); (G4) 9H3 (1 mg/kg) and mPD-1(RMP1-14) (1 mg/kg); (G5) mPD-L1(10F.9G2) (mouse anti-mPDL1 antibody; BioXcell, catalog number BE0101) (1 mg/kg); or (G6) 9H3 (1 mg/kg) and mPD-L1 (10F.9G2) (1 mg/kg) by intraperitoneal administration. The antibody was administered twice a week for 3 weeks (6 injections in total).

Figure 25:
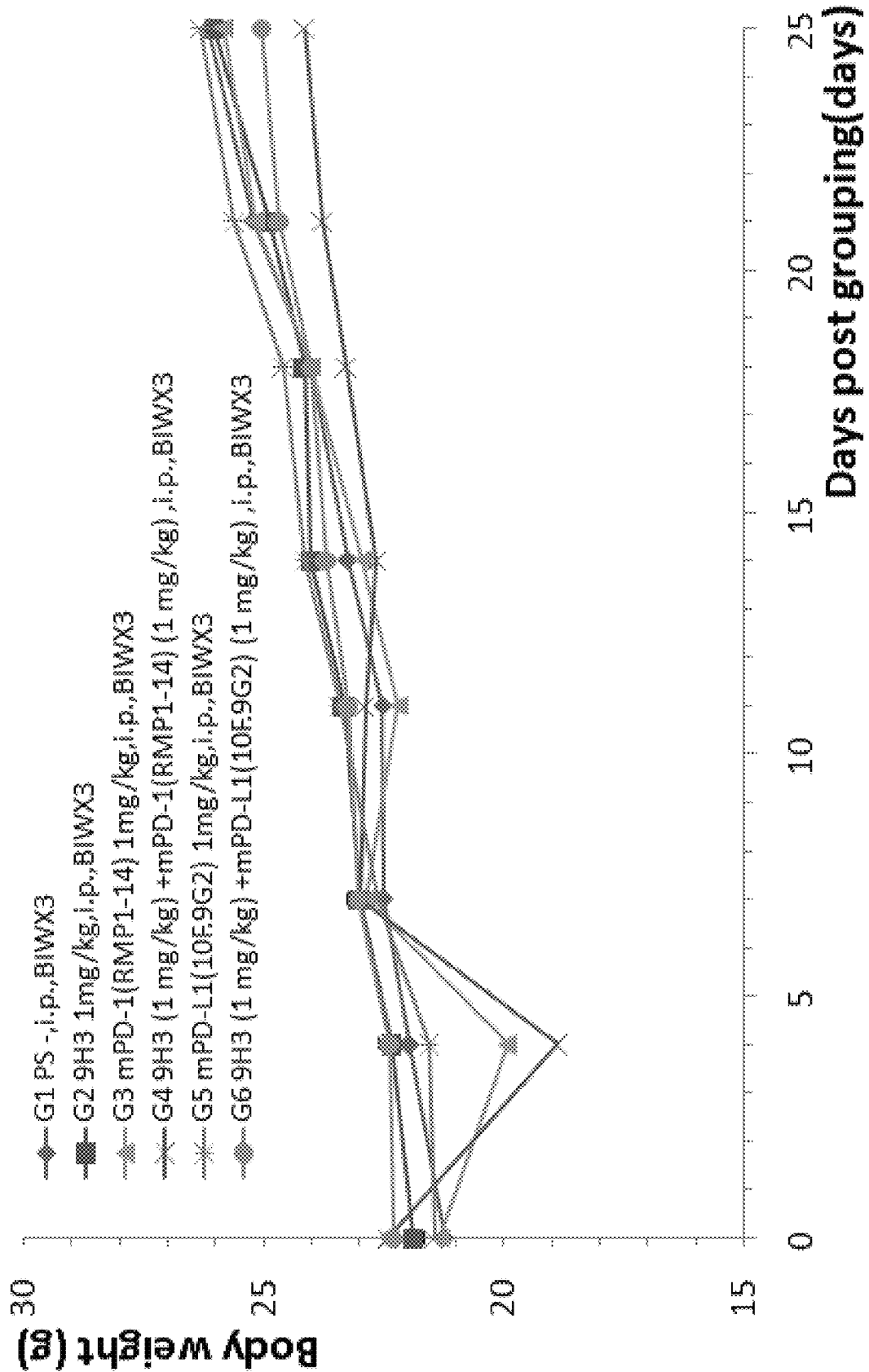
FIG. 25 is a graph showing body weight over time of OX40 humanized mice (B-hOX40) with MC-38 tumor cells treated with 9H3, an anti-PD1 antibody, and/or an anti-PD-L1 antibody.
Figure 26:
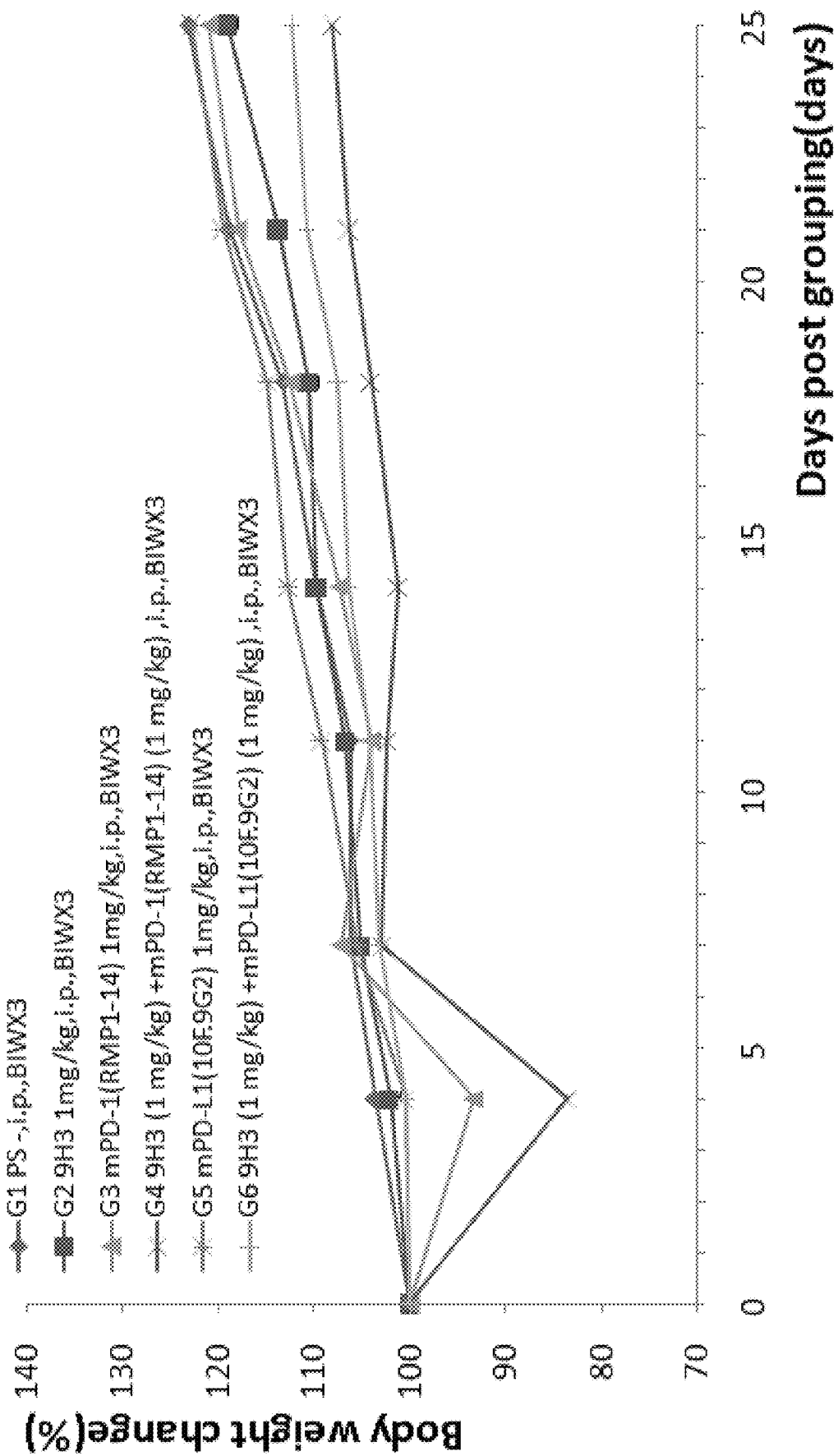
FIG. 26 is a graph showing percentage change of body weight over time of OX40 humanized mice (B-hOX40) with MC-38 tumor cells treated with 9H3, an anti-PD1 antibody, and/or an anti-PD-L1 antibody.

The weight of the mice was monitored during the entire treatment period (FIG. 25, and FIG. 26). The results showed that these antibodies were not toxic to the mice.

Figure 27:
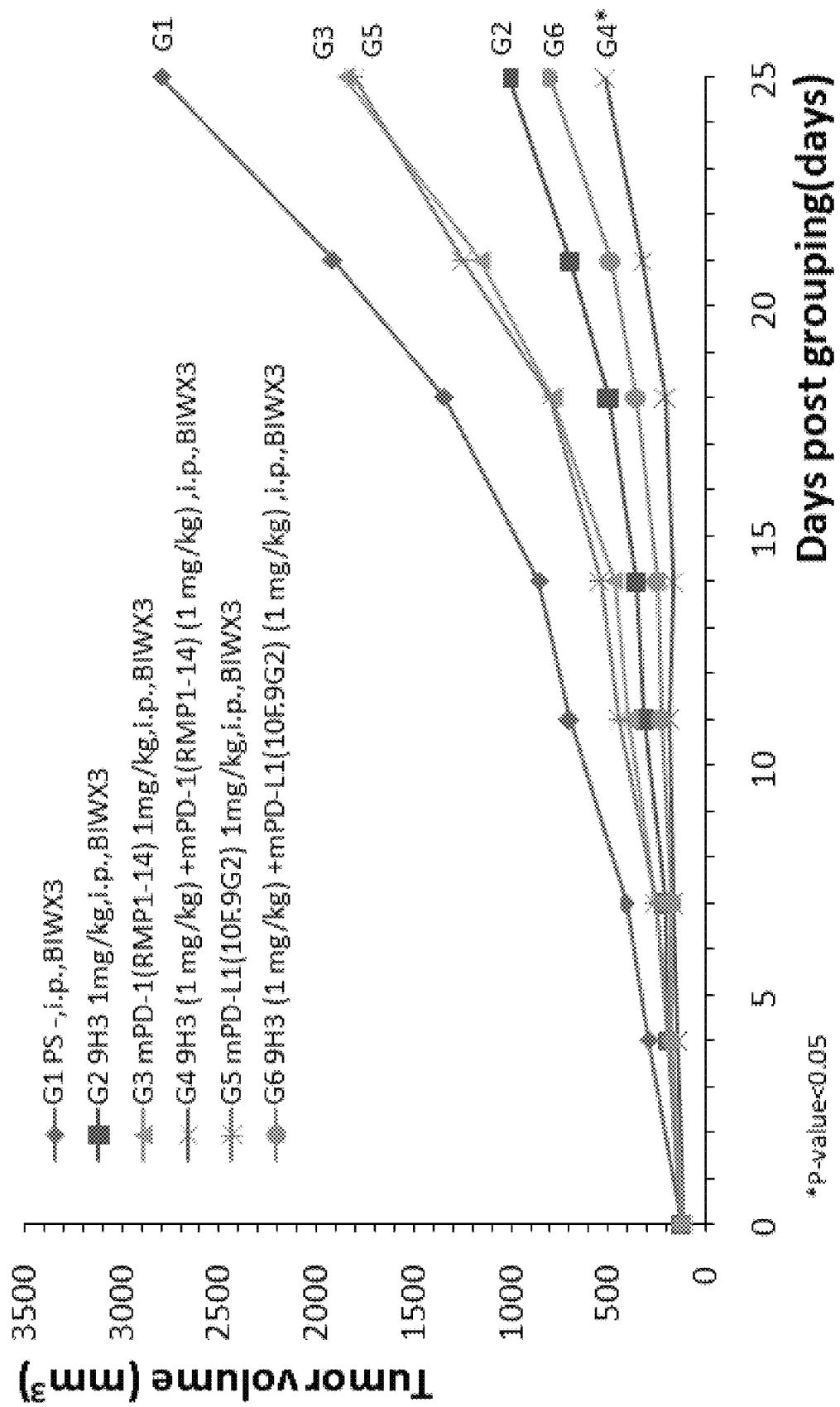
FIG. 27 is a graph showing tumor size over time in OX40 humanized mice (B-hOX40) with MC-38 tumor cells treated with 9H3, an anti-PD1 antibody, and an anti-PD-L1 antibody.

The tumor size decreased in groups treated with the antibodies (FIG. 27). The TGI % at Day 25 (25 days after grouping) for each treatment group was shown in the table below.

TABLE 15

| Group | Antibodies | Average tumor size at Day 25 | TGI % | P value |
|---|---|---|---|---|
| G1 | PS | 2796 | — | — |
| G2 | 9H3 (1 mg/kg) | 1013 | 66.7% | 0.080 |
| G3 | mPD-1(RMP1-14) (1 mg/kg) | 1851 | 35.4% | 0.329 |
| G4 | 9H3 (1 mg/kg) + mPD-1(RMP1-14) (1 mg/kg) | 516 | 85.2% | 0.032 |
| G5 | mPD-L1(10F.9G2) (1 mg/kg) | 1801 | 37.2% | 0.296 |
| G6 | 9H3 (1 mg/kg) + mPD-L1(10F.9G2) (1 mg/kg) | 804 | 74.5% | 0.056 |

The result shows that 9H3 in combination with mPD-1 (RMP1-14) (an anti-PD-1 antibody) had the best tumor growth inhibition rate.

Example 12. Combination Therapy with Anti-LAG-3, Anti-TIGIT, Anti-BTLA, Anti-CTLA-4 or Anti-GITR Antibodies To evaluate the efficacy of combination therapy, anti-hOX40 antibodies were administered to mice with anti-LAG-3, anti-TIGIT, anti-BTLA, anti-CTLA-4 or anti-GITR antibodies.

MC-38 cancer tumor cells were injected subcutaneously in B-hOX40 humanized mice. When the tumors in the mice reached a volume of 150±50 mm$^3$, the mice were randomly placed into different groups based on the volume of the tumor (5 mice in each group). The mice were then injected with the following by intraperitoneal administration:
(G1) PS (control);
(G2) 9H3 (1 mg/kg);
(G3) mLAG-3(C9B7W) (mouse anti-LAG-3 antibody; BioXcell, Catalog #: BE0174) (3 mg/kg);
(G4) 9H3 (1 mg/kg) and mLAG-3(C9B7W) (3 mg/kg);
(G5) mTIGIT(1G9) (mouse anti-mTIGIT antibody; BioXcell, Catalog #: BE0274) (3 mg/kg);
(G6) 9H3 (1 mg/kg) and mTIGIT(1G9) (3 mg/kg);
(G7) mBTLA(PJ196) (mouse anti-mBTLA antibody; BioXcell, Catalog #: BE0196) (10 mg/kg);
(G8) 9H3 (1 mg/kg) and mBTLA(PJ196) (10 mg/kg);
(G9) mCTLA-4(9D9) (mouse anti-mCTLA-4 antibody; BioXcell, Catalog #: BE0164) (1 mg/kg);
(G10) 9H3 (1 mg/kg) and mCTLA-4(9D9) (1 mg/kg);
(G11) mGITR(DTA-1) (mouse anti-mGITR antibody; BioXcell, Catalog #: BE0063) (0.3 mg/kg);
(G12) 9H3 (1 mg/kg) and mGITR(DTA-1) (0.3 mg/kg).

The antibody was administered twice a week (3 injections in total).

Figure 28:
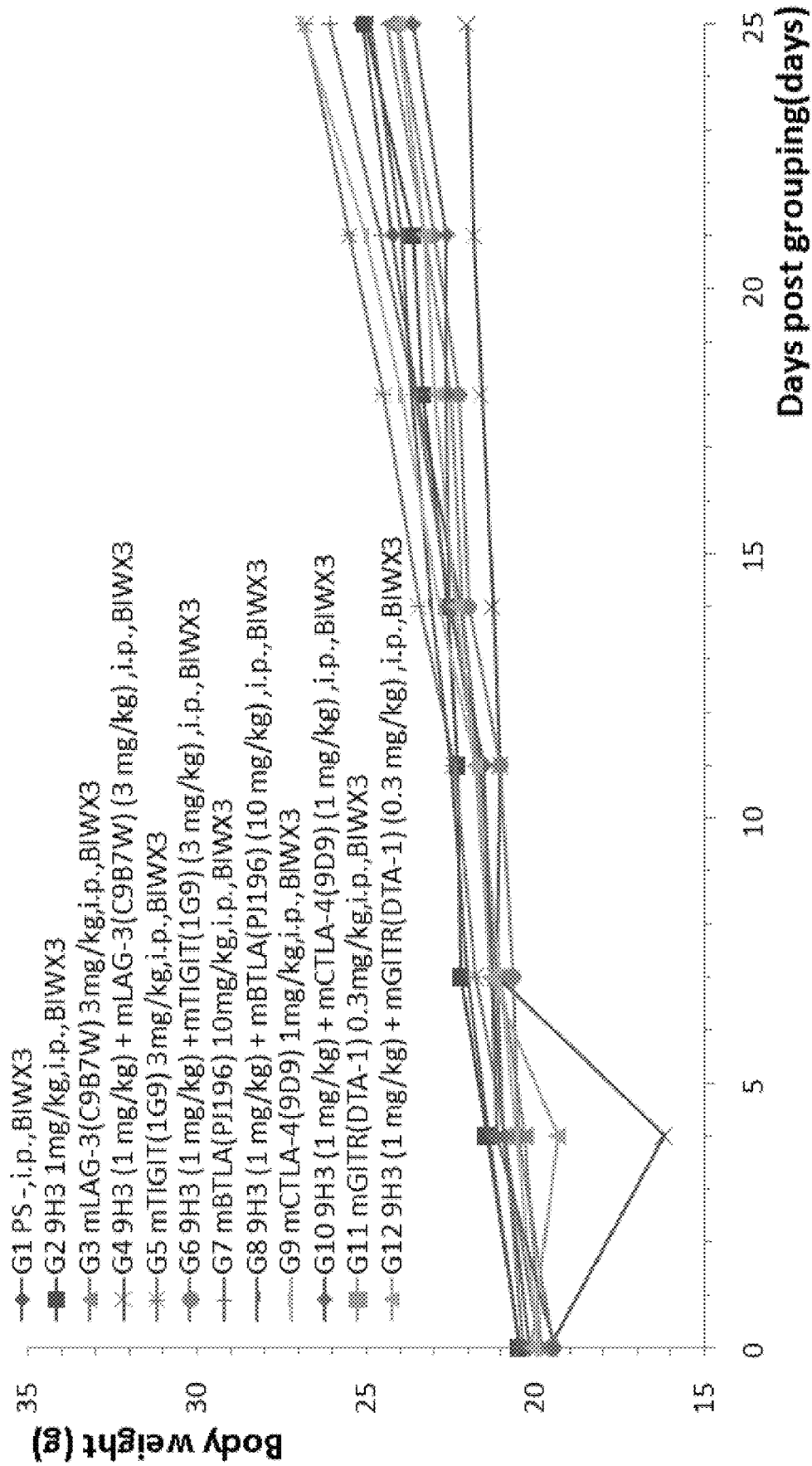
FIG. 28 is a graph showing body weight over time of OX40 humanized mice (B-hOX40) with MC-38 tumor cells treated with 9H3, anti-LAG-3, anti-TIGIT, anti-BTLA, anti-CTLA-4 and/or anti-GITR antibodies
Figure 29:
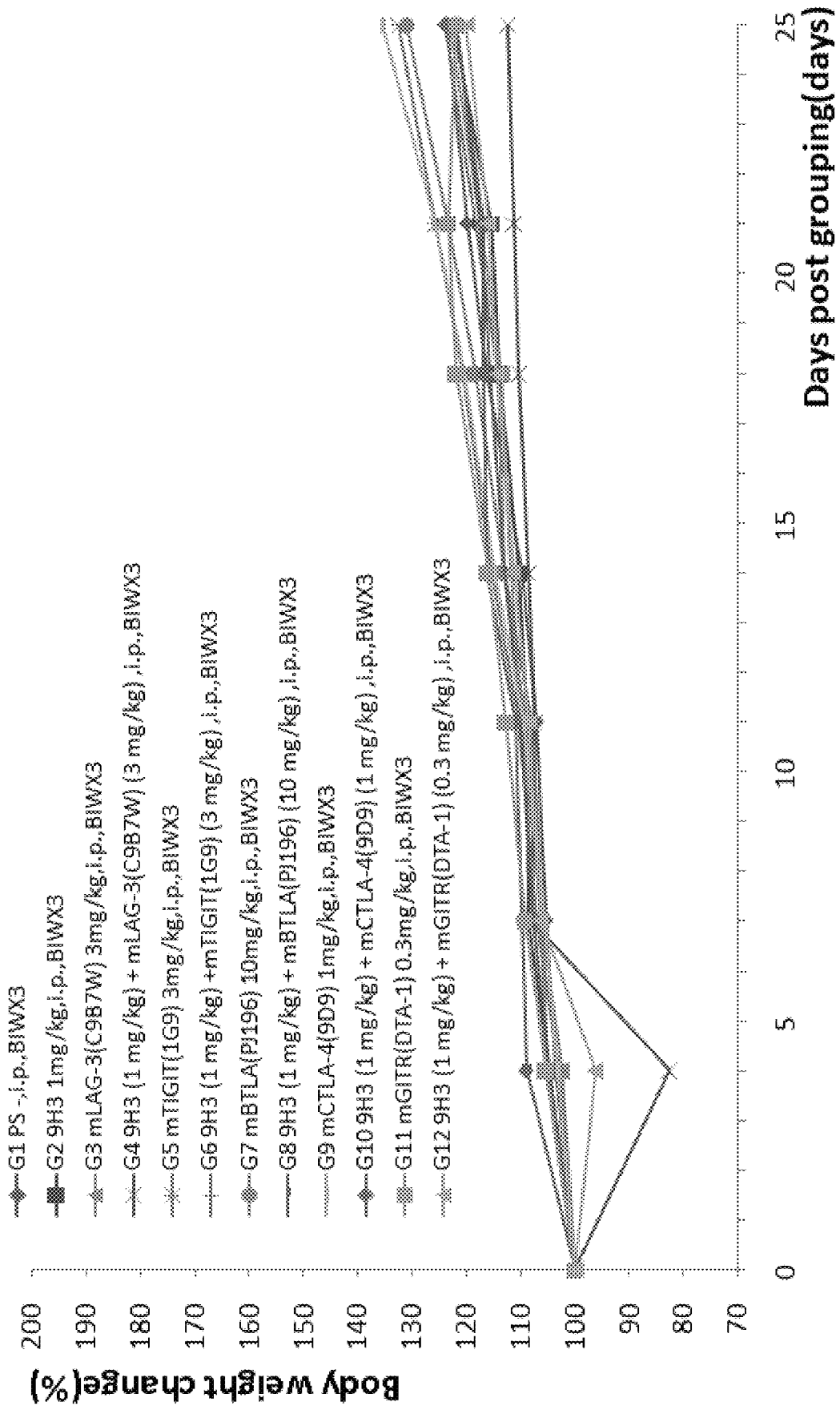
FIG. 29 is a graph showing percentage change of body weight over time of OX40 humanized mice (B-hOX40) with MC-38 tumor cells treated with 9H3, anti-LAG-3, anti-TIGIT, anti-BTLA, anti-CTLA-4 and/or anti-GITR antibodies.

The weight of the mice was monitored during the entire treatment period (FIG. 28, and FIG. 29). The results showed that these antibodies were not clearly toxic to the mice.

Figure 30:
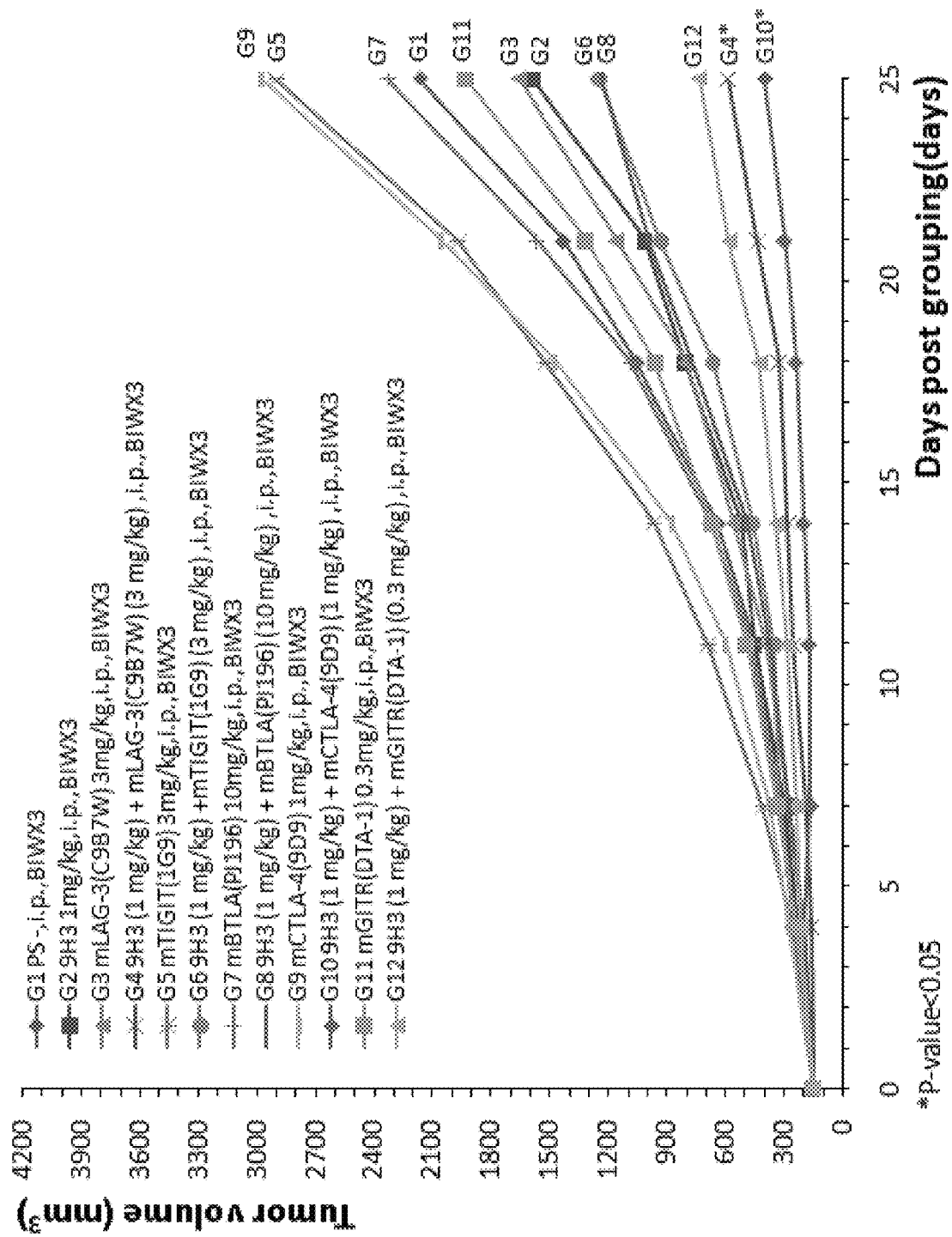
FIG. 30 is a graph showing tumor size over time in OX40 humanized mice (B-hOX40) with MC-38 tumor cells treated with 9H3, anti-LAG-3, anti-TIGIT, anti-BTLA, anti-CTLA-4 and/or anti-GITR antibodies.

In G2, G3, G4, G6, G8, G10, G11, and G12 treatment groups, the tumor size decreased (FIG. 30). The TGI % at Day 25 (25 days after grouping) for each treatment group was shown in the table below.

TABLE 16

| Group | Antibodies | Average tumor size at Day 25 | TGI % | P value |
|---|---|---|---|---|
| G1 | PS | 2166 | — | — |
| G2 | 9H3 (1 mg/kg) | 1586 | 28.8% | 0.393 |
| G3 | mLAG-3(C9B7W) (3 mg/kg) | 1654 | 25.4% | 0.436 |
| G4 | 9H3 (1 mg/kg) + mLAG-3(C9B7W) (3 mg/kg) | 587 | 78.4% | 0.017 |
| G5 | mTIGIT(1G9) (3 mg/kg) | 2901 | −36.5% | 0.336 |
| G6 | 9H3 (1 mg/kg) + mTIGIT(1G9) (3 mg/kg) | 1244 | 45.7% | 0.142 |
| G7 | mBTLA(PJ196) (10 mg/kg) | 2328 | −8.0% | 0.825 |
| G8 | 9H3 (1 mg/kg) + mBTLA(PJ196) (10 mg/kg) | 1232 | 46.3% | 0.149 |
| G9 | mCTLA-4(9D9) (1 mg/kg) | 2977 | −40.2% | 0.267 |

TABLE 16-continued

| Group | Antibodies | Average tumor size at Day 25 | TGI % | P value |
|---|---|---|---|---|
| G10 | 9H3 (1 mg/kg) + mCTLA-4(9D9) (1 mg/kg) | 397 | 87.8% | 0.026 |
| G11 | mGITR(DTA-1) (0.3 mg/kg) | 1924 | 12.0% | 0.665 |
| G12 | 9H3 (1 mg/kg) + mGITR(DTA-1) (0.3 mg/kg) | 735 | 71.0% | 0.283 |

The result shows that 9H3 in combination with anti-LAG-3, anti-TIGIT, anti-BTLA, anti-CTLA-4 or anti-GITR antibodies had better tumor growth inhibition effects than using 9H3 alone.

Example 13. In Vivo Testing of Humanized 9A4, 5C1, and 5D10 Antibodies

The humanized 9A4, 5C1, and 5D10 antibodies are also tested in OX40 humanized mice to demonstrate their effect on tumor growth in vivo.

MC-38 cancer tumor cells (colon adenocarcinoma cell) are injected subcutaneously in B-hOX40 humanized mice. When the tumors in the mice reach a volume of 150±50 mm$^3$, the mice are randomly placed into different groups based on the volume of the tumor. The mice are then injected with human IgG (control) and humanized 9A4, 5C1, and 5D10 antibodies by intraperitoneal injection at either 3 mg/kg or 1 mg/kg. The antibody is given on the first day and the fourth day of each week for 3 weeks (6 injections in total).

The weight of the mice is monitored during the entire treatment period. It is expected that no significant difference in weight can be observed between the control group and the anti-hOX40 antibody treatment groups, and the humanized 9A4, 5C1, and 5D10 antibodies can inhibit tumor growth in mice.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An antibody or antigen-binding fragment thereof that binds to human OX40 (TNF Receptor Superfamily Member 4) comprising:
    a heavy chain variable region (VH) comprising complementarity determining regions (CDRs) 1, 2, and 3, wherein the VH CDR1 region comprises an amino acid sequence that is identical to a selected VH CDR1 amino acid sequence, the VH CDR2 region comprises an amino acid sequence that is identical to a selected VH CDR2 amino acid sequence, and the VH CDR3 region comprises an amino acid sequence that is identical to a selected VH CDR3 amino acid sequence; and
    a light chain variable region (VL) comprising CDRs 1, 2, and 3, wherein the VL CDR1 region comprises an amino acid sequence that is identical to a selected VL CDR1 amino acid sequence, the VL CDR2 region comprises an amino acid sequence that is identical to a selected VL CDR2 amino acid sequence, and the VL CDR3 region comprises an amino acid sequence that is identical to a selected VL CDR3 amino acid sequence,
    wherein the selected VH CDRs 1, 2, and 3 amino acid sequences and the selected VL CDRs, 1, 2, and 3 amino acid sequences are one of the following:
(1) the selected VH CDRs 1, 2, 3 amino acid sequences are set forth in SEQ ID NOs: 1, 2, 3, respectively, and the selected VL CDRs 1, 2, 3 amino acid sequences are set forth in SEQ ID NOs: 4, 5, 6, respectively;
(2) the selected VH CDRs 1, 2, 3 amino acid sequences are set forth in SEQ ID NOs: 25, 26, 27, respectively, and the selected VL CDRs 1, 2, 3 amino acid sequences are set forth in SEQ ID NOs: 28, 29, 30, respectively;
(3) the selected VH CDRs 1, 2, 3 amino acid sequences are set forth in SEQ ID NOs: 7, 8, 9, respectively, and the selected VL CDRs 1, 2, 3 amino acid sequences are set forth in SEQ ID NOs: 10, 11, 12, respectively;
(4) the selected VH CDRs 1, 2, 3 amino acid sequences are set forth in SEQ ID NOs: 31, 32, 33, respectively, and the selected VL CDRs 1, 2, 3 amino acid sequences are set forth in SEQ ID NOs: 34, 35, 36, respectively;
(5) the selected VH CDRs 1, 2, 3 amino acid sequences are set forth in SEQ ID NOs: 13, 14, 15, respectively, and the selected VL CDRs 1, 2, 3 amino acid sequences are set forth in SEQ ID NOs: 16, 17, 18, respectively;
(6) the selected VH CDRs 1, 2, 3 amino acid sequences are set forth in SEQ ID NOs: 37, 38, 39, respectively, and the selected VL CDRs 1, 2, 3 amino acid sequences are set forth in SEQ ID NOs: 40, 41, 42, respectively;
(7) the selected VH CDRs 1, 2, 3 amino acid sequences are set forth in SEQ ID NOs: 19, 20, 21, respectively, and the selected VL CDRs 1, 2, 3 amino acid sequences are set forth in SEQ ID NOs: 22, 23, 24, respectively; and
(8) the selected VH CDRs 1, 2, 3 amino acid sequences are set forth in SEQ ID NOs: 43, 44, 45, respectively, and the selected VL CDRs 1, 2, 3 amino acid sequences are set forth in SEQ ID NOs: 46, 47, 48, respectively.

2. The antibody or antigen-binding fragment thereof of claim 1, wherein the VH comprises CDRs 1, 2, 3 with the amino acid sequences set forth in SEQ ID NOs: 1, 2, and 3, respectively, and the VL comprises CDRs 1, 2, 3 with the amino acid sequences set forth in SEQ ID NOs: 4, 5, and 6, respectively, wherein the VH CDRs 1, 2, 3 and VL CDRs 1, 2, 3 are determined according to Kabat definition.

3. The antibody or antigen-binding fragment thereof of claim 1, wherein the VH comprises CDRs 1, 2, 3 with the amino acid sequences set forth in SEQ ID NOs: 25, 26, and 27, respectively, and the VL comprises CDRs 1, 2, 3 with the amino acid sequences set forth in SEQ ID NOs: 28, 29, and 30, respectively, wherein the VH CDRs 1, 2, 3 and VL CDRs 1, 2, 3 are determined according to Chothia definition.

4. The antibody or antigen-binding fragment thereof of claim 1, wherein the antibody or antigen-binding fragment is a humanized antibody or antigen-binding fragment thereof, a single-chain variable fragment (scFV), or a bispecific antibody.

5. An antibody-drug conjugate comprising the antibody or antigen-binding fragment thereof of claim 1 covalently bound to a therapeutic agent.

6. A pharmaceutical composition comprising the antibody or antigen-binding fragment thereof of claim 1, and a pharmaceutically acceptable carrier.

7. The antibody or antigen-binding fragment thereof of claim 1, wherein the VH comprises CDRs 1, 2, 3 with the amino acid sequences set forth in SEQ ID NOs: 7, 8, and 9, respectively, and the VL comprises CDRs 1, 2, 3 with the amino acid sequences set forth in SEQ ID NOs: 10, 11, and 12, respectively, wherein the VH CDRs 1, 2, 3 and VL CDRs 1, 2, 3 are determined according to Kabat definition.

8. The antibody or antigen-binding fragment thereof of claim 1, wherein the VH comprises CDRs 1, 2, 3 with the amino acid sequences set forth in SEQ ID NOs: 31, 32, and 33, respectively, and the VL comprises CDRs 1, 2, 3 with the amino acid sequences set forth in SEQ ID NOs: 34, 35, and 36, respectively, wherein the VH CDRs 1, 2, 3 and VL CDRs 1, 2, 3 are determined according to Chothia definition.

9. The antibody or antigen-binding fragment thereof of claim 1, wherein the VH comprises CDRs 1, 2, 3 with the amino acid sequences set forth in SEQ ID NOs: 13, 14, and 15, respectively, and the VL comprises CDRs 1, 2, 3 with the amino acid sequences set forth in SEQ ID NOs: 16, 17, and 18, respectively, wherein the VH CDRs 1, 2, 3 and VL CDRs 1, 2, 3 are determined according to Kabat definition.

10. The antibody or antigen-binding fragment thereof of claim 1, wherein the VH comprises CDRs 1, 2, 3 with the amino acid sequences set forth in SEQ ID NOs: 37, 38, and 39, respectively, and the VL comprises CDRs 1, 2, 3 with the amino acid sequences set forth in SEQ ID NOs: 40, 41, 42, respectively, wherein the VH CDRs 1, 2, 3 and VL CDRs 1, 2, 3 are determined according to Chothia definition.

11. The antibody or antigen-binding fragment thereof of claim 1, wherein the VH comprises CDRs 1, 2, 3 with the amino acid sequences set forth in SEQ ID NOs: 19, 20, and 21, respectively, and the VL comprises CDRs 1, 2, 3 with the amino acid sequences set forth in SEQ ID NOs: 22, 23, and 24, respectively, wherein the VH CDRs 1, 2, 3 and VL CDRs 1, 2, 3 are determined according to Kabat definition.

12. The antibody or antigen-binding fragment thereof of claim 1, wherein the VH comprises CDRs 1, 2, 3 with the amino acid sequences set forth in SEQ ID NOs: 43, 44, and 45, respectively, and the VL comprises CDRs 1, 2, 3 with the amino acid sequences set forth in SEQ ID NOs: 46, 47, 48, respectively, wherein the VH CDRs 1, 2, 3 and VL CDRs 1, 2, 3 are determined according to Chothia definition.

13. A nucleic acid comprising a polynucleotide encoding a polypeptide comprising:
  (1) an immunoglobulin heavy chain or a fragment thereof comprising a heavy chain variable region (VH) comprising complementarity determining regions (CDRs) 1, 2, and 3 comprising the amino acid sequences set forth in SEQ ID NOs: 1, 2, and 3, respectively, and wherein the VH, when paired with a light chain variable region (VL) comprising the amino acid sequence set forth in SEQ ID NO: 56, 57, 58, or 80, binds to human OX40;
  (2) an immunoglobulin light chain or a fragment thereof comprising a VL comprising CDRs 1, 2, and 3 comprising the amino acid sequences set forth in SEQ ID NOs: 4, 5, and 6, respectively, and wherein the VL, when paired with a VH comprising the amino acid sequence set forth in SEQ ID NO: 53, 54, 55, or 79, binds to human OX40;
  (3) an immunoglobulin heavy chain or a fragment thereof comprising a heavy chain variable region (VH) comprising CDRs 1, 2, and 3 comprising the amino acid sequences set forth in SEQ ID NOs: 7, 8, and 9, respectively, and wherein the VH, when paired with a light chain variable region (VL) comprising the amino acid sequence set forth in SEQ ID NO: 62, 63, 64, 65, or 82, binds to human OX40; or
  (4) an immunoglobulin light chain or a fragment thereof comprising a VL comprising CDRs 1, 2, and 3 comprising the amino acid sequences set forth in SEQ ID NOs: 10, 11, and 12, respectively, and wherein the VL, when paired with a VH comprising the amino acid sequence set forth in SEQ ID NO: 59, 60, 61, or 81, binds to human OX40;
  (5) an immunoglobulin heavy chain or a fragment thereof comprising a heavy chain variable region (VH) comprising CDRs 1, 2, and 3 comprising the amino acid sequences set forth in SEQ ID NOs: 13, 14, and 15, respectively, and wherein the VH, when paired with a light chain variable region (VL) comprising the amino acid sequence set forth in SEQ ID NOs: 69, 70, 71, 72, or 84 binds to human OX40;
  (6) an immunoglobulin light chain or a fragment thereof comprising a VL comprising CDRs 1, 2, and 3 comprising the amino acid sequences set forth in SEQ ID NOs: 16, 17, and 18, respectively, and wherein the VL, when paired with a VH comprising the amino acid sequence set forth in SEQ ID NOs: 66, 67, 68, or 83, binds to human OX40;
  (7) an immunoglobulin heavy chain or a fragment thereof comprising a heavy chain variable region (VH) comprising CDRs 1, 2, and 3 comprising the amino acid sequences set forth in SEQ ID NOs: 19, 20, and 21, respectively, and wherein the VH, when paired with a light chain variable region (VL) comprising the amino acid sequence set forth in SEQ ID NOs: 76, 77, 78, or 86, binds to human OX40; or
  (8) an immunoglobulin light chain or a fragment thereof comprising a VL comprising CDRs 1, 2, and 3 comprising the amino acid sequences set forth in SEQ ID NOs: 22, 23, and 24, respectively, and wherein the VL, when paired with a VH comprising the amino acid sequence set forth in SEQ ID NO: 73, 74, 75, or 85, binds to human OX40.

14. A vector comprising the nucleic acid of claim 13.

15. A cell comprising the nucleic acid of claim 13.

16. A method of producing an antibody or an antigen-binding fragment thereof, the method comprising
culturing the cell of claim 15 under conditions sufficient for the cell to produce the antibody or the antigen-binding fragment thereof.

17. An antibody or antigen-binding fragment thereof that binds to human OX40, comprising a heavy chain variable region comprising VH CDRs 1, 2, 3, and a light chain variable region comprising VL CDRs 1, 2, 3, wherein:
  (1) the VH CDRs 1, 2, 3 are identical to complementarity determining regions in SEQ ID NO: 53, 54, 55, or 79, and the VL CDRs 1, 2, 3 are identical to complementary determining regions in SEQ ID NO: 56, 57, 58, or 80;

(2) the VH CDRs 1, 2, 3 are identical to complementarity determining regions in SEQ ID NO: 59, 60, 61, or 81, and the VL CDRs 1, 2, 3 are identical to complementary determining regions in SEQ ID NO: 62, 63, 64, 65, or 82;

(3) the VH CDRs 1, 2, 3 are identical to complementarity determining regions in SEQ ID NO: 66, 67, 68, or 83, and the VL CDRs 1, 2, 3 are identical to complementary determining regions in SEQ ID NO: 69, 70, 71, 72, or 84; or (4) the VH CDRs 1, 2, 3 are identical to complementarity determining regions in SEQ ID NO: 73, 74, 75, or 85, and the VL CDRs 1, 2, 3 are identical to complementary determining regions in SEQ ID NO: 76, 77, 78, or 86.

* * * * *

UNITED STATES PATENT AND TRADEMARK OFFICE
CERTIFICATE OF CORRECTION

| | | |
|---|---|---|
| PATENT NO. | : 11,999,790 B2 | Page 1 of 1 |
| APPLICATION NO. | : 17/141406 | |
| DATED | : June 4, 2024 | |
| INVENTOR(S) | : Yi Yang et al. | |

It is certified that error appears in the above-identified patent and that said Letters Patent is hereby corrected as shown below:

In the Specification

In Column 1, Line 7, delete "16/882,089," and insert -- 16/882,096, --.

Signed and Sealed this
Thirtieth Day of July, 2024

Katherine Kelly Vidal
*Director of the United States Patent and Trademark Office*